United States Patent
Jacobson et al.

(10) Patent No.: US 12,390,586 B2
(45) Date of Patent: *Aug. 19, 2025

(54) CONCURRENT INFUSION WITH COMMON LINE AUTO FLUSH

(71) Applicant: ICU Medical, Inc., San Clemente, CA (US)

(72) Inventors: James Duane Jacobson, Lindenhurst, IL (US); Gerald William Brann, Antiosh, IL (US)

(73) Assignee: ICU Medical, Inc., San Clemente, CA (US)

( * ) Notice: Subject to any disclaimer, the term of this patent is extended or adjusted under 35 U.S.C. 154(b) by 230 days.

This patent is subject to a terminal disclaimer.

(21) Appl. No.: 17/493,692

(22) Filed: Oct. 4, 2021

(65) Prior Publication Data

US 2022/0176037 A1 Jun. 9, 2022

Related U.S. Application Data

(63) Continuation of application No. 17/114,359, filed on Dec. 7, 2020, now Pat. No. 11,135,360.

(51) Int. Cl.
*A61M 5/168* (2006.01)
*A61M 5/14* (2006.01)
(Continued)

(52) U.S. Cl.
CPC ...... *A61M 5/16827* (2013.01); *A61M 5/1407* (2013.01); *G16H 20/17* (2018.01);
(Continued)

(58) Field of Classification Search
CPC .... A61M 5/14; A61M 5/1407; A61M 5/1409; A61M 5/142; A61M 5/145; A61M 5/168;
(Continued)

(56) References Cited

U.S. PATENT DOCUMENTS

| 3,401,337 A | 9/1968 | Beusman et al. |
| 3,484,681 A | 12/1969 | Grady, Jr. et al. |

(Continued)

FOREIGN PATENT DOCUMENTS

| AU | 2013216679 | 9/2013 |
| BR | PI0704229-9 | 11/2009 |

(Continued)

OTHER PUBLICATIONS

Alaedeen et al., "Total Parenteral Nutrition-Associated Hyperglycemia Correlates with Prolonged Mechanical Ventilation and Hospital Stay in Septic Infants", Journal of Pediatric Surgery, Jan. 2006, vol. 41, No. 1, pp. 239-244.

(Continued)

*Primary Examiner* — Scott J Medway
(74) *Attorney, Agent, or Firm* — Knobbe, Martens, Olson & Bear, LLP

(57) ABSTRACT

An infusion pump system and method provide concurrent infusion with common line auto flush. The infusion pump system has a first reservoir, a second reservoir, a junction, a mixing chamber, a common line having one end in fluid connection with the mixing chamber and having a terminal fluid delivery end, and an infusion pump. The method includes infusing the first fluid at a first rate along a first flow path; determining a common line flush volume value for the common line; switching to a concurrent infusion mode to drive a combination of the first fluid and the second fluid at the first rate along a second flow path including the common line; monitoring a volume of the combination of the first and second fluids driven at the first rate; and driving the combination of the first and second fluids at a combined rate along the second flow path when the monitored volume is equal to or greater than the common line flush volume value.

23 Claims, 11 Drawing Sheets

(51) Int. Cl.
　　*G06K 7/10* 　　　　(2006.01)
　　*G06K 19/07* 　　　(2006.01)
　　*G16H 20/17* 　　　(2018.01)
　　*G16H 40/40* 　　　(2018.01)
　　*G16H 40/67* 　　　(2018.01)

(52) U.S. Cl.
　　CPC ............. *G16H 40/40* (2018.01); *G16H 40/67*
　　　　(2018.01); *A61M 2005/1403* (2013.01); *A61M*
　　　　　　*2205/3334* (2013.01); *A61M 2205/502*
　　　　(2013.01); *A61M 2205/52* (2013.01); *G06K*
　　　　　　*7/10297* (2013.01); *G06K 2007/10504*
　　　　　　(2013.01); *G06K 19/0723* (2013.01)

(58) Field of Classification Search
　　CPC .......... A61M 5/16804; A61M 5/16827; A61M
　　　　　　5/16877; A61M 5/172; G06F 19/3468
　　See application file for complete search history.

(56) References Cited

U.S. PATENT DOCUMENTS

| | | |
|---|---|---|
| 3,699,320 A | 10/1972 | Zimmerman et al. |
| 3,727,074 A | 4/1973 | Keller et al. |
| 3,731,679 A | 5/1973 | Wilhelmson et al. |
| 3,768,084 A | 10/1973 | Haynes |
| 3,770,354 A | 11/1973 | Tsuruta et al. |
| 3,778,702 A | 12/1973 | Finger |
| 3,806,821 A | 4/1974 | Niemeyer et al. |
| 3,838,565 A | 10/1974 | Carlyle |
| 3,854,038 A | 12/1974 | McKinley |
| 3,886,459 A | 5/1975 | Hufford et al. |
| 3,890,554 A | 6/1975 | Yoshitake et al. |
| 3,894,431 A | 7/1975 | Muston et al. |
| 3,898,637 A | 8/1975 | Wolstenholme |
| 3,901,231 A | 8/1975 | Olson |
| 3,909,693 A | 9/1975 | Yoshitake et al. |
| 3,910,701 A | 10/1975 | Henderson |
| 3,911,343 A | 10/1975 | Oster |
| 3,919,608 A | 11/1975 | Usami et al. |
| 3,921,622 A | 11/1975 | Cole |
| 3,930,404 A | 1/1976 | Ryden, Jr. |
| 3,933,431 A | 1/1976 | Trujillo et al. |
| 3,935,876 A | 2/1976 | Massie et al. |
| 3,944,963 A | 3/1976 | Hively |
| 3,966,358 A | 6/1976 | Heimes et al. |
| 3,971,980 A | 7/1976 | Jungfer et al. |
| 3,974,681 A | 8/1976 | Namery |
| 3,974,683 A | 8/1976 | Martin |
| 3,985,467 A | 10/1976 | Lefferson |
| 3,990,444 A | 11/1976 | Vial |
| 3,997,888 A | 12/1976 | Kremer |
| 4,005,724 A | 2/1977 | Courtot |
| 4,014,206 A | 3/1977 | Taylor |
| 4,038,982 A | 8/1977 | Burke |
| 4,039,269 A | 8/1977 | Pickering |
| 4,048,474 A | 9/1977 | Olesen |
| 4,049,954 A | 9/1977 | Da Costa Vieira et al. |
| 4,055,175 A | 10/1977 | Clemens et al. |
| 4,057,228 A | 11/1977 | Völker et al. |
| 4,068,521 A | 1/1978 | Cosentino et al. |
| 4,078,562 A | 3/1978 | Friedman |
| 4,089,227 A | 5/1978 | Falgari et al. |
| 4,094,318 A | 6/1978 | Burke |
| 4,105,028 A | 8/1978 | Sadlier et al. |
| 4,114,144 A | 9/1978 | Hyman |
| 4,151,845 A | 5/1979 | Clemens |
| 4,155,362 A | 5/1979 | Jess |
| 4,164,986 A | 8/1979 | Eloy |
| 4,173,224 A | 11/1979 | Marx |
| 4,181,610 A | 1/1980 | Shintani et al. |
| 4,183,244 A | 1/1980 | Kohno et al. |
| 4,195,515 A | 4/1980 | Smoll |
| 4,210,138 A | 7/1980 | Jess et al. |
| 4,213,454 A | 7/1980 | Shim |
| 4,217,993 A | 8/1980 | Jess et al. |
| 4,240,294 A | 12/1980 | Grande |
| 4,240,438 A | 12/1980 | Updike et al. |
| 4,244,365 A | 1/1981 | McGill |
| 4,256,437 A | 3/1981 | Brown |
| 4,261,356 A | 4/1981 | Turner et al. |
| 4,264,861 A | 4/1981 | Radu et al. |
| 4,265,240 A | 5/1981 | Jenkins |
| 4,270,532 A | 6/1981 | Franetzki et al. |
| 4,277,226 A | 7/1981 | Archibald et al. |
| 4,278,085 A | 7/1981 | Shim |
| 4,280,495 A | 7/1981 | Lampert |
| 4,282,872 A | 8/1981 | Franetzki et al. |
| 4,286,202 A | 8/1981 | Clancy et al. |
| 4,290,346 A | 9/1981 | Bujan |
| 4,291,692 A | 9/1981 | Bowman et al. |
| 4,292,405 A | 9/1981 | Mascoli |
| 4,298,357 A | 11/1981 | Permic |
| 4,308,866 A | 1/1982 | Jeliffe |
| 4,312,341 A | 1/1982 | Zissimopoulos |
| 4,319,568 A | 3/1982 | Tregoning |
| 4,322,201 A | 3/1982 | Archibald |
| 4,323,849 A | 4/1982 | Smith |
| 4,324,662 A | 4/1982 | Schnell |
| 4,328,800 A | 5/1982 | Marx |
| 4,328,801 A | 5/1982 | Marx |
| 4,333,045 A | 6/1982 | Oltendorf |
| 4,343,316 A | 8/1982 | Jespersen |
| 4,344,429 A | 8/1982 | Gupton et al. |
| 4,346,707 A | 8/1982 | Whitney et al. |
| 4,360,019 A | 11/1982 | Portner et al. |
| 4,366,384 A | 12/1982 | Jensen |
| 4,367,736 A | 1/1983 | Gupton |
| 4,370,983 A | 2/1983 | Lichtenstein et al. |
| 4,373,527 A | 2/1983 | Fischell |
| 4,379,452 A | 4/1983 | DeVries |
| 4,381,005 A | 4/1983 | Bujan |
| 4,384,578 A | 5/1983 | Winkler |
| 4,385,247 A | 5/1983 | Satomi |
| 4,391,598 A | 7/1983 | Thompson |
| 4,392,849 A | 7/1983 | Petre et al. |
| 4,394,862 A | 7/1983 | Shim |
| 4,395,259 A | 7/1983 | Prestele et al. |
| 4,397,194 A | 8/1983 | Soltz |
| 4,399,362 A | 8/1983 | Cormier et al. |
| 4,407,659 A | 10/1983 | Adam |
| 4,411,651 A | 10/1983 | Schulman |
| 4,418,565 A | 12/1983 | St. John |
| 4,432,699 A | 2/1984 | Beckman et al. |
| 4,432,761 A | 2/1984 | Dawe |
| 4,432,762 A | 2/1984 | Dawe |
| 4,443,218 A | 4/1984 | Decant, Jr. et al. |
| 4,444,546 A | 4/1984 | Pazemenas |
| 4,447,191 A | 5/1984 | Bilstad et al. |
| 4,447,224 A | 5/1984 | Decant, Jr. et al. |
| 4,453,931 A | 6/1984 | Pastrone |
| 4,457,751 A | 7/1984 | Rodler |
| 4,463,301 A | 7/1984 | Moriguchi et al. |
| 4,464,170 A | 8/1984 | Clemens |
| 4,467,654 A | 8/1984 | Murakami et al. |
| 4,468,222 A | 8/1984 | Lundquist |
| 4,468,601 A | 8/1984 | Chamran et al. |
| 4,469,481 A | 9/1984 | Kobayashi |
| 4,475,666 A | 10/1984 | Bilbrey et al. |
| 4,475,901 A | 10/1984 | Kraegen et al. |
| 4,477,756 A | 10/1984 | Moriguchi |
| 4,479,760 A | 10/1984 | Bilstad et al. |
| 4,480,218 A | 10/1984 | Hair |
| 4,480,483 A | 11/1984 | McShane |
| 4,483,202 A | 11/1984 | Ogua et al. |
| 4,487,601 A | 12/1984 | Lindemann |
| 4,492,909 A | 1/1985 | Hartwig |
| 4,496,346 A | 1/1985 | Mosteller |
| 4,498,843 A | 2/1985 | Schneider et al. |
| 4,501,531 A | 2/1985 | Bilstad et al. |
| 4,504,263 A | 3/1985 | Steuer |
| 4,507,112 A | 3/1985 | Hillel |
| 4,510,266 A | 4/1985 | Eertink |
| 4,513,796 A | 4/1985 | Miller et al. |

(56) References Cited

U.S. PATENT DOCUMENTS

| | | |
|---|---|---|
| 4,515,584 A | 5/1985 | Abe et al. |
| 4,519,792 A | 5/1985 | Dawe |
| 4,521,212 A | 6/1985 | Ruschke |
| 4,525,163 A | 6/1985 | Slavik et al. |
| 4,526,568 A | 7/1985 | Clemens et al. |
| 4,526,574 A | 7/1985 | Pekkarinen |
| 4,529,401 A | 7/1985 | Leslie et al. |
| 4,533,350 A | 8/1985 | Danby et al. |
| 4,543,955 A | 10/1985 | Schroeppel |
| 4,551,134 A | 11/1985 | Slavik et al. |
| 4,553,958 A | 11/1985 | LeCocq |
| 4,559,036 A | 12/1985 | Wunsch |
| 4,559,037 A | 12/1985 | Franetzki et al. |
| 4,559,044 A | 12/1985 | Robinson |
| 4,559,454 A | 12/1985 | Kramer |
| 4,565,500 A | 1/1986 | Jeensalute et al. |
| 4,583,981 A | 4/1986 | Urquhart et al. |
| 4,587,473 A | 5/1986 | Turvey |
| 4,607,520 A | 8/1986 | Dam |
| 4,617,014 A | 10/1986 | Cannon et al. |
| 4,624,661 A | 11/1986 | Arimond |
| 4,627,835 A | 12/1986 | Fenton, Jr. |
| 4,633,878 A | 1/1987 | Bombardieri |
| 4,634,426 A | 1/1987 | kamen |
| 4,634,427 A | 1/1987 | Hannula et al. |
| 4,636,144 A | 1/1987 | Abe et al. |
| 4,637,813 A | 1/1987 | DeVries |
| 4,645,489 A | 2/1987 | Krumme |
| 4,648,869 A | 3/1987 | Bobo, Jr. |
| 4,652,260 A | 3/1987 | Fenton, Jr. et al. |
| 4,658,244 A | 4/1987 | Meijer |
| 4,668,216 A | 5/1987 | Martin |
| 4,668,945 A | 5/1987 | Aldrovandi et al. |
| 4,673,334 A | 6/1987 | Allington et al. |
| 4,673,389 A | 6/1987 | Archibald et al. |
| 4,676,776 A | 6/1987 | Howson et al. |
| 4,677,359 A | 6/1987 | Enami et al. |
| 4,678,979 A | 7/1987 | Hori |
| 4,678,998 A | 7/1987 | Muramatsu |
| 4,679,562 A | 7/1987 | Luksha |
| 4,683,428 A | 7/1987 | Gete |
| 4,685,903 A | 8/1987 | Cable et al. |
| 4,690,673 A | 9/1987 | Blomquist |
| 4,691,153 A | 9/1987 | Nishimura |
| 4,692,145 A | 9/1987 | Weyant |
| 4,696,671 A | 9/1987 | Epstein et al. |
| 4,697,129 A | 9/1987 | Enami et al. |
| 4,702,675 A | 10/1987 | Aldrovandi et al. |
| 4,705,506 A | 11/1987 | Archibald et al. |
| 4,710,106 A | 12/1987 | Iwata et al. |
| 4,714,462 A | 12/1987 | DiDomenico |
| 4,714,463 A | 12/1987 | Archibald et al. |
| 4,718,576 A | 1/1988 | Tamura et al. |
| 4,720,636 A | 1/1988 | Benner |
| 4,722,224 A | 2/1988 | Scheller et al. |
| 4,722,734 A | 2/1988 | Kolin |
| 4,731,051 A | 3/1988 | Fischell |
| 4,731,057 A | 3/1988 | Tanaka et al. |
| 4,737,711 A | 4/1988 | O'Hare |
| 4,739,346 A | 4/1988 | Buckley |
| 4,741,732 A | 5/1988 | Crankshaw et al. |
| 4,741,736 A | 5/1988 | Brown |
| 4,748,857 A | 6/1988 | Nakagawa |
| 4,751,445 A | 6/1988 | Sakai |
| 4,756,706 A | 7/1988 | Kerns et al. |
| 4,758,228 A | 7/1988 | Williams |
| 4,763,525 A | 8/1988 | Cobb |
| 4,764,166 A | 8/1988 | Spani et al. |
| 4,764,697 A | 8/1988 | Christiaens |
| 4,769,001 A | 9/1988 | Prince |
| 4,776,842 A | 10/1988 | Franetzki et al. |
| 4,781,687 A | 11/1988 | Wall |
| 4,784,576 A | 11/1988 | Bloom et al. |
| 4,785,184 A | 11/1988 | Bien et al. |
| 4,785,799 A | 11/1988 | Schoon et al. |
| 4,785,969 A | 11/1988 | McLaughlin |
| 4,786,800 A | 11/1988 | Kamen |
| 4,789,014 A | 12/1988 | DiGianfilippo |
| 4,797,655 A | 1/1989 | Orndal et al. |
| 4,803,389 A | 2/1989 | Ogawa et al. |
| 4,803,625 A | 2/1989 | Fu et al. |
| 4,818,186 A | 4/1989 | Pastrone et al. |
| 4,820,281 A | 4/1989 | Lawler |
| 4,821,558 A | 4/1989 | Pastrone et al. |
| 4,828,545 A | 5/1989 | Epstein et al. |
| 4,828,693 A | 5/1989 | Lindsay |
| 4,829,448 A | 5/1989 | Balding et al. |
| 4,838,856 A | 6/1989 | Mulreany et al. |
| 4,838,857 A | 6/1989 | Strowe et al. |
| 4,840,542 A | 6/1989 | Abbott |
| 4,842,584 A | 6/1989 | Pastrone et al. |
| 4,845,487 A | 7/1989 | Frantz et al. |
| 4,846,792 A | 7/1989 | Bobo et al. |
| 4,850,805 A | 7/1989 | Madsen et al. |
| 4,851,755 A | 7/1989 | Fincher |
| 4,854,324 A | 8/1989 | Hirschman et al. |
| 4,856,339 A | 8/1989 | Williams |
| 4,857,048 A | 8/1989 | Simons et al. |
| 4,857,050 A | 8/1989 | Lentz et al. |
| 4,858,154 A | 8/1989 | Anderson et al. |
| 4,863,425 A | 9/1989 | Slate et al. |
| 4,865,584 A | 9/1989 | Epstein et al. |
| 4,869,722 A | 9/1989 | Heyman |
| 4,874,359 A | 10/1989 | White et al. |
| 4,881,413 A | 11/1989 | Georgi et al. |
| 4,882,575 A | 11/1989 | Kawahara |
| 4,884,013 A | 11/1989 | Jackson et al. |
| 4,884,065 A | 11/1989 | Crouse et al. |
| 4,886,422 A | 12/1989 | Takeuchi et al. |
| 4,898,576 A | 2/1990 | Philip |
| 4,898,578 A | 2/1990 | Rubalcaba, Jr. |
| 4,906,103 A | 3/1990 | Kao |
| 4,908,017 A | 3/1990 | Howson et al. |
| 4,908,019 A | 3/1990 | Urquhart et al. |
| 4,910,475 A | 3/1990 | Lin |
| 4,919,595 A | 4/1990 | Likuski et al. |
| 4,919,596 A | 4/1990 | Slate et al. |
| 4,925,444 A | 5/1990 | Orkin et al. |
| 4,927,411 A | 5/1990 | Pastrone et al. |
| 4,930,358 A | 6/1990 | Motegi et al. |
| 4,936,820 A | 6/1990 | Dennehey |
| 4,936,828 A | 6/1990 | Chiang |
| 4,938,079 A | 7/1990 | Goldberg |
| 4,943,279 A | 7/1990 | Samiotes et al. |
| 4,946,439 A | 8/1990 | Eggers |
| 4,947,856 A | 8/1990 | Beard |
| 4,950,235 A | 8/1990 | Slate et al. |
| 4,950,244 A | 8/1990 | Fellingham |
| 4,959,050 A | 9/1990 | Bobo, Jr. |
| 4,966,579 A | 10/1990 | Polaschegg |
| 4,968,941 A | 11/1990 | Rogers |
| 4,972,842 A | 11/1990 | Korten et al. |
| 4,976,687 A | 12/1990 | Martin |
| 4,978,335 A | 12/1990 | Arthur, III |
| 4,979,940 A | 12/1990 | Lapp et al. |
| 4,981,467 A | 1/1991 | Bobo et al. |
| 5,000,663 A | 3/1991 | Gorton |
| 5,000,739 A | 3/1991 | Kulisz et al. |
| 5,006,050 A | 4/1991 | Cooke et al. |
| 5,010,473 A | 4/1991 | Jacobs |
| 5,014,714 A | 5/1991 | Millay et al. |
| 5,014,798 A | 5/1991 | Glynn |
| 5,018,945 A | 5/1991 | D'Silva |
| 5,026,348 A | 6/1991 | Venegas |
| 5,028,857 A | 7/1991 | Taghezout |
| 5,032,112 A | 7/1991 | Fairchild et al. |
| 5,034,004 A | 7/1991 | Crankshaw |
| 5,035,143 A | 7/1991 | Latimer et al. |
| 5,040,699 A | 8/1991 | Gangemi |
| 5,041,086 A | 8/1991 | Koenig et al. |
| 5,043,706 A | 8/1991 | Oliver |
| 5,045,069 A | 9/1991 | Imparato |
| 5,049,047 A | 9/1991 | Polaschegg et al. |
| 5,052,230 A | 10/1991 | Lang |

(56) References Cited

U.S. PATENT DOCUMENTS

| | | |
|---|---|---|
| 5,053,747 A | 10/1991 | Slate et al. |
| 5,055,761 A | 10/1991 | Mills |
| 5,056,992 A | 10/1991 | Simons |
| 5,058,161 A | 10/1991 | Weiss |
| 5,059,171 A | 10/1991 | Bridge |
| 5,063,603 A | 11/1991 | Burt |
| 5,064,412 A | 11/1991 | Henke et al. |
| 5,078,683 A | 1/1992 | Sancoff et al. |
| 5,084,663 A | 1/1992 | Olsson |
| 5,084,828 A | 1/1992 | Kaufman et al. |
| 5,088,981 A | 2/1992 | Howson et al. |
| 5,096,385 A | 3/1992 | Georgi et al. |
| 5,097,505 A | 3/1992 | Weiss |
| 5,100,380 A | 3/1992 | Epstein et al. |
| 5,102,392 A | 4/1992 | Sakai et al. |
| 5,103,211 A | 4/1992 | Daoud et al. |
| 5,104,374 A | 4/1992 | Bishko et al. |
| 5,108,367 A | 4/1992 | Epstein et al. |
| 5,109,850 A | 5/1992 | Blanco et al. |
| 5,116,203 A | 5/1992 | Nartwick et al. |
| 5,116,312 A | 5/1992 | Blakenship et al. |
| 5,116,316 A | 5/1992 | Sertic |
| 5,123,275 A | 6/1992 | Daoud et al. |
| 5,124,627 A | 6/1992 | Okada |
| 5,125,499 A | 6/1992 | Saathoff et al. |
| 5,131,816 A | 7/1992 | Brown |
| 5,132,603 A | 7/1992 | Yoshimoto |
| 5,153,827 A | 10/1992 | Coutre et al. |
| 5,158,441 A | 10/1992 | Aid |
| 5,161,222 A | 11/1992 | Montejo et al. |
| 5,174,472 A | 12/1992 | Raque et al. |
| 5,176,631 A | 1/1993 | Koenig |
| 5,176,646 A | 1/1993 | Kuroda |
| 5,179,340 A | 1/1993 | Rogers |
| 5,180,287 A | 1/1993 | Natwick et al. |
| 5,181,910 A | 1/1993 | Scanlon |
| 5,186,057 A | 2/1993 | Everhart |
| 5,188,603 A | 2/1993 | Vaillancourt |
| 5,190,522 A | 3/1993 | Wocicki et al. |
| 5,191,795 A | 3/1993 | Fellingham et al. |
| 5,192,340 A | 3/1993 | Grant et al. |
| 5,194,796 A | 3/1993 | Domeki et al. |
| 5,198,776 A | 3/1993 | Carr |
| 5,200,090 A | 4/1993 | Ford |
| 5,205,819 A | 4/1993 | Ross et al. |
| 5,206,522 A | 4/1993 | Danby et al. |
| 5,207,642 A | 5/1993 | Orkin et al. |
| 5,211,626 A | 5/1993 | Frank et al. |
| 5,213,573 A | 5/1993 | Sorich et al. |
| 5,215,450 A | 6/1993 | Tamari |
| 5,216,597 A | 6/1993 | Beckers |
| 5,219,099 A | 6/1993 | Spence et al. |
| 5,219,327 A | 6/1993 | Okada |
| 5,221,268 A | 6/1993 | Barton et al. |
| 5,229,713 A | 7/1993 | Bullock et al. |
| 5,232,476 A | 8/1993 | Grant |
| 5,233,571 A | 8/1993 | Wirtschafter |
| 5,237,309 A | 8/1993 | Frantz et al. |
| 5,242,406 A | 9/1993 | Gross et al. |
| 5,242,408 A | 9/1993 | Jhuboo et al. |
| 5,243,982 A | 9/1993 | Möstl et al. |
| 5,244,463 A | 9/1993 | Cordner, Jr. et al. |
| 5,244,568 A | 9/1993 | Lindsay et al. |
| 5,254,096 A | 10/1993 | Rondelet et al. |
| 5,256,155 A | 10/1993 | Yerlikaya et al. |
| 5,256,156 A | 10/1993 | Kern et al. |
| 5,256,157 A | 10/1993 | Samiotes et al. |
| 5,257,206 A | 10/1993 | Hanson |
| 5,260,665 A | 11/1993 | Goldberg |
| 5,267,980 A | 12/1993 | Dirr et al. |
| 5,274,316 A | 12/1993 | Evans et al. |
| 5,276,610 A | 1/1994 | Maeda et al. |
| 5,280,728 A | 1/1994 | Sato et al. |
| 5,283,510 A | 2/1994 | Tamaki et al. |
| 5,287,851 A | 2/1994 | Beran et al. |
| 5,292,306 A | 3/1994 | Wynkoop et al. |
| 5,295,967 A | 3/1994 | Rondelet et al. |
| 5,298,021 A | 3/1994 | Sherer |
| 5,303,585 A | 4/1994 | Lichte |
| 5,304,126 A | 4/1994 | Epstein et al. |
| 5,304,216 A | 4/1994 | Wallace |
| 5,308,333 A | 5/1994 | Skakoon |
| 5,317,506 A | 5/1994 | Coutre et al. |
| 5,319,363 A | 6/1994 | Welch et al. |
| 5,319,979 A | 6/1994 | Abrahamson |
| 5,321,392 A | 6/1994 | Skakoon et al. |
| 5,325,170 A | 6/1994 | Bornhop |
| 5,325,728 A | 7/1994 | Zimmerman et al. |
| 5,328,460 A | 7/1994 | Lord et al. |
| 5,330,634 A | 7/1994 | Wong et al. |
| 5,333,497 A | 8/1994 | Braend et al. |
| 5,336,051 A | 8/1994 | Tamari |
| 5,338,157 A | 8/1994 | Blomquist |
| 5,342,298 A | 8/1994 | Michaels |
| 5,343,734 A | 9/1994 | Maeda et al. |
| 5,343,885 A | 9/1994 | Grant |
| 5,346,466 A | 9/1994 | Yerlikaya et al. |
| 5,356,378 A | 10/1994 | Doan et al. |
| 5,359,271 A | 10/1994 | Husher |
| D352,778 S | 11/1994 | Irvin et al. |
| 5,364,346 A | 11/1994 | Schrezenmeir |
| 5,366,346 A | 11/1994 | Danby |
| 5,368,562 A | 11/1994 | Blomquist et al. |
| 5,374,865 A | 12/1994 | Yoshimura et al. |
| 5,376,070 A | 12/1994 | Purvis et al. |
| 5,378,231 A | 1/1995 | Johnson et al. |
| 5,382,232 A | 1/1995 | Hague et al. |
| 5,383,369 A | 1/1995 | Khuri-Yakub et al. |
| 5,389,071 A | 2/1995 | Kawahara et al. |
| 5,389,078 A | 2/1995 | Zalesky et al. |
| 5,392,638 A | 2/1995 | Kawahara |
| 5,394,732 A | 3/1995 | Johnson et al. |
| 5,395,320 A | 3/1995 | Padda et al. |
| 5,399,171 A | 3/1995 | Bowman et al. |
| 5,406,954 A | 4/1995 | Tomita |
| 5,408,326 A | 4/1995 | Priestley |
| 5,415,528 A | 5/1995 | Ogden et al. |
| 5,417,119 A | 5/1995 | Smoll |
| 5,417,222 A | 5/1995 | Dempsey et al. |
| 5,417,395 A | 5/1995 | Fowler et al. |
| 5,418,443 A | 5/1995 | Kikuchi |
| 5,421,208 A | 6/1995 | Packard et al. |
| 5,423,748 A | 6/1995 | Uhala |
| 5,423,749 A | 6/1995 | Merte et al. |
| 5,423,759 A | 6/1995 | Campbell |
| 5,428,284 A | 6/1995 | Kaneda et al. |
| 5,429,485 A | 7/1995 | Dodge |
| 5,429,601 A | 7/1995 | Conley |
| 5,429,602 A | 7/1995 | Hauser |
| 5,431,627 A | 7/1995 | Pastrone et al. |
| 5,434,508 A | 7/1995 | Ishida |
| 5,437,624 A | 8/1995 | Langley et al. |
| 5,444,316 A | 8/1995 | Ohya et al. |
| 5,444,378 A | 8/1995 | Rogers |
| 5,445,621 A | 8/1995 | Poli et al. |
| 5,450,758 A | 9/1995 | Smoll |
| 5,451,881 A | 9/1995 | Finger |
| 5,455,423 A | 10/1995 | Mount et al. |
| 5,455,851 A | 10/1995 | Chaco et al. |
| 5,463,906 A | 11/1995 | Spani et al. |
| 5,464,392 A | 11/1995 | Epstein et al. |
| 5,465,082 A | 11/1995 | Chaco |
| 5,469,851 A | 11/1995 | Lipschutz |
| 5,473,948 A | 12/1995 | Moss et al. |
| 5,480,294 A | 1/1996 | Di Perna et al. |
| 5,482,438 A | 1/1996 | Anderson et al. |
| 5,485,408 A | 1/1996 | Blomquist |
| 5,486,286 A | 1/1996 | Peterson et al. |
| 5,489,265 A | 2/1996 | Montalvo et al. |
| 5,495,566 A | 2/1996 | Kwatinetz |
| 5,496,273 A | 3/1996 | Pastrone et al. |
| 5,505,696 A | 4/1996 | Miki |
| 5,505,828 A | 4/1996 | Wong et al. |
| 5,507,288 A | 4/1996 | Bocker et al. |

(56) References Cited

U.S. PATENT DOCUMENTS

| | | |
|---|---|---|
| 5,507,412 A | 4/1996 | Ebert et al. |
| 5,520,637 A | 5/1996 | Pager et al. |
| 5,522,798 A | 6/1996 | Johnson et al. |
| 5,522,799 A | 6/1996 | Furukawa |
| 5,527,630 A | 6/1996 | Nagata |
| 5,533,389 A | 7/1996 | Kamen et al. |
| 5,537,853 A | 7/1996 | Finburgh et al. |
| 5,542,040 A | 7/1996 | Chang et al. |
| 5,545,140 A | 8/1996 | Conero et al. |
| 5,547,470 A | 8/1996 | Johnson et al. |
| 5,551,850 A | 9/1996 | Williamson et al. |
| 5,554,013 A | 9/1996 | Owens et al. |
| 5,554,115 A | 9/1996 | Thomas et al. |
| 5,558,638 A | 9/1996 | Evers et al. |
| 5,562,615 A | 10/1996 | Nassif |
| 5,563,486 A | 10/1996 | Yamamoto et al. |
| 5,572,105 A | 11/1996 | Nojima et al. |
| 5,573,502 A | 11/1996 | LeCocq et al. |
| 5,583,280 A | 12/1996 | Mo et al. |
| 5,584,667 A | 12/1996 | Davis |
| 5,584,806 A | 12/1996 | Amano |
| 5,586,868 A | 12/1996 | Lawless et al. |
| 5,590,653 A | 1/1997 | Aida et al. |
| 5,594,786 A | 1/1997 | Chaco et al. |
| 5,600,073 A | 2/1997 | Hill |
| 5,601,420 A | 2/1997 | Warner et al. |
| 5,609,575 A | 3/1997 | Larson et al. |
| 5,609,576 A | 3/1997 | Voss |
| 5,611,784 A | 3/1997 | Barresi et al. |
| 5,616,124 A | 4/1997 | Hague et al. |
| 5,620,312 A | 4/1997 | Hyman et al. |
| 5,620,608 A | 4/1997 | Rosa et al. |
| 5,626,140 A | 5/1997 | Feldman et al. |
| 5,626,151 A | 5/1997 | Linden |
| 5,626,563 A | 5/1997 | Dodge et al. |
| 5,627,443 A | 5/1997 | Kimura et al. |
| 5,628,309 A | 5/1997 | Brown |
| 5,628,731 A | 5/1997 | Dodge et al. |
| 5,630,710 A | 5/1997 | Tune et al. |
| 5,634,896 A | 6/1997 | Bryant et al. |
| 5,637,095 A | 6/1997 | Nason et al. |
| 5,640,075 A | 6/1997 | Brasseur et al. |
| 5,640,150 A | 6/1997 | Atwater |
| 5,643,212 A | 7/1997 | Coutre et al. |
| 5,648,710 A | 7/1997 | Ikeda |
| 5,649,536 A | 7/1997 | Ogura et al. |
| 5,651,775 A | 7/1997 | Walker et al. |
| 5,657,000 A | 8/1997 | Ellingboe |
| 5,658,133 A | 8/1997 | Anderson et al. |
| 5,658,250 A | 8/1997 | Blomquist et al. |
| 5,659,234 A | 8/1997 | Cresens |
| 5,661,245 A | 8/1997 | Svoboda et al. |
| D384,052 S | 9/1997 | Kodosky |
| 5,662,612 A | 9/1997 | Niehoff |
| 5,665,065 A | 9/1997 | Colman et al. |
| 5,669,877 A | 9/1997 | Blomquist |
| 5,672,154 A | 9/1997 | Sillén et al. |
| 5,672,832 A | 9/1997 | Cucci et al. |
| 5,681,285 A | 10/1997 | Ford et al. |
| 5,681,286 A | 10/1997 | Niehoff |
| 5,685,844 A | 11/1997 | Marttila |
| 5,685,866 A | 11/1997 | Lopez |
| 5,687,717 A | 11/1997 | Halpern et al. |
| 5,689,229 A | 11/1997 | Chaco et al. |
| 5,691,613 A | 11/1997 | Gutwillinger |
| 5,695,464 A | 12/1997 | Viallet |
| 5,695,473 A | 12/1997 | Olsen |
| 5,697,899 A | 12/1997 | Hillman et al. |
| 5,697,916 A | 12/1997 | Schraga |
| 5,712,795 A | 1/1998 | Layman et al. |
| 5,713,856 A | 2/1998 | Eggers et al. |
| 5,714,691 A | 2/1998 | Hill |
| 5,718,562 A | 2/1998 | Lawless et al. |
| 5,718,569 A | 2/1998 | Holst |
| 5,720,721 A | 2/1998 | Dumas et al. |
| 5,722,417 A | 3/1998 | Rudolph |
| 5,728,074 A | 3/1998 | Castellano et al. |
| 5,728,948 A | 3/1998 | Bignell et al. |
| 5,733,257 A | 3/1998 | Stemby |
| 5,733,259 A | 3/1998 | Valcke et al. |
| 5,734,464 A | 3/1998 | Gibbs |
| 5,738,659 A | 4/1998 | Neer et al. |
| 5,743,856 A | 4/1998 | Oka et al. |
| 5,744,027 A | 4/1998 | Connell et al. |
| 5,744,929 A | 4/1998 | Miyazaki |
| 5,745,378 A | 4/1998 | Barker et al. |
| 5,752,813 A | 5/1998 | Tyner et al. |
| 5,752,918 A | 5/1998 | Fowler et al. |
| 5,752,919 A | 5/1998 | Schrimpf |
| 5,755,691 A | 5/1998 | Hilborne |
| 5,758,643 A | 6/1998 | Wong et al. |
| 5,761,072 A | 6/1998 | Bardsley, Jr. et al. |
| 5,764,034 A | 6/1998 | Bowman et al. |
| 5,766,155 A | 6/1998 | Hyman et al. |
| 5,772,635 A | 6/1998 | Dastur et al. |
| 5,778,256 A | 7/1998 | Darbee |
| 5,781,442 A | 7/1998 | Engleson et al. |
| 5,782,805 A | 7/1998 | Meinzer et al. |
| 5,788,669 A | 8/1998 | Peterson |
| 5,788,674 A | 8/1998 | McWilliams |
| 5,789,923 A | 8/1998 | Shimoyama et al. |
| 5,792,069 A | 8/1998 | Greenwald et al. |
| 5,793,211 A | 8/1998 | Shimoyama et al. |
| 5,795,327 A | 8/1998 | Wilson et al. |
| 5,798,934 A | 8/1998 | Saigo et al. |
| 5,800,387 A | 9/1998 | Duffy et al. |
| 5,803,712 A | 9/1998 | Davis et al. |
| 5,803,917 A | 9/1998 | Butterfield |
| 5,805,455 A | 9/1998 | Lipps |
| 5,807,322 A | 9/1998 | Lindsey et al. |
| 5,810,770 A | 9/1998 | Chin et al. |
| 5,813,972 A | 9/1998 | Nazarian et al. |
| 5,814,004 A | 9/1998 | Tamari |
| 5,814,015 A | 9/1998 | Gargano et al. |
| 5,816,779 A | 10/1998 | Lawless et al. |
| 5,822,715 A | 10/1998 | Worthington et al. |
| 5,827,179 A | 10/1998 | Lichter et al. |
| 5,827,223 A | 10/1998 | Butterfield |
| 5,832,448 A | 11/1998 | Brown |
| 5,836,910 A | 11/1998 | Duffy et al. |
| 5,841,261 A | 11/1998 | Nojima et al. |
| 5,841,284 A | 11/1998 | Takahashi |
| 5,843,035 A | 12/1998 | Bowman |
| 5,848,971 A | 12/1998 | Fowler et al. |
| 5,850,344 A | 12/1998 | Conkright |
| 5,857,843 A | 1/1999 | Leason et al. |
| 5,864,330 A | 1/1999 | Haynes |
| 5,865,805 A | 2/1999 | Ziemba |
| 5,867,821 A | 2/1999 | Ballantyne et al. |
| 5,871,465 A | 2/1999 | Vasko |
| 5,872,453 A | 2/1999 | Shimoyama et al. |
| 5,875,195 A | 2/1999 | Dixon |
| 5,882,300 A | 3/1999 | Malinouskas et al. |
| 5,882,339 A | 3/1999 | Beiser et al. |
| 5,885,245 A | 3/1999 | Lynch et al. |
| 5,889,379 A | 3/1999 | Yanagi et al. |
| 5,891,051 A | 4/1999 | Han et al. |
| 5,894,209 A | 4/1999 | Takagi et al. |
| 5,897,493 A | 4/1999 | Brown |
| 5,897,498 A | 4/1999 | Canfield, II et al. |
| 5,898,292 A | 4/1999 | Takemoto et al. |
| 5,899,665 A | 5/1999 | Makino et al. |
| 5,901,150 A | 5/1999 | Jhuboo et al. |
| 5,904,666 A | 5/1999 | DeDecker et al. |
| 5,904,668 A | 5/1999 | Hyman et al. |
| 5,905,207 A | 5/1999 | Schalk |
| 5,906,598 A | 5/1999 | Giesier |
| 5,910,252 A | 6/1999 | Truitt et al. |
| 5,915,240 A | 6/1999 | Karpf |
| 5,920,263 A | 7/1999 | Huttenhoff et al. |
| 5,923,159 A | 7/1999 | Ezell |
| 5,924,074 A | 7/1999 | Evans |
| 5,927,349 A | 7/1999 | Martucci |
| 5,932,119 A | 8/1999 | Kaplan et al. |

(56) References Cited

U.S. PATENT DOCUMENTS

| | | |
|---|---|---|
| 5,932,987 A | 8/1999 | McLoughlin |
| 5,935,066 A | 8/1999 | Harris |
| 5,935,099 A | 8/1999 | Peterson et al. |
| 5,935,106 A | 8/1999 | Olsen |
| 5,938,634 A | 8/1999 | Packard |
| 5,938,636 A | 8/1999 | Kramer et al. |
| 5,941,846 A | 8/1999 | Duffy et al. |
| 5,944,660 A | 8/1999 | Kimball et al. |
| 5,947,911 A | 9/1999 | Wong et al. |
| 5,954,527 A | 9/1999 | Jhuboo et al. |
| 5,954,696 A | 9/1999 | Ryan et al. |
| 5,956,023 A | 9/1999 | Lyle et al. |
| 5,956,501 A | 9/1999 | Brown |
| 5,957,885 A | 9/1999 | Bollish et al. |
| 5,957,890 A | 9/1999 | Mann et al. |
| 5,971,594 A | 10/1999 | Sahai et al. |
| 5,973,497 A | 10/1999 | Bergk et al. |
| 5,975,081 A | 11/1999 | Hood et al. |
| 5,989,222 A | 11/1999 | Cole et al. |
| 5,990,838 A | 11/1999 | Burns et al. |
| 5,991,525 A | 11/1999 | Shah et al. |
| 5,993,393 A | 11/1999 | Ryan et al. |
| 5,994,876 A | 11/1999 | Canny et al. |
| 5,997,476 A | 12/1999 | Brown |
| 6,000,828 A | 12/1999 | Leet |
| 6,003,006 A | 12/1999 | Colella et al. |
| 6,003,388 A | 12/1999 | Oeftering |
| 6,012,034 A | 1/2000 | Hamparian et al. |
| 6,017,318 A | 1/2000 | Gauthier et al. |
| 6,017,493 A | 1/2000 | Cambron |
| 6,021,392 A | 2/2000 | Lester et al. |
| 6,023,977 A | 2/2000 | Langdon et al. |
| 6,024,539 A | 2/2000 | Blomquist |
| 6,027,441 A | 2/2000 | Cantu |
| 6,028,412 A | 2/2000 | Shine et al. |
| 6,032,676 A | 3/2000 | Moore |
| 6,033,561 A | 3/2000 | Schoendorfer |
| 6,036,017 A | 3/2000 | Bayliss, IV |
| 6,068,612 A | 5/2000 | Bowman |
| 6,068,615 A | 5/2000 | Brown et al. |
| 6,073,106 A | 6/2000 | Rozen et al. |
| 6,077,246 A | 6/2000 | Kullas et al. |
| 6,083,206 A | 7/2000 | Molko |
| 6,089,104 A | 7/2000 | Chang |
| 6,104,295 A | 8/2000 | Gaisser et al. |
| 6,110,152 A | 8/2000 | Kovelman |
| 6,110,153 A | 8/2000 | Davis |
| RE36,871 E | 9/2000 | Epstein et al. |
| 6,120,459 A | 9/2000 | Nitzan et al. |
| 6,122,536 A | 9/2000 | Sun et al. |
| 6,142,008 A | 11/2000 | Cole et al. |
| 6,150,942 A | 11/2000 | O'Brien |
| 6,157,914 A | 12/2000 | Seto et al. |
| 6,158,288 A | 12/2000 | Smith |
| 6,158,965 A | 12/2000 | Butterfield et al. |
| 6,159,147 A | 12/2000 | Lichter et al. |
| 6,159,186 A | 12/2000 | Wickham et al. |
| 6,164,921 A | 12/2000 | Moubayed et al. |
| 6,168,561 B1 | 1/2001 | Cantu |
| 6,178,827 B1 | 1/2001 | Feller |
| 6,182,667 B1 | 2/2001 | Hanks et al. |
| 6,186,141 B1 | 2/2001 | Pike et al. |
| 6,189,105 B1 | 2/2001 | Lopes |
| 6,192,752 B1 | 2/2001 | Blaine |
| 6,195,589 B1 | 2/2001 | Ketcham |
| 6,202,711 B1 | 3/2001 | Martucci |
| 6,203,528 B1 | 3/2001 | Deckert |
| 6,208,107 B1 | 3/2001 | Maske et al. |
| 6,212,936 B1 | 4/2001 | Meisberger |
| 6,213,972 B1 | 4/2001 | Butterfield |
| 6,231,320 B1 | 5/2001 | Lawless et al. |
| 6,234,176 B1 | 5/2001 | Domae et al. |
| 6,236,326 B1 | 5/2001 | Murphy et al. |
| 6,237,398 B1 | 5/2001 | Porat et al. |
| 6,241,704 B1 | 6/2001 | Peterson et al. |
| 6,248,067 B1 | 6/2001 | Causey, III et al. |
| 6,250,132 B1 | 6/2001 | Drzewiecki |
| 6,259,355 B1 | 7/2001 | Chaco et al. |
| 6,259,587 B1 | 7/2001 | Sheldon et al. |
| 6,261,065 B1 | 7/2001 | Nayak |
| 6,262,946 B1 | 7/2001 | Khuri-Yakub et al. |
| 6,267,559 B1 | 7/2001 | Mossman et al. |
| 6,267,725 B1 | 7/2001 | Dubberstein et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,277,099 B1 | 8/2001 | Strowe et al. |
| 6,280,380 B1 | 8/2001 | Bardy |
| 6,280,391 B1 | 8/2001 | Olson et al. |
| 6,280,408 B1 | 8/2001 | Sipin |
| 6,283,761 B1 | 9/2001 | Joao |
| 6,285,155 B1 | 9/2001 | Maske et al. |
| 6,312,378 B1 | 11/2001 | Bardy |
| 6,322,516 B1 | 11/2001 | Masuda et al. |
| 6,330,351 B1 | 12/2001 | Yasunaga |
| 6,336,053 B1 | 1/2002 | Beatty |
| 6,337,675 B1 | 1/2002 | Toffolo et al. |
| 6,345,539 B1 | 2/2002 | Rawes et al. |
| 6,347,553 B1 | 2/2002 | Morris et al. |
| 6,349,740 B1 | 2/2002 | Cho et al. |
| 6,358,225 B1 | 3/2002 | Butterfield |
| 6,358,387 B1 | 3/2002 | Kopf-Sill et al. |
| 6,362,591 B1 | 3/2002 | Moberg |
| 6,385,505 B1 | 5/2002 | Lipps |
| 6,386,050 B1 | 5/2002 | Yin et al. |
| 6,394,958 B1 | 5/2002 | Bratteli et al. |
| 6,396,583 B1 | 5/2002 | Clare |
| D459,362 S | 6/2002 | Platz |
| 6,398,760 B1 | 6/2002 | Danby |
| 6,405,076 B1 | 6/2002 | Taylor et al. |
| 6,408,679 B1 | 6/2002 | Kline-Schoder et al. |
| 6,409,699 B1 | 6/2002 | Ash |
| 6,413,238 B1 | 7/2002 | Maget |
| 6,416,291 B1 | 7/2002 | Butterfield et al. |
| 6,418,334 B1 | 7/2002 | Unger et al. |
| 6,418,535 B1 | 7/2002 | Kulakowski et al. |
| 6,445,053 B1 | 9/2002 | Cho |
| 6,456,245 B1 | 9/2002 | Crawford |
| 6,457,346 B1 | 10/2002 | Kline-Schoder et al. |
| 6,463,785 B1 | 10/2002 | Kline-Schoder et al. |
| 6,467,331 B1 | 10/2002 | Kline-Schoder et al. |
| 6,468,242 B1 | 10/2002 | Wilson et al. |
| 6,475,178 B1 | 11/2002 | Krajewski |
| 6,481,980 B1 | 11/2002 | Vandlik |
| 6,482,158 B2 | 11/2002 | Mault |
| 6,482,185 B1 | 11/2002 | Hartmann |
| 6,485,263 B1 | 11/2002 | Bryant et al. |
| 6,485,418 B2 | 11/2002 | Yasushi et al. |
| 6,485,465 B2 | 11/2002 | Moberg et al. |
| 6,487,916 B1 | 12/2002 | Gomm et al. |
| 6,489,896 B1 | 12/2002 | Platt |
| 6,494,694 B2 | 12/2002 | Lawless et al. |
| 6,494,831 B1 | 12/2002 | Koritzinsky |
| 6,497,680 B1 | 12/2002 | Holst et al. |
| 6,503,221 B1 | 1/2003 | Briggs |
| 6,512,944 B1 | 1/2003 | Kovtun et al. |
| 6,516,667 B1 | 2/2003 | Broad et al. |
| 6,517,482 B1 | 2/2003 | Elden et al. |
| 6,519,569 B1 | 2/2003 | White et al. |
| 6,529,751 B1 | 3/2003 | Van Driel et al. |
| 6,531,708 B1 | 3/2003 | Malmstrom |
| 6,539,315 B1 | 3/2003 | Adams et al. |
| D473,238 S | 4/2003 | Cockerill |
| 6,540,672 B1 | 4/2003 | Simonsen et al. |
| 6,544,212 B2 | 4/2003 | Galley et al. |
| 6,544,228 B1 | 4/2003 | Heitmeier |
| 6,558,125 B1 | 5/2003 | Futterknecht |
| 6,558,351 B1 | 5/2003 | Steil et al. |
| 6,562,012 B1 | 5/2003 | Brown et al. |
| 6,564,825 B2 | 5/2003 | Lowery et al. |
| 6,565,509 B1 | 5/2003 | Say et al. |
| 6,568,416 B2 | 5/2003 | Tucker et al. |
| 6,572,542 B1 | 6/2003 | Houben et al. |

(56) References Cited

U.S. PATENT DOCUMENTS

| | | |
|---|---|---|
| 6,572,545 B2 | 6/2003 | Knobbe et al. |
| 6,572,576 B2 | 6/2003 | Brugger et al. |
| 6,578,422 B2 | 6/2003 | Lam et al. |
| 6,578,435 B2 | 6/2003 | Gould et al. |
| 6,581,117 B1 | 6/2003 | Klein et al. |
| RE38,189 E | 7/2003 | Walker et al. |
| 6,585,675 B1 | 7/2003 | O'Mahony et al. |
| 6,589,229 B1 | 7/2003 | Connelly et al. |
| 6,589,792 B1 | 7/2003 | Malachowski |
| 6,599,281 B1 | 7/2003 | Struys et al. |
| 6,599,282 B2 | 7/2003 | Burko |
| 6,602,191 B2 | 8/2003 | Quy |
| 6,605,072 B2 | 8/2003 | Struys et al. |
| 6,606,047 B1 | 8/2003 | Börjesson et al. |
| 6,609,047 B1 | 8/2003 | Lipps |
| 6,615,674 B2 | 9/2003 | Ohnishi |
| 6,616,633 B1 | 9/2003 | Butterfield et al. |
| 6,617,564 B2 | 9/2003 | Ockerse et al. |
| 6,618,916 B1 | 9/2003 | Eberle et al. |
| 6,622,542 B2 | 9/2003 | Derek |
| 6,622,561 B2 | 9/2003 | Lam et al. |
| D481,121 S | 10/2003 | Evans |
| 6,629,449 B1 | 10/2003 | Kline-Schoder et al. |
| 6,634,233 B2 | 10/2003 | He |
| 6,640,246 B1 | 10/2003 | Gardy, Jr. et al. |
| 6,641,533 B2 | 11/2003 | Causey, III et al. |
| 6,641,541 B1 | 11/2003 | Lovett et al. |
| 6,648,861 B2 | 11/2003 | Platt et al. |
| 6,652,455 B1 | 11/2003 | Kocher |
| 6,653,937 B2 | 11/2003 | Nelson et al. |
| 6,659,980 B2 | 12/2003 | Moberg et al. |
| D485,356 S | 1/2004 | Evans |
| 6,685,668 B1 | 2/2004 | Cho et al. |
| 6,685,678 B2 | 2/2004 | Evans et al. |
| 6,689,069 B2 | 2/2004 | Bratteli et al. |
| 6,689,091 B2 | 2/2004 | Bui et al. |
| 6,692,241 B2 | 2/2004 | Watanabe et al. |
| D487,574 S | 3/2004 | Glaser |
| 6,716,004 B2 | 4/2004 | Vandlik |
| 6,719,535 B2 | 4/2004 | Rakestraw et al. |
| 6,721,582 B2 | 4/2004 | Trepagnier et al. |
| 6,722,211 B1 | 4/2004 | Ciobanu et al. |
| 6,725,200 B1 | 4/2004 | Rost |
| 6,725,721 B2 | 4/2004 | Venczel |
| 6,731,989 B2 | 5/2004 | Engleson et al. |
| 6,732,595 B2 | 5/2004 | Lynnworth |
| 6,738,052 B1 | 5/2004 | Manke et al. |
| 6,740,072 B2 | 5/2004 | Starkweather et al. |
| 6,741,212 B2 | 5/2004 | Kralovec et al. |
| 6,748,808 B2 | 6/2004 | Lam et al. |
| 6,749,403 B2 | 6/2004 | Bryant et al. |
| 6,752,787 B1 | 6/2004 | Causey, III et al. |
| 6,753,842 B1 | 6/2004 | Williams et al. |
| 6,759,007 B1 | 7/2004 | Westberg |
| 6,760,643 B2 | 7/2004 | Lipps |
| 6,768,920 B2 | 7/2004 | Lange |
| 6,773,412 B2 | 8/2004 | O'Mahony |
| 6,780,156 B2 | 8/2004 | Haueter et al. |
| 6,783,328 B2 | 8/2004 | Lucke et al. |
| 6,785,573 B2 | 8/2004 | Kovtun et al. |
| 6,786,885 B2 | 9/2004 | Hochman et al. |
| 6,789,426 B2 | 9/2004 | Yaralioglu et al. |
| 6,790,198 B1 | 9/2004 | White et al. |
| 6,793,625 B2 | 9/2004 | Cavallaro et al. |
| 6,801,227 B2 | 10/2004 | Bocionek et al. |
| 6,805,671 B2 | 10/2004 | Stergiopoulos et al. |
| 6,807,965 B1 | 10/2004 | Hickle |
| 6,809,653 B1 | 10/2004 | Mann et al. |
| 6,813,964 B1 | 11/2004 | Clark et al. |
| 6,814,547 B2 | 11/2004 | Childers |
| 6,824,528 B1 | 11/2004 | Faries |
| 6,830,558 B2 | 12/2004 | Flaherty et al. |
| 6,840,113 B2 | 1/2005 | Fukumura et al. |
| 6,846,161 B2 | 1/2005 | Kline |
| 6,852,094 B2 | 2/2005 | Beck |
| 6,852,104 B2 | 2/2005 | Blomquist |
| 6,854,338 B2 | 2/2005 | Khuri-Yakub et al. |
| 6,857,318 B1 | 2/2005 | Silber et al. |
| 6,869,425 B2 | 3/2005 | Briggs et al. |
| 6,873,268 B2 | 3/2005 | Lebel et al. |
| 6,883,376 B2 | 4/2005 | He |
| 6,885,881 B2 | 4/2005 | Leonhardt |
| 6,887,216 B2 | 5/2005 | Hochman et al. |
| 6,898,301 B2 | 5/2005 | Iwanaga |
| 6,907,361 B2 | 6/2005 | Molenaar |
| 6,907,792 B2 | 6/2005 | Ohnishi |
| 6,915,170 B2 | 7/2005 | Engleson et al. |
| 6,920,795 B2 | 7/2005 | Bischoff et al. |
| 6,923,763 B1 | 8/2005 | Kovatchev et al. |
| 6,928,338 B1 | 8/2005 | Buchser et al. |
| 6,929,619 B2 | 8/2005 | Fago et al. |
| 6,929,751 B2 | 8/2005 | Bowman |
| 6,932,114 B2 | 8/2005 | Sparks |
| 6,932,796 B2 | 8/2005 | Sage et al. |
| 6,935,192 B2 | 8/2005 | Sobek et al. |
| 6,936,029 B2 | 8/2005 | Mann et al. |
| 6,941,005 B2 | 9/2005 | Lary et al. |
| 6,942,636 B2 | 9/2005 | Holst et al. |
| 6,945,954 B2 | 9/2005 | Hochman et al. |
| 6,958,705 B2 | 10/2005 | Lebel et al. |
| 6,964,204 B2 | 11/2005 | Clark et al. |
| 6,973,374 B2 | 12/2005 | Ader |
| 6,974,437 B2 | 12/2005 | Lebel et al. |
| 6,975,922 B2 | 12/2005 | Duncan et al. |
| 6,978,779 B2 | 12/2005 | Haveri et al. |
| 6,979,326 B2 | 12/2005 | Mann et al. |
| 6,981,960 B2 | 1/2006 | Cho et al. |
| 6,984,218 B2 | 1/2006 | Nayak et al. |
| 6,985,768 B2 | 1/2006 | Hemming et al. |
| 6,985,870 B2 | 1/2006 | Martucci et al. |
| 6,986,347 B2 | 1/2006 | Hickle |
| 6,986,753 B2 | 1/2006 | Bui |
| 6,997,905 B2 | 2/2006 | Gillespie, Jr. et al. |
| 6,997,920 B2 | 2/2006 | Mann et al. |
| 7,006,005 B2 | 2/2006 | Nazarian et al. |
| 7,017,623 B2 | 3/2006 | Tribble et al. |
| 7,021,148 B2 | 4/2006 | Kuhn |
| 7,025,743 B2 | 4/2006 | Mann et al. |
| 7,029,455 B2 | 4/2006 | Flaherty |
| 7,029,456 B2 | 4/2006 | Ware et al. |
| 7,059,184 B2 | 6/2006 | Kanouda et al. |
| 7,060,059 B2 | 6/2006 | Keith et al. |
| 7,069,793 B2 | 7/2006 | Ishikawa et al. |
| 7,072,725 B2 | 7/2006 | Bristol et al. |
| 7,074,209 B2 | 7/2006 | Evans et al. |
| 7,080,557 B2 | 7/2006 | Adnan |
| 7,082,843 B2 | 8/2006 | Clark et al. |
| 7,087,444 B2 | 8/2006 | Wong et al. |
| 7,092,796 B2 | 8/2006 | Vanderveen |
| 7,092,797 B2 | 8/2006 | Gaines et al. |
| 7,093,502 B2 | 8/2006 | Kupnik et al. |
| 7,096,729 B2 | 8/2006 | Repko et al. |
| 7,103,419 B2 | 9/2006 | Engleson et al. |
| 7,104,763 B2 | 9/2006 | Bouton et al. |
| 7,104,769 B2 | 9/2006 | Davis |
| 7,108,680 B2 | 9/2006 | Rohr et al. |
| 7,109,878 B2 | 9/2006 | Mann et al. |
| 7,115,113 B2 | 10/2006 | Evans et al. |
| 7,117,041 B2 | 10/2006 | Engleson et al. |
| 7,137,964 B2 | 11/2006 | Flaherty |
| 7,141,037 B2 | 11/2006 | Butterfield et al. |
| 7,152,490 B1 | 12/2006 | Freund, Jr. et al. |
| 7,154,397 B2 | 12/2006 | Zerhusen et al. |
| 7,161,488 B2 | 1/2007 | Frasch |
| 7,162,290 B1 | 1/2007 | Levin |
| 7,162,927 B1 | 1/2007 | Selvan et al. |
| 7,171,277 B2 | 1/2007 | Engleson et al. |
| 7,171,992 B2 | 2/2007 | DiGianfilippo et al. |
| 7,174,789 B2 | 2/2007 | Orr et al. |
| 7,185,288 B2 | 2/2007 | McKeever |
| 7,197,943 B2 | 4/2007 | Lee et al. |
| 7,201,734 B2 | 4/2007 | Hickle |
| 7,204,823 B2 | 4/2007 | Estes et al. |
| 7,206,715 B2 | 4/2007 | Vanderveen et al. |

(56) References Cited

U.S. PATENT DOCUMENTS

| | | |
|---|---|---|
| 7,213,009 B2 | 5/2007 | Pestotnik |
| 7,220,240 B2 | 5/2007 | Struys et al. |
| 7,229,430 B2 | 6/2007 | Hickle et al. |
| 7,230,529 B2 | 6/2007 | Ketcherside |
| 7,232,430 B2 | 6/2007 | Carlisle |
| 7,238,164 B2 | 7/2007 | Childers et al. |
| 7,247,154 B2 | 7/2007 | Hickle |
| 7,253,779 B2 | 8/2007 | Greer et al. |
| 7,254,425 B2 | 8/2007 | Lowery et al. |
| 7,258,534 B2 | 8/2007 | Fathallah et al. |
| 7,267,664 B2 | 9/2007 | Rizzo |
| 7,267,665 B2 | 9/2007 | Steil et al. |
| 7,272,529 B2 | 9/2007 | Hogan et al. |
| 7,278,983 B2 | 10/2007 | Ireland et al. |
| 7,291,123 B2 | 11/2007 | Baraldi et al. |
| 7,293,461 B1 | 11/2007 | Girndt |
| 7,294,109 B2 | 11/2007 | Lovett et al. |
| 7,296,482 B2 | 11/2007 | Schaffer et al. |
| 7,300,418 B2 | 11/2007 | Zaleski |
| 7,305,883 B2 | 12/2007 | Khuri-Yakub et al. |
| 7,327,273 B2 | 2/2008 | Hung et al. |
| D563,986 S | 3/2008 | Lettau |
| 7,338,470 B2 | 3/2008 | Katz |
| 7,343,224 B2 | 3/2008 | DiGianfilippo et al. |
| 7,347,836 B2 | 3/2008 | Peterson et al. |
| 7,347,854 B2 | 3/2008 | Shelton et al. |
| 7,354,420 B2 | 4/2008 | Steil et al. |
| 7,356,382 B2 | 4/2008 | Vanderveen |
| 7,360,999 B2 | 4/2008 | Nelson et al. |
| 7,364,562 B2 | 4/2008 | Braig et al. |
| 7,367,942 B2 | 5/2008 | Grage et al. |
| 7,369,948 B1 | 5/2008 | Ferenczi et al. |
| 7,384,410 B2 | 6/2008 | Eggers et al. |
| 7,397,166 B1 | 7/2008 | Morgan et al. |
| 7,398,183 B2 | 7/2008 | Holland et al. |
| 7,399,277 B2 | 7/2008 | Saidara et al. |
| 7,402,153 B2 | 7/2008 | Steil et al. |
| 7,402,154 B2 | 7/2008 | Mendez |
| 7,407,489 B2 | 8/2008 | Mendez |
| 7,414,534 B1 | 8/2008 | Kroll et al. |
| 7,415,895 B2 | 8/2008 | Kurisaki et al. |
| 7,426,443 B2 | 9/2008 | Simon |
| 7,430,675 B2 | 9/2008 | Lee et al. |
| 7,447,566 B2 | 11/2008 | Knauper et al. |
| 7,447,643 B1 | 11/2008 | Olson |
| 7,452,190 B2 | 11/2008 | Bouton et al. |
| 7,454,314 B2 | 11/2008 | Holland et al. |
| 7,471,994 B2 | 12/2008 | Ford et al. |
| 7,477,997 B2 | 1/2009 | Kaplit |
| 7,482,818 B2 | 1/2009 | Greenwald et al. |
| 7,483,756 B2 | 1/2009 | Engleson et al. |
| 7,490,021 B2 | 2/2009 | Holland et al. |
| 7,491,187 B2 | 2/2009 | Van Den Berghe et al. |
| 7,503,903 B2 | 3/2009 | Carlisle et al. |
| 7,517,332 B2 | 4/2009 | Tonelli et al. |
| 7,523,401 B1 | 4/2009 | Aldridge |
| D593,125 S | 5/2009 | Danton |
| 7,545,075 B2 | 6/2009 | Huang et al. |
| D596,195 S | 7/2009 | Wall |
| 7,556,616 B2 | 7/2009 | Fathallah et al. |
| 7,561,986 B2 | 7/2009 | Vanderveen et al. |
| 7,571,024 B2 | 8/2009 | Duncan et al. |
| 7,605,730 B2 | 10/2009 | Tomioka et al. |
| 7,614,310 B2 | 11/2009 | Konzelmann |
| 7,645,258 B2 | 1/2010 | White et al. |
| 7,654,127 B2 | 2/2010 | Krulevitch et al. |
| 7,657,443 B2 | 2/2010 | Crass |
| 7,668,731 B2 | 2/2010 | Martucci et al. |
| 7,678,048 B1 | 3/2010 | Urbano et al. |
| 7,693,697 B2 | 4/2010 | Westenskow et al. |
| 7,699,806 B2 | 4/2010 | Ware et al. |
| 7,705,727 B2 | 4/2010 | Pestotnik |
| D617,807 S | 6/2010 | Christie |
| D621,845 S | 8/2010 | Anzures |
| 7,766,873 B2 | 8/2010 | Moberg et al. |
| 7,775,126 B2 | 8/2010 | Eckhardt |
| 7,775,127 B2 | 8/2010 | Wade |
| 7,785,284 B2 | 8/2010 | Baralsi et al. |
| 7,785,313 B2 | 8/2010 | Mastrototaro |
| 7,786,909 B2 | 8/2010 | Udupa et al. |
| 7,806,886 B2 | 10/2010 | Kanderian, Jr. et al. |
| 7,826,981 B2 | 11/2010 | Goode, Jr. et al. |
| 7,847,276 B2 | 12/2010 | Carlisle |
| 7,860,583 B2 | 12/2010 | Condurso et al. |
| 7,871,394 B2 | 1/2011 | Halbert et al. |
| 7,876,443 B2 | 1/2011 | Bernacki |
| 7,895,053 B2 | 2/2011 | Holland et al. |
| 7,895,882 B2 | 3/2011 | Carlisle |
| 7,896,834 B2 | 3/2011 | Smisson, III |
| 7,896,842 B2 | 3/2011 | Palmroos et al. |
| 7,905,710 B2 | 3/2011 | Wang et al. |
| 7,933,780 B2 | 4/2011 | de la Huerga |
| 7,938,817 B2 | 5/2011 | Gelfand et al. |
| 7,945,452 B2 | 5/2011 | Fathallah et al. |
| D642,195 S | 7/2011 | Marks |
| 7,976,508 B2 | 7/2011 | Hoag |
| 7,981,073 B2 | 7/2011 | Mollstam |
| 7,981,082 B2 | 7/2011 | Wang et al. |
| 7,998,134 B2 | 8/2011 | Fangrow |
| 8,002,736 B2 | 8/2011 | Patrick et al. |
| 8,034,020 B2 | 10/2011 | Dewey |
| 8,038,593 B2 | 10/2011 | Friedman et al. |
| 8,065,161 B2 | 11/2011 | Howard et al. |
| 8,067,760 B2 | 11/2011 | Carlisle |
| 8,075,514 B2 | 12/2011 | Butterfield et al. |
| 8,075,546 B2 | 12/2011 | Carlisle et al. |
| 8,078,983 B2 | 12/2011 | Davis et al. |
| 8,121,857 B2 | 2/2012 | Galasso et al. |
| 8,149,131 B2 | 4/2012 | Blomquist |
| D659,709 S | 5/2012 | Eby |
| 8,175,668 B1 | 5/2012 | Nabutovsky et al. |
| 8,177,739 B2 | 5/2012 | Cartledge et al. |
| 8,180,440 B2 | 5/2012 | McCombie et al. |
| 8,185,322 B2 | 5/2012 | Schroeder et al. |
| 8,197,444 B1 | 6/2012 | Bazargan et al. |
| 8,219,413 B2 | 7/2012 | Martinez et al. |
| 8,221,395 B2 | 7/2012 | Shelton et al. |
| 8,226,597 B2 | 7/2012 | Jacobson et al. |
| 8,231,578 B2 | 7/2012 | Fathallah et al. |
| 8,234,128 B2 | 7/2012 | Martucci et al. |
| D667,452 S | 9/2012 | Wujcik |
| D667,840 S | 9/2012 | Anzures |
| 8,271,106 B2 | 9/2012 | Wehba et al. |
| 8,287,514 B2 | 10/2012 | Miller et al. |
| 8,291,337 B2 | 10/2012 | Gannin et al. |
| 8,313,308 B2 | 11/2012 | Lawless et al. |
| 8,317,698 B2 | 11/2012 | Lowery |
| 8,317,750 B2 | 11/2012 | Ware et al. |
| 8,317,752 B2 | 11/2012 | Cozmi et al. |
| 8,318,094 B1 | 11/2012 | Bayandorian et al. |
| 8,340,792 B2 | 12/2012 | Condurso et al. |
| 8,347,731 B2 | 1/2013 | Genosar |
| 8,359,338 B2 | 1/2013 | Butterfield et al. |
| 8,361,021 B2 | 1/2013 | Wang et al. |
| 8,378,837 B2 | 2/2013 | Wang et al. |
| 8,388,598 B2 | 3/2013 | Steinkogler |
| 8,398,616 B2 | 3/2013 | Budiman |
| 8,403,908 B2 | 3/2013 | Jacobson et al. |
| D679,727 S | 4/2013 | Abratowski |
| 8,409,164 B2 | 4/2013 | Fangrow |
| 8,449,524 B2 | 5/2013 | Braig et al. |
| 8,469,942 B2 | 6/2013 | Kow et al. |
| 8,477,307 B1 | 7/2013 | Yufa et al. |
| 8,494,879 B2 | 7/2013 | Davis et al. |
| 8,504,179 B2 | 8/2013 | Blomquist |
| 8,506,552 B2 | 8/2013 | Rebours |
| 8,517,990 B2 | 8/2013 | Teel et al. |
| 8,518,021 B2 | 8/2013 | Stewart et al. |
| 8,522,832 B2 | 9/2013 | Lopez et al. |
| 8,523,797 B2 | 9/2013 | Lowery et al. |
| 8,539,812 B2 | 9/2013 | Stringham et al. |
| 8,543,416 B2 | 9/2013 | Palmroos et al. |
| 8,577,692 B2 | 11/2013 | Silkaitis et al. |
| 8,622,990 B2 | 1/2014 | Estes et al. |

(56) References Cited

U.S. PATENT DOCUMENTS

| | | |
|---|---|---|
| 8,630,722 B2 | 1/2014 | Condurso et al. |
| 8,665,214 B2 | 3/2014 | Forutanpour et al. |
| 8,666,769 B2 | 3/2014 | Butler et al. |
| 8,700,421 B2 | 4/2014 | Feng et al. |
| 8,706,233 B2 | 4/2014 | Su et al. |
| D705,260 S | 5/2014 | Gerssen |
| 8,721,584 B2 | 5/2014 | Braithwaite et al. |
| 8,728,020 B2 | 5/2014 | Caleffi et al. |
| D706,294 S | 6/2014 | Jewitt |
| 8,758,306 B2 | 6/2014 | Lopez et al. |
| 8,761,906 B2 | 6/2014 | Condurso et al. |
| D709,091 S | 7/2014 | Kwon |
| 8,768,719 B2 | 7/2014 | Wehba et al. |
| 8,771,251 B2 | 7/2014 | Ruchti et al. |
| 8,792,981 B2 | 7/2014 | Yudovsky et al. |
| D711,916 S | 8/2014 | Matas |
| D712,926 S | 9/2014 | Meegan |
| D713,417 S | 9/2014 | Daniel |
| D713,418 S | 9/2014 | Yang |
| D713,420 S | 9/2014 | Dallmeyer |
| 8,821,432 B2 | 9/2014 | Unverdorben |
| 8,823,382 B2 | 9/2014 | Rondoni et al. |
| 8,857,269 B2 | 10/2014 | Johnson et al. |
| 8,858,185 B2 | 10/2014 | Johnson et al. |
| 8,905,965 B2 | 12/2014 | Mandro et al. |
| D721,385 S | 1/2015 | Barling |
| 8,948,734 B2 | 2/2015 | Vaglio |
| 8,964,185 B1 | 2/2015 | Luo et al. |
| 9,005,150 B2 | 4/2015 | Ware et al. |
| 9,026,370 B2 | 5/2015 | Rubalcaba et al. |
| 9,084,855 B2 | 7/2015 | Ware et al. |
| 9,114,217 B2 | 8/2015 | Sur et al. |
| 9,134,735 B2 | 9/2015 | Lowery et al. |
| 9,134,736 B2 | 9/2015 | Lowery et al. |
| 9,138,526 B2 | 9/2015 | Ware et al. |
| D742,413 S | 11/2015 | Torres |
| D742,414 S | 11/2015 | Brunner |
| D742,415 S | 11/2015 | Cahill |
| D743,414 S | 11/2015 | Uno |
| 9,190,010 B2 | 11/2015 | Vik et al. |
| D747,339 S | 1/2016 | Cohen |
| 9,240,002 B2 | 1/2016 | Hume et al. |
| D750,099 S | 2/2016 | Kadosh |
| 9,272,089 B2 | 3/2016 | Jacobson et al. |
| 9,316,216 B1 | 4/2016 | Cook et al. |
| D757,099 S | 5/2016 | Seo |
| 9,333,291 B2 | 5/2016 | Jacobson et al. |
| D758,379 S | 6/2016 | Kadosh |
| D759,036 S | 6/2016 | Evanes |
| D760,238 S | 6/2016 | Suarez |
| D760,248 S | 6/2016 | Smith |
| D760,295 S | 6/2016 | Smith |
| D760,788 S | 7/2016 | Cho |
| D761,820 S | 7/2016 | Lee |
| D762,238 S | 7/2016 | Day |
| 9,381,296 B2 | 7/2016 | Arrizza et al. |
| 9,393,362 B2 | 7/2016 | Cozmi et al. |
| D764,538 S | 8/2016 | Lee |
| 9,468,718 B2 | 10/2016 | Hung et al. |
| 9,498,583 B2 | 11/2016 | Sur et al. |
| D773,519 S | 12/2016 | Hurley |
| D777,205 S | 1/2017 | Orr |
| 9,545,475 B2 | 1/2017 | Borges et al. |
| 9,545,476 B2 | 1/2017 | Qi et al. |
| D779,537 S | 2/2017 | Wingate-Whyte |
| D781,874 S | 3/2017 | Dunn |
| D782,535 S | 3/2017 | Menz |
| 9,707,341 B2 | 7/2017 | Dumas, III et al. |
| 9,764,087 B2 | 9/2017 | Peterfreund et al. |
| 9,773,330 B1 | 9/2017 | Douglas |
| D803,881 S | 11/2017 | Hurley |
| D806,109 S | 12/2017 | Day |
| 9,852,265 B1 | 12/2017 | Treacy et al. |
| D809,006 S | 1/2018 | Mehta |
| 9,883,987 B2 | 2/2018 | Lopez et al. |
| 9,943,269 B2 | 4/2018 | Muhsin et al. |
| 9,995,611 B2 | 6/2018 | Ruchti et al. |
| 10,002,496 B2 | 6/2018 | Humphrey |
| 10,022,498 B2 | 7/2018 | Ruchti et al. |
| 10,046,112 B2 | 8/2018 | Oruklu et al. |
| D827,665 S | 9/2018 | Segars |
| 10,089,055 B1 | 10/2018 | Fryman |
| 10,099,009 B1 | 10/2018 | Anderson et al. |
| 10,166,328 B2 | 1/2019 | Oruklu et al. |
| 10,241,626 B2 | 3/2019 | Miyazawa |
| 10,297,350 B2 | 5/2019 | Duke et al. |
| 10,342,917 B2 | 7/2019 | Shubinsky et al. |
| 10,430,761 B2 | 10/2019 | Hume et al. |
| D865,777 S | 11/2019 | Kovács |
| 10,463,788 B2 | 11/2019 | Day |
| 10,549,248 B2 | 2/2020 | Brown et al. |
| 10,578,474 B2 | 3/2020 | Ruchti et al. |
| 10,596,316 B2 | 3/2020 | Dumas, III et al. |
| 10,635,784 B2 | 4/2020 | Rubalcaba, Jr. et al. |
| 10,656,894 B2 | 5/2020 | Fryman |
| 10,682,102 B2 | 6/2020 | Declerck |
| 10,709,885 B2 | 7/2020 | Janders et al. |
| D898,055 S | 10/2020 | Connolly |
| 10,850,024 B2 | 12/2020 | Day et al. |
| 10,874,793 B2 | 12/2020 | Oruklu et al. |
| 11,004,035 B2 | 5/2021 | Hume et al. |
| 11,007,119 B2 | 5/2021 | Lopez et al. |
| D922,432 S | 6/2021 | Kataoka et al. |
| D923,050 S | 6/2021 | Kataoka et al. |
| 11,029,911 B2 | 6/2021 | Fryman |
| D926,201 S | 7/2021 | Bryant et al. |
| D926,224 S | 7/2021 | Hummel |
| D928,813 S | 8/2021 | Nurutdinov et al. |
| D928,840 S | 8/2021 | Amit et al. |
| 11,090,431 B2 | 8/2021 | Dumas, III et al. |
| D931,884 S | 9/2021 | Bryant et al. |
| D931,892 S | 9/2021 | Nurutdinov |
| D934,282 S | 10/2021 | Clymer |
| 11,135,360 B1 | 10/2021 | Jacobson et al. |
| 11,219,715 B2 | 1/2022 | Gray et al. |
| 11,246,985 B2 | 2/2022 | Gylland et al. |
| D946,608 S | 3/2022 | Higuchi |
| 11,278,671 B2 | 3/2022 | Cavendish, Jr. et al. |
| 11,298,456 B2 | 4/2022 | Shubinsky et al. |
| 11,324,888 B2 | 5/2022 | Shubinsky et al. |
| 11,344,668 B2 | 5/2022 | Sileika et al. |
| 11,344,673 B2 | 5/2022 | Lindo et al. |
| 11,376,361 B2 | 7/2022 | Ruchti et al. |
| 11,378,430 B2 | 7/2022 | Ruchti et al. |
| 11,395,875 B2 | 7/2022 | Rubalcaba, Jr. et al. |
| 11,433,177 B2 | 9/2022 | Oruklu et al. |
| 11,439,570 B2 | 9/2022 | Lopez et al. |
| 11,596,737 B2 | 3/2023 | Dumas, III et al. |
| 11,599,854 B2 | 3/2023 | Hume et al. |
| 11,623,042 B2 | 4/2023 | Day |
| 11,868,161 B2 | 1/2024 | Fryman |
| 11,883,361 B2 | 1/2024 | Janssen |
| D1,017,633 S | 3/2024 | Chung |
| D1,018,593 S | 3/2024 | Chiah |
| 11,933,650 B2 | 3/2024 | Ruchti et al. |
| D1,021,917 S | 4/2024 | Ceniceroz |
| D1,023,027 S | 4/2024 | Slettnes |
| D1,024,096 S | 4/2024 | Zhong |
| 11,972,395 B2 | 4/2024 | Hume et al. |
| D1,027,974 S | 5/2024 | Correy |
| 12,048,831 B2 | 7/2024 | Oruklu et al. |
| 12,059,551 B2 | 8/2024 | Dumas, III et al. |
| 12,076,531 B2 | 9/2024 | Shubinsky et al. |
| 12,083,310 B2 | 9/2024 | Shubinsky et al. |
| 2001/0007636 A1 | 7/2001 | Butterfield |
| 2001/0014769 A1 | 8/2001 | Bufe et al. |
| 2001/0015099 A1 | 8/2001 | Blaine |
| 2001/0016056 A1 | 8/2001 | Westphal et al. |
| 2001/0032099 A1 | 10/2001 | Joao |
| 2001/0037060 A1 | 11/2001 | Thompson et al. |
| 2001/0041869 A1 | 11/2001 | Causey et al. |
| 2001/0044731 A1 | 11/2001 | Coffman et al. |
| 2002/0003892 A1 | 1/2002 | Iwanaga |
| 2002/0007116 A1 | 1/2002 | Zatezalo et al. |

(56) References Cited

U.S. PATENT DOCUMENTS

| | | |
|---|---|---|
| 2002/0013545 A1 | 1/2002 | Soltanpour et al. |
| 2002/0013551 A1 | 1/2002 | Zaitsu et al. |
| 2002/0015018 A1 | 2/2002 | Shimazu et al. |
| 2002/0018720 A1 | 2/2002 | Carlisle et al. |
| 2002/0029776 A1 | 3/2002 | Blomquist |
| 2002/0031838 A1 | 3/2002 | Meinhart et al. |
| 2002/0032583 A1 | 3/2002 | Joao |
| 2002/0040208 A1 | 4/2002 | Flaherty et al. |
| 2002/0044059 A1 | 4/2002 | Reeder et al. |
| 2002/0045806 A1 | 4/2002 | Baker, Jr. et al. |
| 2002/0082728 A1 | 6/2002 | Mueller et al. |
| 2002/0083771 A1 | 7/2002 | Khuri-Yakub et al. |
| 2002/0085952 A1 | 7/2002 | Ellingboe et al. |
| 2002/0087115 A1 | 7/2002 | Hartlaub |
| 2002/0093641 A1 | 7/2002 | Ortyn et al. |
| 2002/0095486 A1 | 7/2002 | Bahl |
| 2002/0099282 A1 | 7/2002 | Knobbe et al. |
| 2002/0099334 A1 | 7/2002 | Hanson et al. |
| 2002/0143580 A1 | 10/2002 | Bristol et al. |
| 2002/0147389 A1 | 10/2002 | Cavallaro et al. |
| 2002/0152239 A1 | 10/2002 | Bautista-Lloyd et al. |
| 2002/0158919 A1 | 10/2002 | Nacey |
| 2002/0168278 A1 | 11/2002 | Jeon et al. |
| 2002/0173703 A1 | 11/2002 | Lebel et al. |
| 2002/0183693 A1 | 12/2002 | Peterson et al. |
| 2003/0009244 A1 | 1/2003 | Engleson |
| 2003/0013959 A1 | 1/2003 | Grunwald et al. |
| 2003/0018289 A1 | 1/2003 | Ng et al. |
| 2003/0018308 A1 | 1/2003 | Tsai |
| 2003/0025602 A1 | 2/2003 | Medema et al. |
| 2003/0028082 A1 | 2/2003 | Thompson |
| 2003/0030001 A1 | 2/2003 | Cooper et al. |
| 2003/0045840 A1 | 3/2003 | Burko |
| 2003/0050621 A1 | 3/2003 | Lebel et al. |
| 2003/0060688 A1 | 3/2003 | Ciarniello et al. |
| 2003/0060765 A1 | 3/2003 | Campbell et al. |
| 2003/0065537 A1 | 4/2003 | Evans |
| 2003/0065589 A1 | 4/2003 | Giacchetti |
| 2003/0073954 A1 | 4/2003 | Moberg et al. |
| 2003/0079746 A1 | 5/2003 | Hickle |
| 2003/0083583 A1 | 5/2003 | Kovtun et al. |
| 2003/0091442 A1 | 5/2003 | Bush et al. |
| 2003/0104982 A1 | 6/2003 | Wittmann et al. |
| 2003/0106553 A1 | 6/2003 | Vanderveen |
| 2003/0125662 A1 | 7/2003 | Bui |
| 2003/0130616 A1 | 7/2003 | Steil |
| 2003/0135087 A1 | 7/2003 | Hickle et al. |
| 2003/0136193 A1 | 7/2003 | Fujimoto |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158508 A1 | 8/2003 | DiGianfilippo |
| 2003/0159741 A1 | 8/2003 | Sparks |
| 2003/0160683 A1 | 8/2003 | Blomquist |
| 2003/0163789 A1 | 8/2003 | Blomquist |
| 2003/0173408 A1 | 9/2003 | Mosher, Jr. et al. |
| 2003/0186833 A1 | 10/2003 | Huff et al. |
| 2003/0187338 A1 | 10/2003 | Say et al. |
| 2003/0200116 A1 | 10/2003 | Forrester |
| 2003/0204274 A1 | 10/2003 | Ullestad et al. |
| 2003/0204416 A1 | 10/2003 | Acharya |
| 2003/0212364 A1 | 11/2003 | Mann et al. |
| 2003/0212379 A1 | 11/2003 | Bylund et al. |
| 2003/0216682 A1 | 11/2003 | Junker |
| 2003/0217962 A1 | 11/2003 | Childers et al. |
| 2003/0233071 A1 | 12/2003 | Gillespie, Jr. et al. |
| 2004/0030277 A1 | 2/2004 | O'Mahony et al. |
| 2004/0047736 A1 | 3/2004 | Nose et al. |
| 2004/0057226 A1 | 3/2004 | Berthou et al. |
| 2004/0064342 A1 | 4/2004 | Browne et al. |
| 2004/0073125 A1 | 4/2004 | Lovett et al. |
| 2004/0073161 A1 | 4/2004 | Tachibana |
| 2004/0077996 A1 | 4/2004 | Jasperson et al. |
| 2004/0082908 A1 | 4/2004 | Whitehurst |
| 2004/0082918 A1 | 4/2004 | Evans et al. |
| 2004/0104271 A1 | 6/2004 | Martucci et al. |
| 2004/0119753 A1 | 6/2004 | Zencke |
| 2004/0120825 A1 | 6/2004 | Bouton et al. |
| 2004/0128162 A1 | 7/2004 | Schlotterbeck et al. |
| 2004/0128163 A1 | 7/2004 | Goodman et al. |
| 2004/0130573 A1 | 7/2004 | Konuma |
| 2004/0133166 A1 | 7/2004 | Moberg et al. |
| 2004/0145114 A1 | 7/2004 | Ippolito et al. |
| 2004/0147034 A1 | 7/2004 | Gore et al. |
| 2004/0149823 A1 | 8/2004 | Aptekar |
| 2004/0152970 A1 | 8/2004 | Hunter et al. |
| 2004/0158193 A1 | 8/2004 | Bui et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172289 A1 | 9/2004 | Kozic et al. |
| 2004/0172301 A1 | 9/2004 | Mihai et al. |
| 2004/0172302 A1 | 9/2004 | Martucci et al. |
| 2004/0176984 A1 | 9/2004 | White et al. |
| 2004/0181314 A1 | 9/2004 | Zaleski |
| 2004/0193025 A1 | 9/2004 | Steil et al. |
| 2004/0193325 A1 | 9/2004 | Bonderud |
| 2004/0193328 A1 | 9/2004 | Butterfield et al. |
| 2004/0204638 A1 | 10/2004 | Diab et al. |
| 2004/0204673 A1 | 10/2004 | Flaherty et al. |
| 2004/0220517 A1 | 11/2004 | Starkweather et al. |
| 2004/0225252 A1 | 11/2004 | Gillespie et al. |
| 2004/0225409 A1 | 11/2004 | Duncan et al. |
| 2004/0232219 A1 | 11/2004 | Fowler |
| 2004/0253123 A1 | 12/2004 | Xie et al. |
| 2004/0254434 A1 | 12/2004 | Goodnow et al. |
| 2004/0254513 A1 | 12/2004 | Shang et al. |
| 2005/0021006 A1 | 1/2005 | Tonnies |
| 2005/0021297 A1 | 1/2005 | Hartlaub |
| 2005/0022274 A1 | 1/2005 | Campbell et al. |
| 2005/0038680 A1 | 2/2005 | McMahon |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0075544 A1 | 4/2005 | Shapiro et al. |
| 2005/0096593 A1 | 5/2005 | Pope et al. |
| 2005/0099624 A1 | 5/2005 | Staehr |
| 2005/0107923 A1 | 5/2005 | Vanderveen |
| 2005/0108057 A1 | 5/2005 | Cohen et al. |
| 2005/0119597 A1 | 6/2005 | O'Mahony et al. |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0143864 A1 | 6/2005 | Blomquist |
| 2005/0145010 A1 | 7/2005 | Vanderveen et al. |
| 2005/0171503 A1 | 8/2005 | Van Den Berghe et al. |
| 2005/0171815 A1 | 8/2005 | Vanderveen |
| 2005/0177045 A1 | 8/2005 | Degertekin et al. |
| 2005/0177096 A1 | 8/2005 | Bollish et al. |
| 2005/0182306 A1 | 8/2005 | Sloan |
| 2005/0182355 A1 | 8/2005 | Bui |
| 2005/0182366 A1 | 8/2005 | Vogt et al. |
| 2005/0187515 A1 | 8/2005 | Varrichio et al. |
| 2005/0192529 A1 | 9/2005 | Butterfield et al. |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0197649 A1 | 9/2005 | Shelton et al. |
| 2005/0209563 A1 | 9/2005 | Hopping et al. |
| 2005/0209793 A1 | 9/2005 | Yamada |
| 2005/0224083 A1 | 10/2005 | Crass |
| 2005/0235732 A1 | 10/2005 | Rush |
| 2005/0238506 A1 | 10/2005 | Mescher et al. |
| 2005/0240305 A1 | 10/2005 | Bogash et al. |
| 2005/0273059 A1 | 12/2005 | Mernoe et al. |
| 2005/0277890 A1 | 12/2005 | Stewart et al. |
| 2005/0279419 A1 | 12/2005 | Tribble et al. |
| 2006/0002799 A1 | 1/2006 | Schann et al. |
| 2006/0009727 A1 | 1/2006 | O'Mahony et al. |

(56) References Cited

U.S. PATENT DOCUMENTS

| | | |
|---|---|---|
| 2006/0009734 A1 | 1/2006 | Martin |
| 2006/0042633 A1 | 3/2006 | Bishop et al. |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0064053 A1 | 3/2006 | Bollish et al. |
| 2006/0079768 A1 | 4/2006 | Small et al. |
| 2006/0079831 A1 | 4/2006 | Gilbert |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0116639 A1 | 6/2006 | Russell |
| 2006/0117856 A1 | 6/2006 | Orr et al. |
| 2006/0117867 A1 | 6/2006 | Froehlich et al. |
| 2006/0122867 A1 | 6/2006 | Eggers et al. |
| 2006/0135939 A1 | 6/2006 | Brown |
| 2006/0135940 A1 | 6/2006 | Joshi |
| 2006/0136095 A1 | 6/2006 | Rob et al. |
| 2006/0136271 A1 | 6/2006 | Eggers et al. |
| 2006/0140798 A1 | 6/2006 | Kutsuzawa |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0180916 A1 | 8/2006 | Wyland et al. |
| 2006/0181695 A1 | 8/2006 | Sage, Jr. |
| 2006/0187069 A1 | 8/2006 | Duan |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224140 A1 | 10/2006 | Junker |
| 2006/0224141 A1 | 10/2006 | Rush et al. |
| 2006/0224181 A1 | 10/2006 | McEwen et al. |
| 2006/0226088 A1 | 10/2006 | Robinson et al. |
| 2006/0226089 A1 | 10/2006 | Robinson et al. |
| 2006/0226090 A1 | 10/2006 | Robinson et al. |
| 2006/0229918 A1 | 10/2006 | Fotsch et al. |
| 2006/0235353 A1 | 10/2006 | Gelfand et al. |
| 2006/0255149 A1 | 11/2006 | Retter et al. |
| 2006/0258985 A1 | 11/2006 | Russell |
| 2006/0260416 A1 | 11/2006 | Sage et al. |
| 2006/0264895 A1 | 11/2006 | Flanders |
| 2006/0266128 A1 | 11/2006 | Clark et al. |
| 2006/0270971 A1 | 11/2006 | Gelfand et al. |
| 2006/0271286 A1 | 11/2006 | Rosenberg |
| 2006/0272421 A1 | 12/2006 | Frinak et al. |
| 2006/0275142 A1 | 12/2006 | Bouton et al. |
| 2007/0015972 A1 | 1/2007 | Wang et al. |
| 2007/0036511 A1 | 2/2007 | Lundquist et al. |
| 2007/0060796 A1 | 3/2007 | Kim |
| 2007/0060869 A1 | 3/2007 | Tolle et al. |
| 2007/0060871 A1 | 3/2007 | Istoc |
| 2007/0060872 A1 | 3/2007 | Hall et al. |
| 2007/0060874 A1 | 3/2007 | Nesbitt et al. |
| 2007/0062250 A1 | 3/2007 | Krulevitch et al. |
| 2007/0065363 A1 | 3/2007 | Dalal et al. |
| 2007/0078314 A1 | 4/2007 | Grounsell |
| 2007/0083152 A1 | 4/2007 | Williams, Jr. et al. |
| 2007/0084286 A1 | 4/2007 | Ajay et al. |
| 2007/0084288 A1 | 4/2007 | Thomas et al. |
| 2007/0088271 A1 | 4/2007 | Richards |
| 2007/0088333 A1 | 4/2007 | Levin et al. |
| 2007/0093753 A1 | 4/2007 | Krulevitcvh et al. |
| 2007/0094045 A1 | 4/2007 | Cobbs et al. |
| 2007/0094046 A1 | 4/2007 | Cobbs et al. |
| 2007/0100222 A1 | 5/2007 | Mastrototaro et al. |
| 2007/0100665 A1 | 5/2007 | Brown |
| 2007/0112298 A1 | 5/2007 | Mueller et al. |
| 2007/0118405 A1 | 5/2007 | Campbell et al. |
| 2007/0129618 A1 | 6/2007 | Goldberger et al. |
| 2007/0142822 A1 | 6/2007 | Remde |
| 2007/0156452 A1 | 7/2007 | Batch |
| 2007/0156456 A1 | 7/2007 | McGillin et al. |
| 2007/0179436 A1 | 8/2007 | Braig et al. |
| 2007/0180916 A1 | 8/2007 | Tian et al. |
| 2007/0191770 A1 | 8/2007 | Moberg et al. |
| 2007/0191817 A1 | 8/2007 | Martin |
| 2007/0197963 A1 | 8/2007 | Griffiths et al. |
| 2007/0214003 A1 | 9/2007 | Holland et al. |
| 2007/0215545 A1 | 9/2007 | Bissler et al. |
| 2007/0233035 A1 | 10/2007 | Wehba et al. |
| 2007/0233049 A1 | 10/2007 | Wehba et al. |
| 2007/0240497 A1 | 10/2007 | Robinson et al. |
| 2007/0250339 A1 | 10/2007 | Mallett et al. |
| 2007/0255250 A1 | 11/2007 | Moberg et al. |
| 2007/0257788 A1 | 11/2007 | Carlson |
| 2007/0267945 A1 | 11/2007 | Sudol |
| 2007/0270747 A1 | 11/2007 | Remde |
| 2007/0274843 A1 | 11/2007 | Vanderveen et al. |
| 2007/0289384 A1 | 12/2007 | Sakai et al. |
| 2008/0009684 A1 | 1/2008 | Corsetti et al. |
| 2008/0028868 A1 | 2/2008 | Konzelmann et al. |
| 2008/0033361 A1 | 2/2008 | Evans et al. |
| 2008/0039777 A1 | 2/2008 | Katz et al. |
| 2008/0048211 A1 | 2/2008 | Khuri-Yakub et al. |
| 2008/0058773 A1 | 3/2008 | John |
| 2008/0060448 A1 | 3/2008 | Wiest et al. |
| 2008/0065420 A1 | 3/2008 | Tirinato et al. |
| 2008/0071210 A1 | 3/2008 | Moubayed et al. |
| 2008/0071496 A1 | 3/2008 | Glascock |
| 2008/0071580 A1 | 3/2008 | Marcus et al. |
| 2008/0077116 A1 | 3/2008 | Dailey et al. |
| 2008/0086087 A1 | 4/2008 | Spohn et al. |
| 2008/0091466 A1 | 4/2008 | Butler et al. |
| 2008/0097288 A1 | 4/2008 | Levin et al. |
| 2008/0097289 A1 | 4/2008 | Steil et al. |
| 2008/0097317 A1 | 4/2008 | Alholm et al. |
| 2008/0098798 A1 | 5/2008 | Riley et al. |
| 2008/0119822 A1 | 5/2008 | Knauper |
| 2008/0125701 A1 | 5/2008 | Moberg et al. |
| 2008/0139907 A1 | 6/2008 | Rao et al. |
| 2008/0145249 A1 | 6/2008 | Smisson |
| 2008/0169044 A1 | 7/2008 | Osborne et al. |
| 2008/0172030 A1 | 7/2008 | Blomquist et al. |
| 2008/0177254 A1 | 7/2008 | Shelton et al. |
| 2008/0184784 A1 | 8/2008 | Dam |
| 2008/0188789 A1 | 8/2008 | Galavotti et al. |
| 2008/0188796 A1 | 8/2008 | Steil et al. |
| 2008/0208484 A1 | 8/2008 | Butterfield et al. |
| 2008/0214919 A1 | 9/2008 | Harmon et al. |
| 2008/0221521 A1 | 9/2008 | Getz et al. |
| 2008/0221522 A1 | 9/2008 | Moberg et al. |
| 2008/0262469 A1 | 10/2008 | Bristol et al. |
| 2008/0269663 A1 | 10/2008 | Arnold et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2009/0001908 A1 | 1/2009 | Shubinsky et al. |
| 2009/0005703 A1 | 1/2009 | Fasciano |
| 2009/0006061 A1 | 1/2009 | Thukral et al. |
| 2009/0006129 A1 | 1/2009 | Thukral |
| 2009/0006133 A1 | 1/2009 | Weinert |
| 2009/0015824 A1 | 1/2009 | Shubinsky et al. |
| 2009/0043171 A1 | 2/2009 | Rule |
| 2009/0054743 A1 | 2/2009 | Stewart |
| 2009/0054754 A1 | 2/2009 | McMahon et al. |
| 2009/0062727 A1 | 3/2009 | Woo |
| 2009/0069743 A1 | 3/2009 | Krishnamoorthy et al. |
| 2009/0077248 A1 | 3/2009 | Castellucci et al. |
| 2009/0082676 A1 | 3/2009 | Bennison |
| 2009/0088731 A1 | 4/2009 | Campbell et al. |
| 2009/0097029 A1 | 4/2009 | Tokhtuev et al. |
| 2009/0099866 A1 | 4/2009 | Newman |
| 2009/0105636 A1 | 4/2009 | Hayter et al. |
| 2009/0112155 A1 | 4/2009 | Zhao |
| 2009/0114037 A1 | 5/2009 | Smith |
| 2009/0119330 A1 | 5/2009 | Sampath et al. |
| 2009/0124963 A1 | 5/2009 | Hogard et al. |
| 2009/0124964 A1 | 5/2009 | Leach et al. |
| 2009/0126825 A1 | 5/2009 | Eliuk et al. |
| 2009/0131861 A1 | 5/2009 | Braig et al. |
| 2009/0135196 A1 | 5/2009 | Holland et al. |

(56) References Cited

U.S. PATENT DOCUMENTS

| | | |
|---|---|---|
| 2009/0143726 A1 | 6/2009 | Bouton et al. |
| 2009/0144025 A1 | 6/2009 | Bouton et al. |
| 2009/0144026 A1 | 6/2009 | Bouton et al. |
| 2009/0149743 A1 | 6/2009 | Barron et al. |
| 2009/0156922 A1 | 6/2009 | Goldberger et al. |
| 2009/0156975 A1 | 6/2009 | Robinson et al. |
| 2009/0177146 A1 | 7/2009 | Nesbitt et al. |
| 2009/0177188 A1 | 7/2009 | Steinkogler |
| 2009/0177248 A1 | 7/2009 | Roberts |
| 2009/0177769 A1 | 7/2009 | Roberts |
| 2009/0178485 A1 | 7/2009 | Thomas et al. |
| 2009/0183147 A1 | 7/2009 | Davis et al. |
| 2009/0192367 A1 | 7/2009 | Braig et al. |
| 2009/0198347 A1 | 8/2009 | Kirzinger |
| 2009/0205426 A1 | 8/2009 | Balschat et al. |
| 2009/0209938 A1 | 8/2009 | Aalto-Setala |
| 2009/0209945 A1 | 8/2009 | Lobl et al. |
| 2009/0212966 A1 | 8/2009 | Panduro |
| 2009/0221890 A1 | 9/2009 | Saffer et al. |
| 2009/0223294 A1 | 9/2009 | Thomas et al. |
| 2009/0227939 A1 | 9/2009 | Memoe et al. |
| 2009/0264720 A1 | 10/2009 | Torjman et al. |
| 2009/0270810 A1 | 10/2009 | DeBelser |
| 2009/0270833 A1 | 10/2009 | DeBelser |
| 2010/0022988 A1 | 1/2010 | Wochner |
| 2010/0036310 A1 | 2/2010 | Hillman |
| 2010/0056992 A1 | 3/2010 | Hayter |
| 2010/0057042 A1 | 3/2010 | Hayter |
| 2010/0069892 A1 | 3/2010 | Steinbach et al. |
| 2010/0077866 A1 | 4/2010 | Graboi et al. |
| 2010/0079760 A1 | 4/2010 | Bernacki |
| 2010/0094251 A1 | 4/2010 | Estes et al. |
| 2010/0106082 A1 | 4/2010 | Zhou |
| 2010/0114027 A1 | 5/2010 | Jacobson et al. |
| 2010/0121170 A1 | 5/2010 | Rule |
| 2010/0121415 A1 | 5/2010 | Skelton et al. |
| 2010/0130933 A1 | 5/2010 | Holland et al. |
| 2010/0131434 A1 | 5/2010 | Magent et al. |
| 2010/0141460 A1 | 6/2010 | Tokhtuev et al. |
| 2010/0147081 A1 | 6/2010 | Thomas et al. |
| 2010/0152554 A1 | 6/2010 | Steine et al. |
| 2010/0160854 A1 | 6/2010 | Gauthier |
| 2010/0168535 A1 | 7/2010 | Robinson et al. |
| 2010/0177375 A1 | 7/2010 | Seyfried |
| 2010/0185142 A1 | 7/2010 | Kamen et al. |
| 2010/0185182 A1 | 7/2010 | Alme et al. |
| 2010/0198034 A1 | 8/2010 | Thomas et al. |
| 2010/0198182 A1 | 8/2010 | Lanigan et al. |
| 2010/0198183 A1 | 8/2010 | Lanigan et al. |
| 2010/0211002 A1 | 8/2010 | Davis |
| 2010/0212407 A1 | 8/2010 | Stringham et al. |
| 2010/0212675 A1 | 8/2010 | Walling et al. |
| 2010/0217154 A1 | 8/2010 | Deshmukh et al. |
| 2010/0217621 A1 | 8/2010 | Schoenberg |
| 2010/0271218 A1 | 10/2010 | Hoag et al. |
| 2010/0271479 A1 | 10/2010 | Heydlauf |
| 2010/0273738 A1 | 10/2010 | Valcke et al. |
| 2010/0280430 A1 | 11/2010 | Caleffi et al. |
| 2010/0292634 A1 | 11/2010 | Kircher |
| 2010/0295686 A1 | 11/2010 | Sloan et al. |
| 2010/0298765 A1 | 11/2010 | Budiman et al. |
| 2010/0312039 A1 | 12/2010 | Quirico et al. |
| 2010/0317093 A1 | 12/2010 | Turewicz et al. |
| 2010/0317952 A1 | 12/2010 | Budiman et al. |
| 2010/0318025 A1 | 12/2010 | John |
| 2011/0000560 A1 | 1/2011 | Miller et al. |
| 2011/0001605 A1 | 1/2011 | Kiani et al. |
| 2011/0004186 A1 | 1/2011 | Butterfield |
| 2011/0009797 A1 | 1/2011 | Kelly et al. |
| 2011/0028885 A1 | 2/2011 | Eggers et al. |
| 2011/0046558 A1 | 2/2011 | Gravesen et al. |
| 2011/0054311 A1 | 3/2011 | Williams et al. |
| 2011/0062703 A1 | 3/2011 | Lopez et al. |
| 2011/0064612 A1 | 3/2011 | Franzoni et al. |
| 2011/0071464 A1 | 3/2011 | Palerm |
| 2011/0071844 A1 | 3/2011 | Cannon et al. |
| 2011/0072379 A1 | 3/2011 | Gannon |
| 2011/0077480 A1 | 3/2011 | Bloom et al. |
| 2011/0078608 A1 | 3/2011 | Gannon et al. |
| 2011/0099313 A1 | 4/2011 | Bolanowski |
| 2011/0105983 A1 | 5/2011 | Kelly et al. |
| 2011/0106561 A1 | 5/2011 | Eaton, Jr. et al. |
| 2011/0107251 A1 | 5/2011 | Guaitoli et al. |
| 2011/0137241 A1 | 6/2011 | DelCastillo et al. |
| 2011/0144595 A1 | 6/2011 | Cheng |
| 2011/0152770 A1 | 6/2011 | Diperna et al. |
| 2011/0160649 A1 | 6/2011 | Pan |
| 2011/0162647 A1 | 7/2011 | Huby et al. |
| 2011/0172918 A1 | 7/2011 | Tome |
| 2011/0175728 A1 | 7/2011 | Baker, Jr. |
| 2011/0190598 A1 | 8/2011 | Shusterman |
| 2011/0190694 A1 | 8/2011 | Lanier et al. |
| 2011/0218514 A1 | 9/2011 | Rebours |
| 2011/0238032 A1 | 9/2011 | McTaggart et al. |
| 2011/0264006 A1 | 10/2011 | Ali et al. |
| 2011/0264043 A1 | 10/2011 | Kotnick et al. |
| 2011/0282321 A1 | 11/2011 | Steil et al. |
| 2011/0313390 A1 | 12/2011 | Roy et al. |
| 2011/0319728 A1 | 12/2011 | Petisce et al. |
| 2011/0320049 A1 | 12/2011 | Chossat et al. |
| 2012/0016215 A1 | 1/2012 | Condurso et al. |
| 2012/0023431 A1 | 1/2012 | Roth |
| 2012/0025995 A1 | 2/2012 | Moberg et al. |
| 2012/0059234 A1 | 3/2012 | Barrett et al. |
| 2012/0068001 A1 | 3/2012 | Pushkarsky et al. |
| 2012/0083760 A1 | 4/2012 | Ledford et al. |
| 2012/0085277 A1 | 4/2012 | Abdel-Rahman |
| 2012/0089411 A1 | 4/2012 | Srnka et al. |
| 2012/0095433 A1 | 4/2012 | Hungerford et al. |
| 2012/0123322 A1 | 5/2012 | Scarpaci et al. |
| 2012/0143116 A1 | 6/2012 | Ware et al. |
| 2012/0180790 A1 | 7/2012 | Montgomery |
| 2012/0185267 A1 | 7/2012 | Kamen et al. |
| 2012/0191059 A1 | 7/2012 | Cummings et al. |
| 2012/0194341 A1 | 8/2012 | Peichel et al. |
| 2012/0203177 A1 | 8/2012 | Lanier |
| 2012/0222774 A1 | 9/2012 | Husnu et al. |
| 2012/0226350 A1 | 9/2012 | Rudser et al. |
| 2012/0245525 A1 | 9/2012 | Pope et al. |
| 2012/0259278 A1 | 10/2012 | Hayes et al. |
| 2012/0310204 A1 | 12/2012 | Krogh et al. |
| 2012/0323212 A1 | 12/2012 | Murphy |
| 2013/0006666 A1 | 1/2013 | Schneider |
| 2013/0009551 A1 | 1/2013 | Knapp |
| 2013/0012880 A1 | 1/2013 | Blomquist |
| 2013/0012917 A1 | 1/2013 | Miller et al. |
| 2013/0032634 A1 | 2/2013 | McKirdy |
| 2013/0041342 A1 | 2/2013 | Bernini et al. |
| 2013/0044111 A1 | 2/2013 | VanGilder et al. |
| 2013/0110538 A1 | 5/2013 | Butterfield et al. |
| 2013/0116649 A1 | 5/2013 | Breton et al. |
| 2013/0150766 A1 | 6/2013 | Olde et al. |
| 2013/0150821 A1 | 6/2013 | Bollish et al. |
| 2013/0173291 A1 | 7/2013 | Kelly |
| 2013/0177455 A1 | 7/2013 | Kamen et al. |
| 2013/0184676 A1 | 7/2013 | Kamen et al. |
| 2013/0197930 A1 | 8/2013 | Garibaldi et al. |
| 2013/0201482 A1 | 8/2013 | Munro |
| 2013/0218080 A1 | 8/2013 | Peterfreund et al. |
| 2013/0253430 A1 | 9/2013 | Kouyoumjian et al. |
| 2013/0253946 A1 | 9/2013 | Broselow |
| 2013/0274576 A1 | 10/2013 | Amirouche et al. |
| 2013/0281965 A1 | 10/2013 | Kamen et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0318158 A1 | 11/2013 | Teng et al. |
| 2013/0322201 A1 | 12/2013 | Hitchcock et al. |
| 2013/0345658 A1 | 12/2013 | Browne et al. |
| 2013/0345666 A1 | 12/2013 | Panduro et al. |
| 2014/0067425 A1 | 3/2014 | Dudar et al. |
| 2014/0132524 A1 | 5/2014 | Lee |
| 2014/0145915 A1 | 5/2014 | Ribble et al. |
| 2014/0180711 A1 | 6/2014 | Kamen et al. |

(56) References Cited

U.S. PATENT DOCUMENTS

| | | |
|---|---|---|
| 2014/0224829 A1 | 8/2014 | Capone et al. |
| 2014/0267563 A1 | 9/2014 | Baca et al. |
| 2014/0303591 A1 | 10/2014 | Peterfreund et al. |
| 2014/0303754 A1 | 10/2014 | Nixon et al. |
| 2015/0025453 A1 | 1/2015 | Ledford et al. |
| 2015/0033073 A1 | 1/2015 | Yang et al. |
| 2015/0051458 A1 | 2/2015 | Chen |
| 2015/0057108 A1 | 2/2015 | Regimbal |
| 2015/0065988 A1 | 3/2015 | Holderle et al. |
| 2015/0089439 A1 | 3/2015 | Wada |
| 2015/0114515 A1 | 4/2015 | Phallen |
| 2015/0141921 A1 | 5/2015 | Stewart et al. |
| 2015/0168958 A1 | 6/2015 | Downie et al. |
| 2015/0265765 A1 | 9/2015 | Yavorsky et al. |
| 2015/0278474 A1 | 10/2015 | Stueckemann |
| 2015/0289823 A1 | 10/2015 | Rack-Gomer et al. |
| 2015/0338340 A1 | 11/2015 | Jiang et al. |
| 2015/0343141 A1 | 12/2015 | Lindo et al. |
| 2015/0363086 A1 | 12/2015 | Lim |
| 2015/0371004 A1 | 12/2015 | Jones |
| 2016/0019352 A1 | 1/2016 | Seo |
| 2016/0042264 A1 | 2/2016 | Borges et al. |
| 2016/0051750 A1 | 2/2016 | Tsoukalis |
| 2016/0110088 A1 | 4/2016 | Vik et al. |
| 2016/0144101 A1 | 5/2016 | Pananen |
| 2016/0151560 A1 | 6/2016 | Toro et al. |
| 2016/0151562 A1 | 6/2016 | Magers et al. |
| 2016/0151601 A1 | 6/2016 | Cardelius et al. |
| 2016/0158437 A1 | 6/2016 | Biasi et al. |
| 2016/0175517 A1 | 6/2016 | Sileika et al. |
| 2016/0193604 A1 | 7/2016 | McFarland et al. |
| 2016/0253460 A1 | 9/2016 | Kanada |
| 2016/0339167 A1 | 11/2016 | Ledford et al. |
| 2017/0010677 A1 | 1/2017 | Roh |
| 2017/0043089 A1 | 2/2017 | Handler |
| 2017/0056604 A1 | 3/2017 | Cowan |
| 2017/0068498 A1 | 3/2017 | Hashem |
| 2017/0132867 A1 | 5/2017 | Berg et al. |
| 2017/0354941 A1 | 12/2017 | Brown et al. |
| 2018/0018440 A1 | 1/2018 | Sugawara |
| 2018/0021514 A1 | 1/2018 | Rosinko et al. |
| 2018/0206798 A1 | 7/2018 | Murai |
| 2018/0296751 A1 | 10/2018 | Lefort et al. |
| 2018/0300994 A1 | 10/2018 | Nelson et al. |
| 2018/0326146 A1 | 11/2018 | Gupta et al. |
| 2019/0072405 A1 | 3/2019 | Luchner |
| 2019/0091401 A1 | 3/2019 | Ruchti et al. |
| 2019/0117890 A1 | 4/2019 | Oruklu et al. |
| 2019/0160254 A1 | 5/2019 | Anand |
| 2019/0201607 A1 | 7/2019 | Öberg |
| 2019/0262535 A1 | 8/2019 | Shubinsky et al. |
| 2019/0282757 A1 | 9/2019 | Gylland et al. |
| 2019/0351131 A1 | 11/2019 | Butterfield et al. |
| 2020/0054825 A1 | 2/2020 | Kamen et al. |
| 2020/0069864 A1 | 3/2020 | Shubinsky et al. |
| 2020/0090122 A1 | 3/2020 | Hume |
| 2020/0113784 A1 | 4/2020 | Lopez et al. |
| 2020/0238007 A1 | 7/2020 | Day |
| 2020/0271499 A1 | 8/2020 | Ruchti et al. |
| 2020/0282137 A1 | 9/2020 | Dumas, III et al. |
| 2020/0319837 A1 | 10/2020 | Fryman |
| 2020/0324044 A1 | 10/2020 | Gylland et al. |
| 2020/0330689 A1 | 10/2020 | Nemoto et al. |
| 2020/0357500 A1 | 11/2020 | Rubalcaba, Jr. et al. |
| 2020/0384191 A1 | 12/2020 | Rosinko et al. |
| 2021/0158481 A1 | 5/2021 | Wang |
| 2021/0158946 A1 | 5/2021 | Starobinets et al. |
| 2021/0162115 A1 | 6/2021 | Surine |
| 2021/0170101 A1 | 6/2021 | Cavendish, Jr. et al. |
| 2021/0260283 A1 | 8/2021 | Oruklu et al. |
| 2021/0295263 A1 | 9/2021 | Hume et al. |
| 2021/0304864 A1 | 9/2021 | Kamen et al. |
| 2021/0397396 A1 | 12/2021 | Fryman |
| 2022/0031943 A1 | 2/2022 | Dumas, III |
| 2022/0184302 A1 | 6/2022 | Cavendish, Jr. et al. |
| 2022/0184304 A1 | 6/2022 | Rinehart |
| 2022/0296806 A1 | 9/2022 | Shubinsky et al. |
| 2022/0305200 A1 | 9/2022 | Gylland et al. |
| 2022/0331518 A1 | 10/2022 | Shubinsky et al. |
| 2022/0362463 A1 | 11/2022 | Lindo et al. |
| 2023/0010290 A1 | 1/2023 | Oruklu et al. |
| 2023/0010638 A1 | 1/2023 | Rubalcaba, Jr. et al. |
| 2023/0017117 A1 | 1/2023 | Sileika et al. |
| 2023/0058662 A1 | 2/2023 | Ruchti et al. |
| 2023/0112979 A1 | 4/2023 | Xavier |
| 2023/0115595 A1 | 4/2023 | Cousineau et al. |
| 2023/0181419 A1 | 6/2023 | Fister |
| 2023/0245741 A1 | 8/2023 | Shigyo |
| 2023/0270938 A1 | 8/2023 | Dumas, III et al. |
| 2023/0285669 A1 | 9/2023 | Day |
| 2023/0310735 A1 | 10/2023 | Cousineau |
| 2024/0201922 A1 | 6/2024 | Fryman |
| 2024/0263981 A1 | 8/2024 | Ruchti et al. |
| 2024/0325246 A1 | 10/2024 | Janssen |
| 2024/0366858 A1 | 11/2024 | Cousineau et al. |

FOREIGN PATENT DOCUMENTS

| | | |
|---|---|---|
| CA | 2 113 473 | 3/1993 |
| CA | 2 551 817 | 7/2005 |
| CA | 2 554 407 | 8/2005 |
| CN | 105682703 | 6/2016 |
| CN | 107106042 | 8/2017 |
| CN | 110573195 | 12/2019 |
| CN | 105848694 | 1/2020 |
| CN | 111954966 | 11/2020 |
| CN | 306893275 | 10/2021 |
| CN | 307412164 | 6/2022 |
| CN | 307979072 | 4/2023 |
| CN | 112105405 | 8/2023 |
| CN | 308499458 | 3/2024 |
| CO | 0020220004676-0001 | 11/2022 |
| CO | 0020220008155-0001 | 11/2022 |
| DE | 31 12 762 | 1/1983 |
| DE | 34 35 647 | 7/1985 |
| DE | 35 30 747 | 3/1987 |
| DE | 37 20 664 | 1/1989 |
| DE | 38 27 444 | 2/1990 |
| DE | 197 34 002 | 9/1998 |
| DE | 199 01 078 | 2/2000 |
| DE | 198 40 965 | 3/2000 |
| DE | 198 44 252 | 3/2000 |
| DE | 199 32 147 | 1/2001 |
| DE | 102 49 238 | 5/2004 |
| DE | 103 52 456 | 7/2005 |
| EM | 008932172-0003 | 4/2022 |
| EM | 008932172-0004 | 4/2022 |
| EP | 0 282 323 | 9/1988 |
| EP | 0 291 727 | 11/1988 |
| EP | 0 319 272 | 6/1989 |
| EP | 0 319 275 | 6/1989 |
| EP | 0 335 385 | 10/1989 |
| EP | 0 337 092 | 10/1989 |
| EP | 0 341 582 | 11/1989 |
| EP | 0 370 162 | 5/1990 |
| EP | 0 387 724 | 9/1990 |
| EP | 0 429 866 | 6/1991 |
| EP | 0 441 323 | 8/1991 |
| EP | 0 453 211 | 10/1991 |
| EP | 0 462 405 | 12/1991 |
| EP | 0 501 234 | 9/1992 |
| EP | 0 516 130 | 12/1992 |
| EP | 0 519 765 | 12/1992 |
| EP | 0 643 301 | 3/1995 |
| EP | 0 683 465 | 11/1995 |
| EP | 0 431 310 | 1/1996 |
| EP | 0 589 439 | 8/1998 |
| EP | 0 880 936 | 12/1998 |
| EP | 0 954 090 | 11/1999 |
| EP | 0 960 627 | 12/1999 |
| EP | 1 174 817 | 1/2002 |
| EP | 1 177 802 | 2/2002 |
| EP | 1 197 178 | 4/2002 |
| EP | 1 500 025 | 4/2003 |

(56) References Cited

FOREIGN PATENT DOCUMENTS

| | | |
|---|---|---|
| EP | 1 813 188 | 8/2007 |
| EP | 1 490 131 | 12/2007 |
| EP | 2 062 527 | 5/2009 |
| EP | 2 228 004 | 9/2010 |
| EP | 2 243 506 | 10/2010 |
| EP | 2 381 260 | 10/2011 |
| ES | 254513 | 10/1981 |
| FR | 2 717 919 | 9/1995 |
| GB | 2 121 971 | 1/1984 |
| GB | 2 303 706 | 2/1997 |
| GB | 2 312 022 | 10/1997 |
| GB | 2 312 046 | 10/1997 |
| GB | 6 201 192 | 4/2022 |
| GB | 6 201 193 | 4/2022 |
| JP | 01-301118 | 12/1989 |
| JP | 01-308568 | 12/1989 |
| JP | 04-231966 | 8/1992 |
| JP | 07-502678 | 3/1995 |
| JP | 07-289638 | 11/1995 |
| JP | 11-128344 | 5/1999 |
| JP | 2000-111374 | 4/2000 |
| JP | 2000-510575 | 8/2000 |
| JP | 2000-515716 | 11/2000 |
| JP | 2001-356034 | 12/2001 |
| JP | 2002-506514 | 2/2002 |
| JP | 2002-131105 | 5/2002 |
| JP | 2003-038642 | 2/2003 |
| JP | 2003-050144 | 2/2003 |
| JP | 2005-021463 | 1/2005 |
| JP | 2005-524081 | 3/2005 |
| JP | 2006-517423 | 7/2006 |
| JP | 2007-071695 | 3/2007 |
| JP | 2007-518471 | 7/2007 |
| JP | 2007-520270 | 7/2007 |
| JP | 2007-275106 | 10/2007 |
| JP | 2008-249400 | 10/2008 |
| JP | 4322661 | 6/2009 |
| JP | 2009-148592 | 7/2009 |
| JP | 2010-063767 | 3/2010 |
| JP | 5716879 | 3/2015 |
| TW | 201841165 | 11/2018 |
| WO | WO 84/000690 | 3/1984 |
| WO | WO 84/000894 | 3/1984 |
| WO | WO 90/007942 | 7/1990 |
| WO | WO 91/000113 | 1/1991 |
| WO | WO 91/016087 | 10/1991 |
| WO | WO 91/016416 | 10/1991 |
| WO | WO 93/004284 | 3/1993 |
| WO | WO 95/016200 | 6/1995 |
| WO | WO 95/031233 | 11/1995 |
| WO | WO 96/008755 | 3/1996 |
| WO | WO 96/025186 | 8/1996 |
| WO | WO 96/028209 | 9/1996 |
| WO | WO 96/041156 | 12/1996 |
| WO | WO 97/010013 | 3/1997 |
| WO | WO 97/030333 | 8/1997 |
| WO | WO 98/004304 | 2/1998 |
| WO | WO 98/012670 | 3/1998 |
| WO | WO 98/014234 | 4/1998 |
| WO | WO 98/019263 | 5/1998 |
| WO | WO 98/044320 | 10/1998 |
| WO | WO 98/056441 | 12/1998 |
| WO | WO 99/010029 | 3/1999 |
| WO | WO 99/015216 | 4/1999 |
| WO | WO 99/051003 | 10/1999 |
| WO | WO 99/052575 | 10/1999 |
| WO | WO 00/013580 | 3/2000 |
| WO | WO 00/013726 | 3/2000 |
| WO | WO 00/041621 | 7/2000 |
| WO | WO 01/014974 | 3/2001 |
| WO | WO 01/033484 | 5/2001 |
| WO | WO 02/005702 | 1/2002 |
| WO | WO 02/009795 | 2/2002 |
| WO | WO 02/027276 | 4/2002 |
| WO | WO 02/066101 | 8/2002 |
| WO | WO 02/087664 | 11/2002 |
| WO | WO 03/006091 | 1/2003 |
| WO | WO 03/053498 | 7/2003 |
| WO | WO 03/093780 | 11/2003 |
| WO | WO 2004/035115 | 4/2004 |
| WO | WO 2004/060455 | 7/2004 |
| WO | WO 2004/061745 | 7/2004 |
| WO | WO 2004/070556 | 8/2004 |
| WO | WO 2004/070994 | 8/2004 |
| WO | WO 2004/112579 | 12/2004 |
| WO | WO 2005/018716 | 3/2005 |
| WO | WO 2005/030489 | 4/2005 |
| WO | WO 2005/036447 | 4/2005 |
| WO | WO 2005/050526 | 6/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |
| WO | WO 2005/118015 | 12/2005 |
| WO | WO 2006/016122 | 2/2006 |
| WO | WO 2006/022906 | 3/2006 |
| WO | WO 2006/026270 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/019016 | 2/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2009/141504 | 11/2009 |
| WO | WO 2010/017279 | 2/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/135646 | 11/2010 |
| WO | WO 2010/135654 | 11/2010 |
| WO | WO 2010/135670 | 11/2010 |
| WO | WO 2010/135686 | 11/2010 |
| WO | WO 2010/148205 | 12/2010 |
| WO | WO 2011/017778 | 2/2011 |
| WO | WO 2011/080188 | 7/2011 |
| WO | WO 2011/109774 | 9/2011 |
| WO | WO 2012/042763 | 4/2012 |
| WO | WO 2012/082599 | 6/2012 |
| WO | WO 2012/108910 | 8/2012 |
| WO | WO 2012/167090 | 12/2012 |
| WO | WO 2013/036854 | 3/2013 |
| WO | WO 2013/096769 | 6/2013 |
| WO | WO 2015/134478 | 9/2015 |
| WO | WO 2017/051271 | 3/2017 |
| WO | WO 2017/087157 | 5/2017 |
| WO | WO 2017/144366 | 8/2017 |
| WO | WO 2017/197024 | 11/2017 |
| WO | WO 2019/063462 | 4/2019 |
| WO | WO 2019/092680 | 5/2019 |
| WO | WO 2020/214717 | 10/2020 |
| WO | WO 2022/020184 | 1/2022 |
| WO | WO 2022/072159 | 4/2022 |
| WO | WO 2022/125471 | 6/2022 |
| WO | WO 2023/064662 | 4/2023 |
| WO | WO 2023/108030 | 6/2023 |

(56) References Cited

FOREIGN PATENT DOCUMENTS

| WO | WO 2023/192791 | 10/2023 |
|---|---|---|
| WO | WO 2023/244922 | 12/2023 |

OTHER PUBLICATIONS

ALARIS® Medical Systems, "Signature Edition® GOLD—Single & Dual Channel Infusion System", San Diego, CA, USA, date unknown, but believed to be at least as early as Nov. 29, 2008, pp. 2-88 & 2-91.
Allegro, "3955—Full-Bridge PWM Microstepping Motor Drive", Datasheet, 1997, pp. 16.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
Baxter, "Baxter Receives 510(k) Clearance for Next-Generation SIGMA Spectrum Infusion Pump with Master Drug Library" Press Release, May 8, 2014, pp. 2. http://web.archive.org/web/20160403140025/http://www.baxter.com/news-media/newsroom/press-releases/2014/05_08_14_sigma.page.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Binder et al., "Insulin Infusion with Parenteral Nutrition in Extremely Low Birth Weight Infants with Hyperglycemia", Journal of Pediatrics, Feb. 1989, vol. 114, No. 2, pp. 273-280.
Bode et al., "Intravenous Insulin Infusion Therapy: Indications, Methods, and Transition to Subcutaneous Insulin Therapy", Endocrine Practice, Mar./Apr. 2004, vol. 10, Supplement 2, pp. 71-80.
Buhrdorf et al., "Capacitive Micromachined Ultrasonic Transducers and their Application", Proceedings of the IEEE Ultrasonics Symposium, Feb. 2001, vol. 2, pp. 933-940.
Cannon, MD et al., "Automated Heparin-Delivery System to Control Activated Partial Thromboplastin Time", Circulation, Feb. 16, 1999, vol. 99, pp. 751-756.
"CareAware® Infusion Management", Cerner Store, as printed May 12, 2011, pp. 3, https://store.cerner.com/items/7.
Chen et al., "Enabling Location-Based Services on Wireless LANs", The 11th IEEE International Conference on Networks, ICON 2003, Sep. 28-Oct. 1, 2003, pp. 567-572.
Cheung et al., "Hyperglycemia is Associated with Adverse Outcomes in Patients Receiving Total Parenteral Nutrition", Diabetes Care, Oct. 2005, vol. 28, No. 10, pp. 2367-2371.
Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.
"Continually vs Continuously", https://web.archive.org/web/20090813092423/http://www.diffen.com/difference/Continually_vs_Continuously, as accessed Aug. 13, 2009 in 4 pages.
"CritiCore® Monitor: Critical Fluid Output and Core Bladder Temperature Monitor", BARD Urological Catheter Systems, Advertisement, 2005, pp. 2.
Daimiwal et al., "Wireless Transfusion Supervision and Analysis Using Embedded System", IEEE, 2010 International Conference ICBBT, China, Apr. 2010, pp. 56-60.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
"Decision of the Administrative Council of Oct. 16, 2013 Amending Rule 135 and 164 of the Implementing Regulations to the European Patent Convention (CA/D 17/13)", Official Journal EPO Nov. 2013, Nov. 2013, pp. 503-506. http://archive.epo.org/epo/pubs/oj013/11_13/11_5033.pdf.
"Decision of the Administrative Council of Oct. 27, 2009 Amending the Implementing Regulations to the European Patent Convention (CA/D 20/09)", Official Journal EPO Dec. 2009, Dec. 2009, pp. 582-584. http://archive.epo.org/epo/pubs/oj009/12_09/12_5829.pdf.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
"Differential Pressure Transmitter, Series PD-39 X", SensorsOne Ltd., Advertisement, Dec. 2005, pp. 2.
Dunster et al., "Flow Continuity of Infusion Systems at Low Flow Rates", Anaesthesia and Intensive Care, Oct. 1995, vol. 23, No. 5, pp. 5.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
"Froth", http://www.merriam-webster.com/dictionary/froth, as accessed May 13, 2015 in 1 page.
Goldberg et al., "Clinical Results of an Updated Insulin Infusion Protocol in Critically Ill Patients", Diabetes Spectrum, 2005, vol. 18, No. 3, pp. 188-191.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hospira, "Plum A+™ Infusion System" as archived Dec. 1, 2012, pp. 2. www.hospira.com/products_and_services/infusion_pumps/plum/index.
Hospira, "Plum XL™ Series Infusion System" Technical Service Manual, Feb. 2005, Lake Forest, Illinois, USA, pp. i-vii, 5-14, 8-3.
Ilfeld et al., "Delivery Rate Accuracy of Portable, Bolus-Capable Infusion Pumps Used for Patient-Controlled Continuous Regional Analgesia", Regional Anesthesia and Pain Medicine, Jan.- Feb. 2003, vol. 28, No. 1, pp. 17-23.
Ilfeld et al., "Portable Infusion Pumps Used for Continuous Regional Analgesia: Delivery Rate Accuracy and Consistency", Regional Anesthesia and Pain Medicine, Sep.-Oct. 2003, vol. 28, No. 5, pp. 424-432.
JMS Co., Ltd., "Infusion Pump: OT-701", Tokyo, Japan, 2002, pp. 4.
Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology, vol. 6, No. 6, pp. 1413-1419.
Kutcher et al., "The Effect of Lighting Conditions on Caries Interpretation with a Laptop Computer in a Clinical Setting", Elsevier, Oct. 2006, vol. 102, No. 4, pp. 537-543.
Lamsdale et al., "A Usability Evaluation of an Infusion Pump by Nurses Using a Patient Simulator", Proceedings of the Human Factors and Ergonomics Society 49th Annual Meeting, Sep. 2005, pp. 1024-1028.
Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.
Magaji et al., "Inpatient Management of Hyperglycemia and Diabetes", Clinical Diabetes, 2011, vol. 29, No. 1, pp. 3-9.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Maynard et al., "Subcutaneous Insulin Order Sets and Protocols: Effective Design and Implementation Strategies", Journal of Hospital Medicine, Sep./Oct. 2008, vol. 3, Issue 5, Supplement 5, pp. S29-S41.
Merry et al., "A New, Safety-Oriented, Integrated Drug Administration and Automated Anesthesia Record System", Anesthesia & Analgesia, Aug. 2001, vol. 93, No. 2 pp. 385-390.
Microchip Technology Inc., "MTA11200B; TrueGauge™ Intelligent Battery Management I.C.", https://www.elektronik.ropla.eu/pdf/stock/mcp/mta11200b.pdf, 1995, pp. 44.
Moghissi, Etie, MD, FACP, FACE, "Hyperglycemia in Hospitalized Patients", A Supplement to ACP Hospitalist, Jun. 15, 2008, pp. 32.

(56) References Cited

OTHER PUBLICATIONS

Nuckols et al., "Programmable Infusion Pumps in ICUs: An Analysis of Corresponding Adverse Drug Events", Journal of General Internal Medicine, 2007, vol. 23, Supp. 1, pp. 41-45.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
SGS-Thomson Microelectronics, "L6219—Stepper Motor Drive", Datasheet, Dec. 1996, pp. 10.
SGS-Thomson Microelectronics, "PBL3717A—Stepper Motor Drive", Datasheet, Apr. 1993, pp. 11.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Smith, Joe, "Infusion Pump Informatics", CatalyzeCare: Transforming Healthcare, as printed May 12, 2011, pp. 2.
Tang et al., "Linear Dimensionality Reduction Using Relevance Weighted LDA", Pattern Recognition, 2005, vol. 38, pp. 485-493, http://staff.ustc.edu.cn/~ketang/papers/TangSuganYaoQin_PR04.pdf.
Thomas et al., "Implementation of a Tight Glycaemic Control Protocol Using a Web-Based Insulin Dose Calculator", Anaesthesia, 2005, vol. 60, pp. 1093-1100.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Westbrook et al., "Errors in the Administration of Intravenous Medications in Hospital and the Role of Correct Procedures and Nurse Experience", BMJ Quality & Safety, 2011, vol. 20, pp. 1027-1034.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
Abbott Laboratories, "LifeCare® 5000, Plum®: Concurrent Flow Infusion System with DataPort™", System Operating Manual, Version 1.6, Jul. 1998, pp. 76.
International Search Report and Written Opinion received in PCT Application No. PCT/US2021/062072, dated Mar. 18, 2022 in 14 pages.
International Preliminary Report on Patentability and Written Opinion received in PCT Application No. PCT/US2021/062072, dated Jun. 22, 2023 in 11 pages.
Junda, Lin, "Global development trends of green bonds", Jul. 10, 2018, pp. 9.
Notice of Opposition in European Patent Application No. 16759381.3 (Patent No. EP3285827), dated May 31, 2023 in 48 pages.
Response to Notice of Opposition in European Patent Application No. 16759381.3 (Patent No. EP3285827), dated Oct. 23, 2023 in 63 pages.
Amazon, Post-it Message "Sign Here" Flags, 30/Dispenser, 4 Dispensers/Pack, Published Sep. 29, 2016, https://www.amazon.com/Assorted-Color-Colors-Dispenser-MMM684SH/dp/B00006JNMN/?th=1, * pages.
File:Soldado, Raso Fuerza Aerea Boliviana.jpg, Feb. 9, 2021, https://commons.m.wikimedia.org/wiki/File:Soldado_Raso_Fuerza_A%C3%A9rea_Boliviana.jpg, 1 page.
Fresenius, "Infusion Workstation: Orchestra® Base Intensive", Operator's Guide, Jun. 20, 2006, pp. 24. <https://manualmachine.com/fresenius/orchestrabaseunit/7455278-user-manual/>.
"ICU Medical Receives FDA Clearance for New Infusion Pump", Medical Design & Development Staff, Aug. 29, 2023, https://www.medicaldesigndevelopment.com/topics/devices/news/22871498/icu-medical-receives-fda-clearance-for-new-infusion-pump. 2 pages.

CONCURRENT INFUSION WITH COMMON LINE AUTO FLUSH

CROSS-REFERENCE TO RELATED APPLICATIONS

The present application is a continuation of U.S. Ser. No. 17/114,359, filed Dec. 7, 2020, now U.S. Pat. No. 11,135,360, which is incorporated by reference herein. The present application is also related to U.S. application Ser. No. 16/301,379, filed Nov. 13, 2018, which is the national stage of International Application No. PCT/US2017/032017, filed May 10, 2017, which claims the benefit of priority from U.S. Provisional No. 62/336,191, filed May 13, 2016, all of which are incorporated by reference in their entireties.

BACKGROUND

Field

The present invention relates to medical devices and infusion pump systems.

Infusion pumps are medical devices that deliver fluids, including nutrients and medications such as antibiotics, chemotherapy drugs, and pain relievers, in controlled amounts. Many types of pumps, including large volume, patient-controlled analgesia (PCA), elastomeric, syringe, enteral, and insulin pumps, are used worldwide in healthcare facilities, such as hospitals, and in the home. Clinicians and patients rely on pumps for safe and accurate administration of fluids and medications.

It is often desirable to provide more than one therapeutic fluid to the patient from the same infusion pump. Two fluid reservoirs with different therapeutic fluids are connected to the infusion pump and then delivered through a common line having a terminal fluid delivery end. The terminal fluid delivery end is attached to the patient. The first therapeutic fluid and second therapeutic fluid may be administered concurrently or one at a time by controlling the fluid flow path to draw fluid from both reservoirs or from only one reservoir.

When switching from single to concurrent fluid delivery, the therapeutic fluid remaining in the common line may lead to complexity in controlling delivery volumes or flow rates when switching between fluid sources. For example, the remaining therapeutic fluid must be cleared from the common line before the next therapeutic fluid begins administration (entering the patient's body), which delays the next therapeutic fluid from reaching the patient. In addition, when the therapeutic fluids are administered concurrently, the first therapeutic fluid remaining in the common line will be administered at the combined rate of the first therapeutic fluid infusion rate plus the second therapeutic fluid infusion rate, e.g., the remaining first therapeutic fluid will be administered at the combined rate determined from the rates specified for the first and second therapeutic fluids. This can result in the patient receiving more or less than the optimum therapy with respect to the first therapeutic fluid. Furthermore, the remaining therapeutic fluid may not be correctly accounted for, potentially creating delays in the values indicated at the infusion pump, versus therapeutic fluid received by the patient. Finally, a single medication delivered at a combined rate may actually result in the single medication being infused at a rate that can exceed an upper soft or hard limit specified for such medication until the medication in the common line is displaced by an intended second fluid (in the case of a piggyback infusion) or a mixture of first and second fluids (in the case of a concurrent delivery). While the pump data will be correct in terms of infusion rates over given times, the actual fluid delivery to the terminal fluid delivery end at the patient may not be correctly captured in pump and system data.

In addition, while some infusion therapies specify a particular volume of fluid to infuse to a patient, in some therapies it is preferred to deliver 100% of the volume of fluid contained within a particular fluid reservoir, such that the fluid is delivered until the reservoir is emptied. However, with many infusion pump systems, due to variable fluid volume contained in the reservoir and typical pump delivery accuracy tolerances and system dependencies, it is only possible to achieve 100% fluid delivery by over-programming the pump, or by entering pump programming parameters that do not accurately reflect the volume and duration of fluid actually administered to the patient.

It would be desirable to have infusion pump systems and methods with common line auto flush that would overcome the above disadvantages.

SUMMARY

In one embodiment, a control system is provided to control operation of an infusion pump of an infusion pump system. The infusion pump system includes a first reservoir configured to hold a first fluid, a second reservoir configured to hold a second fluid, a junction in fluid communication with the first reservoir and the second reservoir, a common line in fluid communication with the junction and having a terminal fluid delivery end, and the infusion pump, wherein the infusion pump is operable to drive fluid through the common line toward the terminal fluid delivery end. The control system includes: one or more hardware processors; and a memory storing executable instructions that when executed by the one or more hardware processors, configure the infusion pump to: receive instructions to deliver the first fluid at a first rate, subsequently concurrently deliver a mixture of the first fluid and the second fluid, and concurrently deliver the first fluid at the first rate and the second fluid at a second rate; infuse the first fluid at the first rate along a first flow path, the first flow path including the common line; determine a common line volume corresponding to a volume of the common line; draw the first fluid from the first reservoir the second fluid from the second reservoir to deliver the mixture of the first fluid and the second fluid; infuse the mixture of the first fluid and the second fluid at a flushing rate along a second flow path, the second flow path including the common line; determine that an infused volume of the mixture of the first fluid and the second fluid equals or exceeds the common line volume; and change the infusion rate of the mixture of the first fluid and the second fluid from the flushing rate to a combined rate, wherein the combined rate is the sum of the first rate and the second rate, and continue to infuse the mixture of the first fluid and the second fluid along the second flow path at the combined rate.

The control system may also include a mixing chamber in fluid communication with the first reservoir, the second reservoir, and the common line. The executable instructions may further configure the infusion pump to determine the flushing rate based upon whether the first fluid is a medicinal fluid, determine the flushing rate as the first rate when the first fluid is a medicinal fluid, or determine the flushing rate as the first rate increased by a flushing rate factor when the first fluid is not a medicinal fluid.

The instructions may further configure the infusion pump to receive the common line volume from a user input, retrieve the common line volume from the memory, or retrieve the common line volume over a network. The common line volume may be predetermined. The instructions may further configure the infusion pump to determine the common volume based on the first fluid. The first rate may be different than the second rate.

The instructions may further configure the infusion pump to receive the instructions for the delivery from an input via a user interface. The executable instructions further configure the infusion pump to: determine that an infusion of the second fluid has completed; draw the first fluid from the first reservoir without drawing the second fluid from the second reservoir; infuse the first fluid at the combined rate; determine that a volume of the first fluid infused at the combined rate equals or exceeds the common line volume; and change the infusion rate of the first fluid from the combined rate to the first rate.

The executable instructions may configure the infusion pump to determine that an infusion of the second fluid has completed by comparing a volume of fluid infused to a programmed volume to infuse, determine that an infusion of the second fluid has completed by receiving an instruction to stop infusing the second fluid, or determine that an infusion of the second fluid has completed by determining that the second reservoir has been depleted of second fluid.

The executable instructions may further configure the infusion pump to: determine that an infusion of the first fluid has completed; draw the second fluid from the second reservoir without drawing the first fluid from the first reservoir; infuse the second fluid at the combined rate; determine that a volume of the second fluid infused at the combined rate equals or exceeds the common line volume; and change the infusion rate of the second fluid from the combined rate to the second rate.

The executable instructions may configure the infusion pump to determine that an infusion of the first fluid has completed by comparing a volume of fluid infused to a programmed volume to infuse, determine that an infusion of the first fluid has completed by receiving an instruction to stop infusing the first fluid, or determine that an infusion of the first fluid has completed by determining that the first reservoir has been depleted of first fluid.

In another embodiment, a method for controlling operation of an infusion pump of an infusion pump system is provided. The infusion pump system includes a first reservoir configured to hold a first fluid, a second reservoir configured to hold a second fluid, a junction in fluid communication with the first reservoir and the second reservoir, a common line in fluid communication with the junction and having a terminal fluid delivery end, and the infusion pump, wherein the infusion pump is operable to drive fluid through the common line toward the terminal fluid delivery end. The method includes: drawing the first fluid from the first reservoir and the second fluid from the second reservoir to form a mixture of the first fluid and the second fluid; infusing the mixture of the first fluid and the second fluid at a combined rate, wherein the combined rate is a sum of a first infusion rate associated with the first fluid and a second infusion rate associated with the second fluid; determining a common line volume corresponding to a volume of the common line; determining that the second reservoir is depleted; drawing the first fluid from the first reservoir without drawing the second fluid from the second reservoir; driving the first fluid at the combined rate along a flow path including the common line; determining that a driven volume of the first fluid equals or exceeds the common line volume; and changing the infusion rate of the first fluid from the combined rate to the first rate, and continuing to infuse the first fluid along the flow path at the first rate.

The infusion pump may also include a mixing chamber in fluid communication with the first reservoir, the second reservoir, and the common line. Determining the common line volume may include receiving the common line volume from a user input, retrieving the common line volume from a memory, or retrieving the common line volume over a network. The common line volume may be predetermined.

Determining the common line volume may include determining the common line volume based on the first fluid. The first rate may be different than the second rate. Driving the first fluid at the combined rate may include driving the first fluid at a rate that exceeds a drug library rate limit associated with the first fluid. Determining that the second reservoir is depleted may include receiving a sensor signal that air is present in the junction or in a line coupling the junction to the second reservoir.

The method may further include pumping the first fluid from the first reservoir towards the second reservoir in response to receiving the sensor signal that air is present in the junction or in the line coupling the junction to the second reservoir.

In yet another embodiment, a control system for controlling operation of an infusion pump of an infusion pump system is provided. The infusion pump system includes a first reservoir configured to hold a first fluid, a second reservoir configured to hold a second fluid, a junction in fluid communication with the first reservoir and the second reservoir, a common line in fluid communication with the junction and having a terminal fluid delivery end, and the infusion pump, wherein the infusion pump is operable to drive fluid through the common line toward the terminal fluid delivery end. The control system includes: one or more hardware processors; and a memory storing executable instructions that when executed by the one or more hardware processors, configure the infusion pump to: draw the first fluid from the first reservoir and the second fluid from the second reservoir to form a mixture of the first fluid and the second fluid; infuse the mixture of the first fluid and the second fluid at a combined rate, wherein the combined rate is a sum of a first infusion rate associated with the first fluid and a second infusion rate associated with the second fluid; determine a common line volume corresponding to a volume of the common line; draw the first fluid from the first reservoir without drawing the second fluid from the second reservoir; drive the first fluid at the combined rate along a flow path including the common line; determine that a driven volume of the first fluid equals or exceeds the common line volume; and change the infusion rate of the first fluid from the combined rate to the first rate, and continue to infuse the first fluid along the flow path at the first rate.

The infusion pump may also include a mixing chamber in fluid communication with the first reservoir, the second reservoir, and the common line.

The executable instructions may also configure the infusion pump to determine the common line volume by receiving the common line volume from a user input, determine the common line volume by retrieving the common line volume from a memory, or determine the common line volume by retrieving the common line volume over a network. The common line volume may be predetermined.

The executable instructions may also configure the infusion pump to determine the common line volume based on the first fluid. The first rate may be different than the second rate.

The executable instructions may configure the infusion pump to drive the first fluid at the combined rate by driving the first fluid at a rate that exceeds a drug library rate limit associated with the first fluid. The executable instructions may configure the infusion pump to determine that the second reservoir is depleted by receiving a sensor signal that air is present in the junction or in a line coupling the junction to the second reservoir. The executable instructions may further configure the infusion pump to pump the first fluid from the first reservoir towards the second reservoir in response to receiving the sensor signal that air is present in the junction or in the line coupling the junction to the second reservoir.

In yet another embodiment, a method for controlling operation of an infusion pump of an infusion pump system is provided. The infusion pump system includes a first reservoir configured to hold a first fluid, a second reservoir configured to hold a second fluid, a junction in fluid communication with the first reservoir and the second reservoir, a common line in fluid communication with the junction and having a terminal fluid delivery end, and the infusion pump, wherein the infusion pump is operable to drive fluid through the common line toward the terminal fluid delivery end. The method includes: receiving instructions to deliver the first fluid at a first rate, subsequently concurrently deliver a mixture of the first fluid and the second fluid, and concurrently deliver the first fluid at the first rate and the second fluid at a second rate; infusing the first fluid at the first rate along a first flow path, the first flow path including the common line; determining a common line volume corresponding to a volume of the common line; drawing the first fluid from the first reservoir the second fluid from the second reservoir to deliver the mixture of the first fluid and the second fluid; infusing the mixture of the first fluid and the second fluid at a flushing rate along a second flow path, the second flow path including the common line; determining that an infused volume of the mixture of the first fluid and the second fluid equals or exceeds the common line volume; and changing the infusion rate of the mixture of the first fluid and the second fluid from the flushing rate to a combined rate, wherein the combined rate is the sum of the first rate and the second rate, and continue to infuse the mixture of the first fluid and the second fluid along the second flow path at the combined rate.

The infusion pump system may also include a mixing chamber in fluid communication with the first reservoir, the second reservoir, and the common line. The method may also include determining the flushing rate based upon whether the first fluid is a medicinal fluid, determining the flushing rate as the first rate when the first fluid is a medicinal fluid, or determining the flushing rate as the first rate increased by a flushing rate factor when the first fluid is not a medicinal fluid.

The method may also include receiving the common line volume from a user input, retrieving the common line volume from the memory, or retrieving the common line volume over a network. The common line volume may be predetermined.

The method may also include determining the common volume based on the first fluid. The first rate may be different than the second rate. Infusing the mixture of the first fluid and the second fluid at the flushing rate may include one or more of delivering the first fluid at a first fluid flush rate that exceeds a drug library rate limit associated with the first fluid or delivering the second fluid at a second fluid flush rate that exceeds a drug library rate limit associated with the second fluid.

The method may also include: determining that an infusion of the second fluid has completed; drawing the first fluid from the first reservoir without drawing the second fluid from the second reservoir; infusing the first fluid at the combined rate; determining that a volume of the first fluid infused at the combined rate equals or exceeds the common line volume; and changing the infusion rate of the first fluid from the combined rate to the first rate.

The method may also include determining that an infusion of the second fluid has completed by comparing a volume of fluid infused to a programmed volume to infuse, determining that an infusion of the second fluid has completed by receiving an instruction to stop infusing the second fluid, or determining that an infusion of the second fluid has completed by determining that the second reservoir has been depleted of second fluid. Infusing the first fluid at the combined rate may include infusing the first fluid at a rate that exceeds a drug library rate limit associated with the first fluid.

The method may also include: determining that an infusion of the first fluid has completed; drawing the second fluid from the second reservoir without drawing the first fluid from the first reservoir; infusing the second fluid at the combined rate; determining that a volume of the second fluid infused at the combined rate equals or exceeds the common line volume; and changing the infusion rate of the second fluid from the combined rate to the second rate.

The method may also include determining that an infusion of the first fluid has completed by comparing a volume of fluid infused to a programmed volume to infuse, determining that an infusion of the first fluid has completed by receiving an instruction to stop infusing the first fluid, or determining that an infusion of the first fluid has completed by determining that the first reservoir has been depleted of first fluid. Infusing the second fluid at the combined rate may include infusing the second fluid at a rate that exceeds a drug library rate limit associated with the second fluid.

The foregoing and other features and advantages of the invention will become further apparent from the following detailed description of the presently preferred embodiments, read in conjunction with the accompanying drawings. The detailed description and drawings are merely illustrative of the invention rather than limiting. The scope of the invention is defined by the appended claims and equivalents thereof.

In certain embodiments, a control system can control operation of an infusion pump system. The infusion pump system can include a first reservoir that can hold a first fluid, a second reservoir configured to hold a second fluid, a junction in fluid communication with the first reservoir and the second reservoir, a common line in fluid communication with the junction and having a terminal fluid delivery end, and an infusion pump operable to drive fluid through the common line toward the terminal fluid delivery end. The control system can control whether fluids from the reservoirs are drawn individually or concurrently (e.g., simultaneously or in an alternating manner). For example, the control system can include a flow control mechanism to manipulate a flow path at the junction to draw fluid from the first reservoir alone, the second reservoir alone, or both first and second reservoirs in an alternating manner.

The first reservoir may be referred to as the primary source and the second reservoir may be referred to as the secondary source. During a primary infusion, fluid is infused from the first, or primary reservoir, into the junction, and through the common line to the terminal end (and into the patient) at a first infusion rate. During a secondary infusion, fluid is infused from the second, or secondary reservoir, into the junction, and through the common line to the terminal end (and into the patient) at a second infusion rate. During a concurrent infusion (sometimes referred to as concurrent delivery), first and second fluids are infused simultaneously to a patient at respective first and second infusion rates. A first volume of the first fluid is drawn from the first reservoir, and a second volume of the second fluid is drawn from the second reservoir. The first and second volumes are proportionate to the first and second infusion rates. Once the first and second fluids have been drawn, the pump drives (e.g., pumps or pushes out) the fluid combination through the common line to the terminal and (and into the patient) at a combined rate.

The combined rate can be equal to one of the first or second infusion rates, or it can be determined from the first and second infusion rates. For example, the combined rate can be determined as the sum as the first and second infusion rates. In some cases, a maximum rate may be established, and if the sum of the programmed first and second rates exceeds the maximum rate, then the combined rate may be set to the maximum rate. Other methods of determining a combined rate using the first and second rates are possible, as well. In addition, if the combined rate equals or exceeds a predetermined maximum combined rate, the first and second rates may be reduced proportionally such that their sum is less than or equals the maximum combined rate. In other embodiments, if the combined rate equals or exceeds a predetermined maximum combined rate, only the first rate is reduced until the sum of the first and second rates is less than or equals the maximum combined rate. For example, only the first rate may be reduced based upon a determination of fluid types of the first and second fluids. If the first fluid is a non-medication and the second fluid is a medication, then in some embodiments, the only the first rate is reduced (or the first rate is reduced by an amount or proportion that is greater than an amount or proportion that the second rate is reduced), such that the sum of the first and second rates is less than or equal to the maximum combined rate. In such embodiments, the user would be presented with a suggested first and second rate for approval or confirmation via a user interface before changing and/or initiating an infusion according to such adjusted first and/or second rates.

BRIEF DESCRIPTION OF THE DRAWINGS

Like elements share like reference numbers throughout the various figures.

DETAILED DESCRIPTION

Systems and methods that improve an infusion pump system with concurrent delivery and common line auto flush are described herein. An infusion pump can operate in a primary delivery mode and deliver a first fluid from a first reservoir at a first rate, and then switch to a concurrent delivery mode, such as by delivering a combination of the first fluid from the first reservoir and a second fluid from a second reservoir at a combined delivery rate. The pump may switch from a concurrent delivery mode to a primary delivery mode (or to a secondary delivery mode where a second fluid is delivered from a second reservoir at a second rate), as well.

As discussed above, first fluid will remain in the common line at the time the delivery mode is switched from primary delivery mode to concurrent delivery mode. Therefore, if the first and second fluids are delivered at the combined delivery rate as soon as the concurrent delivery mode begins, the first fluid remaining in the common line will be delivered into the patient at the incorrect (i.e., the combined) rate. Furthermore, delivering fluids at rates other than the desired rates may result in inaccurate therapy, which can be dangerous to the patient. The systems and methods described herein improve delivery and accurately account for the fluid remaining in the volume of the common line. Fluid as used herein can be any fluid suitable to be administered to a patient by infusion, including saline fluid, fluid including a drug or other therapeutic agent, or the like.

Figure 1A:
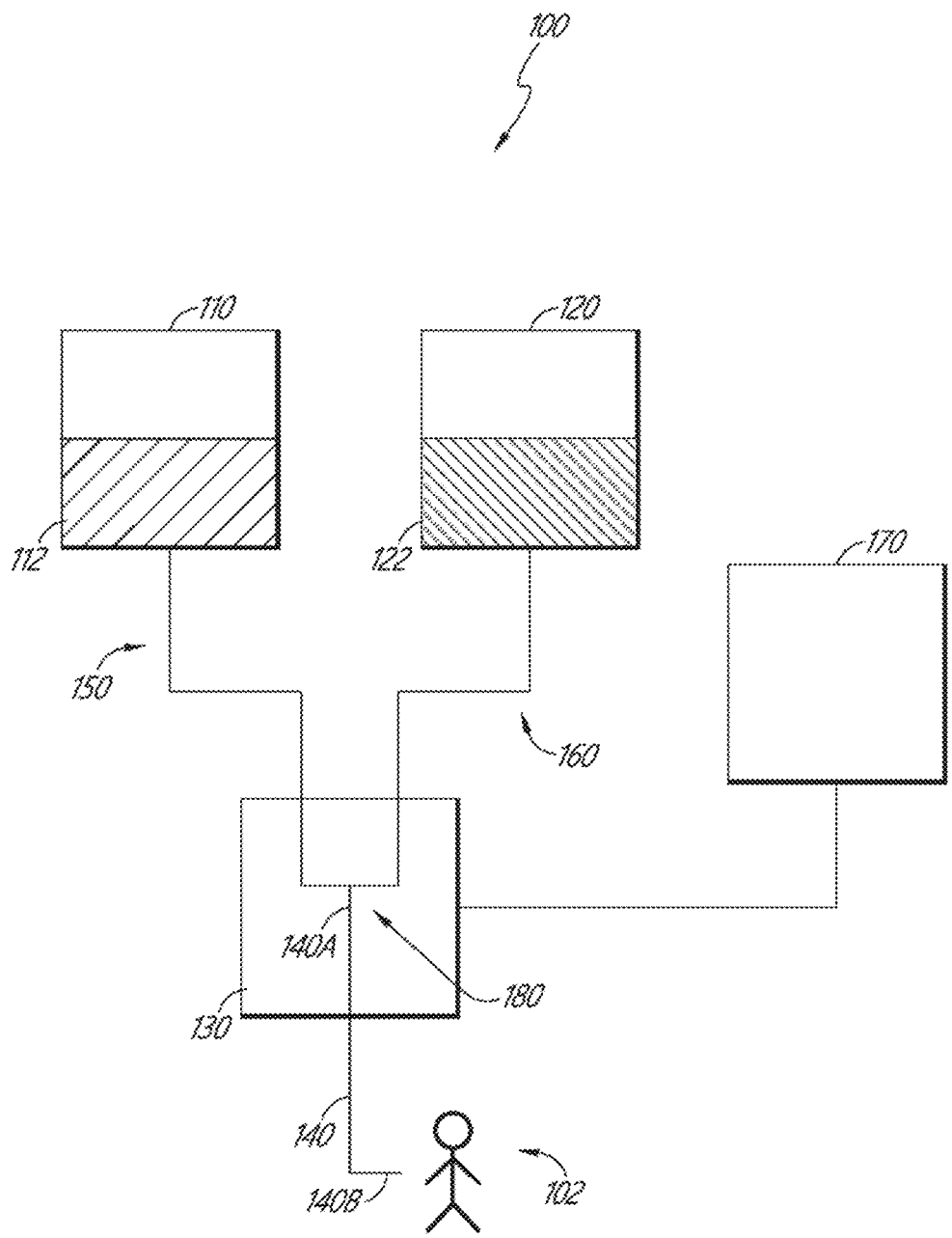
FIGS. 1A and 1B are block diagrams of infusion pump systems with concurrent fluid delivery and common line auto flush in accordance with the present invention.
Figure 1B:
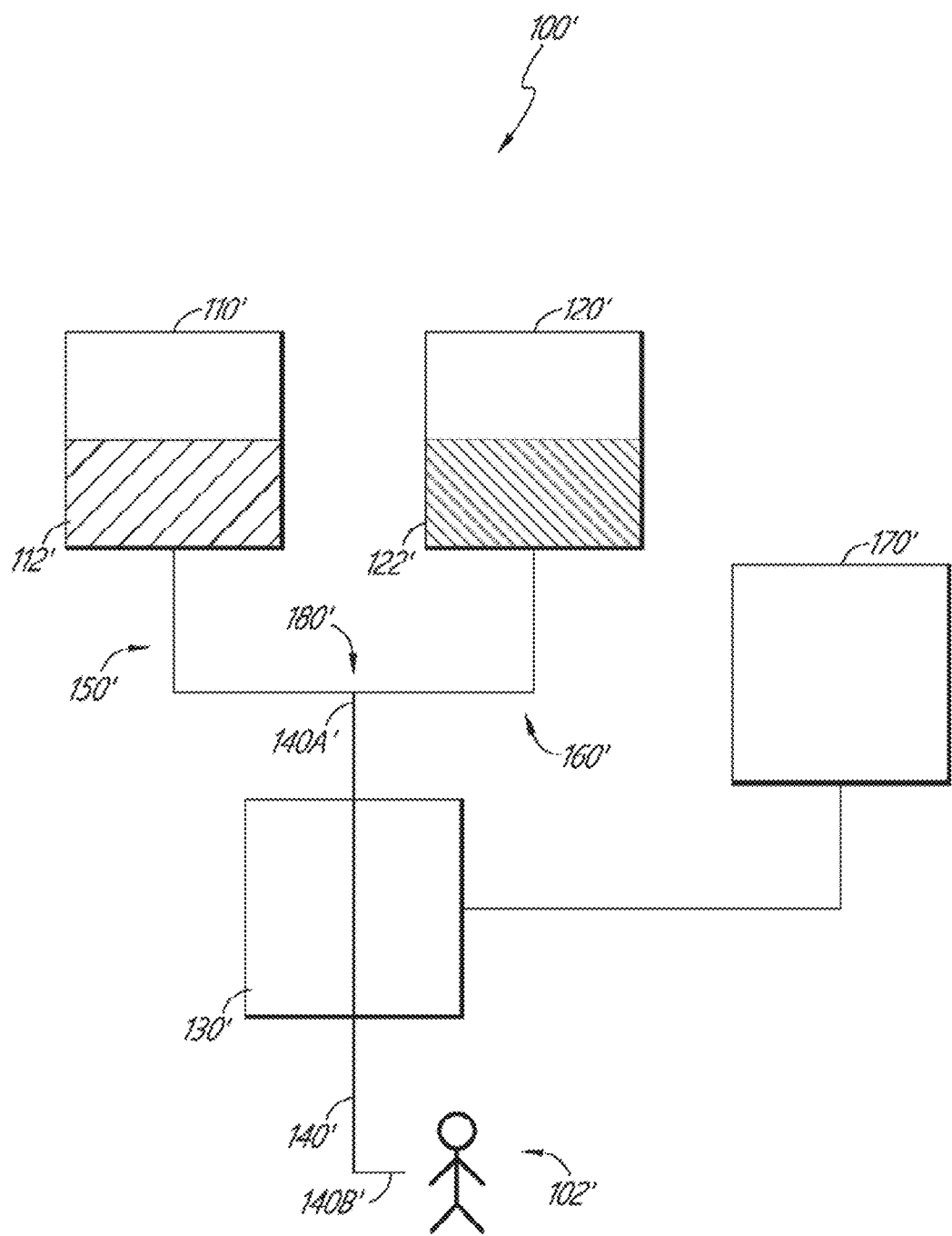

FIGS. 1A & 1B are block diagrams for embodiments of infusion pump systems with concurrent delivery and a common line. The infusion pump system illustrated in FIG. 1A includes a junction in fluid communication with the first reservoir and the second reservoir. An optional mixing chamber is located at the junction, or between the junction and the common line. The junction and/or mixing chamber is located internal to the infusion pump. In the embodiment of the infusion pump system illustrated in FIG. 1B a junction in fluid communication with the first reservoir and the second reservoir is located external to the infusion pump. An optional mixing chamber is located at the junction, or between the junction and the common line. The location of the junction, in part, determines the length and internal volume of the common line between the junction and the terminal fluid delivery end. The internal cross-sectional shape, which is usually substantially circular, and the diameter and length of the common line determine its internal volume. Other shapes can be used without detracting from the scope of the disclosure.

The infusion pump system 100 of FIG. 1A includes a junction 180 internal to the infusion pump 130 and an optional mixing chamber (not shown) at the junction or between the junction 180 and a common line 140. The infusion pump system 100 includes a first reservoir 110 that contains a first fluid 112; a second reservoir 120 that contains a second fluid 122; a junction 180 in fluid communication with the first reservoir 110 and the second reservoir 120; an optional mixing chamber (not shown); a common line 140 in fluid communication with the mixing chamber and/or the junction 180 at one end 140A and having a terminal fluid delivery end 140B for connection to the patient 102, and an infusion pump 130 operable to drive fluid through the common line 140.

Primary Infusion Mode

The infusion pump 130 is operable to operate in a primary infusion mode during which the infusion pump infuses the first fluid 112 at a first rate along a first flow path 150 that includes the first reservoir 110, the junction 180, the optional mixing chamber, and the common line 140. The infusion pump 130 is further operable to determine a common line flush volume value corresponding to the internal volume of the common line 140. The infusion pump 130 may determine the common line flush volume by receiving the value from an operator, receiving it over a network (e.g., from a drug library or other database), retrieving it from a memory of the infusion pump, or any other method described herein.

Primary to Concurrent Infusion Mode with Auto Flush

The infusion pump 130 is further configured to change to a concurrent infusion mode by drawing a second fluid 122 from a second reservoir 120 along a second flow path 160 into the junction 180 and/or mixing chamber and mixing it with the first fluid 112, drawn from the first reservoir 110 via the first flow path 150. The second flow path 160 includes the second reservoir 120, the junction 180, and the optional mixing chamber. The infusion pump is configured to initially infuse the mixture at the first rate until the volume of the first fluid is flushed out of the common line 140. The infusion pump 130 is configured to monitor volume of the mixture of first and second fluids 112, 122 driven at the first rate and subsequently pump the mixture of first and second fluids 112, 122 at the programmed combined rate when the monitored volume of the mixture is equal to or greater than the common line flush volume value. In this case, the delivery rates of fluid 1 and fluid 2 would be reduced (scaled down) from programmed rates during displacement of the common line volume, and the pump system may allow an override of one or both lower rate limits, or other associated limits, defined respectively for each of fluid 1 and fluid 2, during this phase of delivery.

Alternatively, for example in a scenario where the first fluid is a not a medication (e.g., saline) and it is desired to initiate delivery of the second fluid (that is a medication) rapidly, the infusion pump could be configured to initially infuse the mixture at a more rapid rate to quickly displace the relatively inert common line volume. In this case, the initial combined rate could be increased (scaled up) to the programmed first rate plus the programmed second rate until the monitored volume of the mixture is equal to the common line flush volume. In this case, the delivery rates of fluid 1 and/or fluid 2 may be increased above upper rate limits defined for those respective fluids and the pump system may allow override of those limits during this phase of delivery. Further, the resulting scaled combined rate will be applied to the common line fluid 1, whose upper rate limit may limit or define allowable increased combined rates during the common line displacement phase. In this case, drug library defined limits would be considered and applied by the pump system at the point of infusion to the patient as well as per pump programming activity.

Concurrent to Primary Infusion Mode with Auto Flush

The infusion pump 130 is further configured to change from concurrent delivery to a primary infusion mode by refraining from drawing the second fluid 122 from the second reservoir 120, and by infusing only the first fluid 112 from the first reservoir 110 along the first flow path 150. When the infusion pump switches to primary infusion mode, the infusion pump is configured to initially drive the first fluid 112 at the combined rate until the volume of the mixture of first and second fluids 112, 122 is flushed out of the common line 140. The infusion pump 130 is configured to monitor volume of the first fluid 112 driven at the combined rate and subsequently pump the first fluid 112 at the first rate when the monitored first fluid volume is equal to or greater than the common line flush volume value. In one example, the infusion pump 130 can be a fluid displacement pump employing a cassette, such as the Plum 360™ infusion pump available from ICU Medical, Inc. of San Clemente, CA Those skilled in the art will appreciate that the infusion pump 130 can be any type of pump operable to drive fluid from two reservoirs through a common line 140. In this case, driving of the first fluid at the combined rate during common line displacement may require that the pump system allows override of drug library-defined upper rate limits for the first fluid.

Concurrent to Secondary Infusion Mode with Auto Flush

In another embodiment, the infusion pump 130 is further configured to change from a concurrent delivery to a secondary infusion mode by refraining from drawing the first fluid 112 from the first reservoir 110, and by infusing only the second fluid 122 from the second reservoir 120 along the second flow path 160. For example, if the first fluid 112 infusion is completed or is stopped, the infusion pump 130 may automatically switch to a secondary infusion mode. In such case, the infusion pump 130 will stop drawing first fluid 112 from the first reservoir 110, and it will continue to pump at the combined rate until the common line is cleared of the fluid mixture. In this case, the pump system may need to allow an override of upper rate limits for the second fluid while it is pumped at the combined rate during common line displacement. The infusion pump 130 is configured to monitor volume of the second fluid 122 driven at the combined rate and subsequently pump the second fluid 122 at the second rate when the monitored second fluid volume is equal to or greater than the common line flush volume value.

In one embodiment, the infusion pump 130 can be operably connected to a medication management unit (MMU) 170 or a server over a hospital network and/or the Internet, to receive a drug library (or other database), which may specify an appropriate common line flush volume value. For example, the drug library (or other database) may include information regarding the volume of various tubing assemblies, each tubing assembly including a common line. The infusion pump (or server) may be configured to determine a tubing assembly identifier associated with a tubing assembly that is attached to the infusion pump and the patient 102. The infusion pump may determine the tubing assembly identifier by receiving it from a server over the hospital network and/or the Internet, by receiving it via manual data entry by an operator, and/or by reading the tubing assembly identifier from the tubing assembly (or by other methods). For example, a tag, such as an RFID tag, an NFC tag or other wireless tag, may include the tubing assembly identifier. A tag reader incorporated into or in communication (directly or indirectly) with the infusion pump, may read the tag to determine the tubing assembly identifier. The common line flush volume value may be determined using the tubing assembly identifier and the drug library (or database).

In one embodiment, the infusion pump 130 can be further operable to increment a displayed value of first fluid volume by the monitored volume when the mixture of first and second fluids 112, 122 are driven at the first rate. The infusion pump 130 can be further operable to increment a displayed value of first and second fluid volumes when the first fluid 112 is driven at the combined rate. In one embodiment, the infusion pump 130 is operable to monitor the volume of infused first fluid 112 and switch to a concurrent infusion mode when the volume of the infused first fluid is equal to a Volume To Be Infused (VTBI) for the first fluid or when the volume of the infused first fluid is equal to the VTBI for the first fluid minus the volume of the common line. In one embodiment, the infusion pump 130 is operable to monitor the volume of infused second fluid 112 during a concurrent infusion mode and switch to a primary infusion mode when the volume of the infused second fluid is equal to a Volume To Be Infused (VTBI) for the second fluid or when the volume of the infused second fluid is equal to the VTBI for the second fluid minus the volume of the common line.

The infusion pump 130 can be operable to receive the common line flush volume value for the common line 140 automatically from the drug library stored in a memory locally in the infusion pump system 100 or remotely on a server. In one example, the drug library associates the common flush volume value with a particular therapeutic agent. In some cases, the drug library may include an indication (e.g., a flag, value, etc.) that a particular fluid is a rate dependent medicinal fluid whose action is rate dependent. The infusion pump 130 may be configured to infuse such fluids (whether alone or concurrently with a second fluid) at the infusion rate specified for such fluids. In another example, the drug library associates the common flush volume value with a particular clinical care area (CCA), such as general care, an intensive care unit (ICU), a neonatal ICU, or the like. In yet another example, the drug library associates the common flush volume value with a particular consumable infusion set, which provides the common line volume. The drug library can include upper and lower dosing limits with hard and soft limits for a number of therapeutic agents. In another embodiment, the infusion pump 130 can be operable to receive the common line flush volume value for the common line 140 from a caregiver via an input on a user interface of the infusion pump.

The common line 140 as illustrated includes the line between the junction 180 and the terminal fluid delivery end 140B that is generally connectable to the patient 102 and includes any fluid path common to the first flow path 150 and the second flow path 160. Thus, the common line 140 can include flow paths within the infusion pump 130 (including the associated consumable infusion set, when applicable) common to the first flow path 150 and the second flow path 160, and is not limited to tubing external to the infusion pump 130. The common line 140 is any portion of the infusion pump system 100 through which the first fluid 112 or a combination of the first fluid 112 and the second fluid 122 can alternately flow when switched. In one embodiment, the common line flush volume value is an internal volume of the common line 140. The common line flush volume value can include an associated consumable infusion set volume, extension sets, filters, stopcocks, manifolds, patient access devices, catheters, and the like. In another embodiment, the common line flush volume value is an internal volume of the common line 140 plus an adjustment volume. The adjustment volume can be any volume desired as a safety factor to assure that the common line 140 is free of the first fluid 112 before the second fluid 122 is infused at the second rate.

The infusion pump system 100' of FIG. 1B has a junction 180' external to the infusion pump 130' and an optional mixing chamber (not shown) at the junction 180' or between the junction 180' and a common line 140'. The infusion pump system 100' includes a first reservoir 110' containing a first fluid 112'; a second reservoir 120' containing a second fluid 122'; a junction 180' in fluid communication with the first reservoir 110' and the second reservoir 120'; an optional mixing chamber (not shown); a common line 140' in fluid communication with the mixing chamber and/or the junction 180' at one end 140a' of the common line 140' and a terminal fluid delivery end 140B' that is generally connectable to the patient 102', and an infusion pump 130' operable to drive fluid through the common line 140'. The infusion pump 130' is operable to: infuse the first fluid 112' at a first rate along a first flow path 150' including the first reservoir 110', the junction 180', the optional mixing chamber, and the common line 140'; determine a common line flush volume value for the common line 140'. The infusion pump 130' may determine the common line flush volume by receiving the value from an operator, receiving it over a network (e.g., from a drug library or other database), retrieving it from a memory of the infusion pump, or any other method described herein.

The infusion pump 130' is further configured to change to a concurrent infusion mode by drawing a second fluid from a second reservoir 120' along a second flow path 160' into the optional mixing chamber and mixing it with the first fluid, drawn from the first reservoir 110' via the first flow path 150'. The second flow path 160' includes the second reservoir 120', the junction 180', and the optional mixing chamber. The infusion pump is configured to initially infuse the mixture at the first rate until the volume of the first fluid is flushed out of the common line 140'. The infusion pump 130' is configured to monitor volume of the mixture of first and second fluids 112', 122' driven at the first rate and subsequently pump the mixture of first and second fluids 112', 122' at a combined rate when the monitored volume is equal to or greater than the common line flush volume value.

The infusion pump 130' is further configured to change to a primary infusion mode by refraining from drawing the second fluid 122' from the second reservoir 120', and by infusing only the first fluid 112' from the first reservoir 110' along the first flow path 150'. When the infusion pump 130' switches to primary infusion mode, the infusion pump 130' is configured to initially infuse the first fluid 112' at the combined rate until the volume of the mixture of first and second fluids 112', 122' is flushed out of the common line 140'. The infusion pump 130' is configured to monitor volume of the first fluid 112' driven at the combined rate and subsequently pump the first fluid 112' at the first rate when the monitored volume is equal to or greater than a common line flush volume value. The infusion pump 130' is further configured to determine the common line flush volume value according to any of the methods described herein.

In one embodiment, the junction 180' can include a two-way valve to manually or automatically switch the infusion pump system 100' between the first flow path 150' and the second flow path 160'. In one example, the infusion pump 130' can be a peristaltic pump. Those skilled in the art will appreciate that the infusion pump 130' can be any type of pump operable to drive fluid through the common line 140'.

Figure 2:
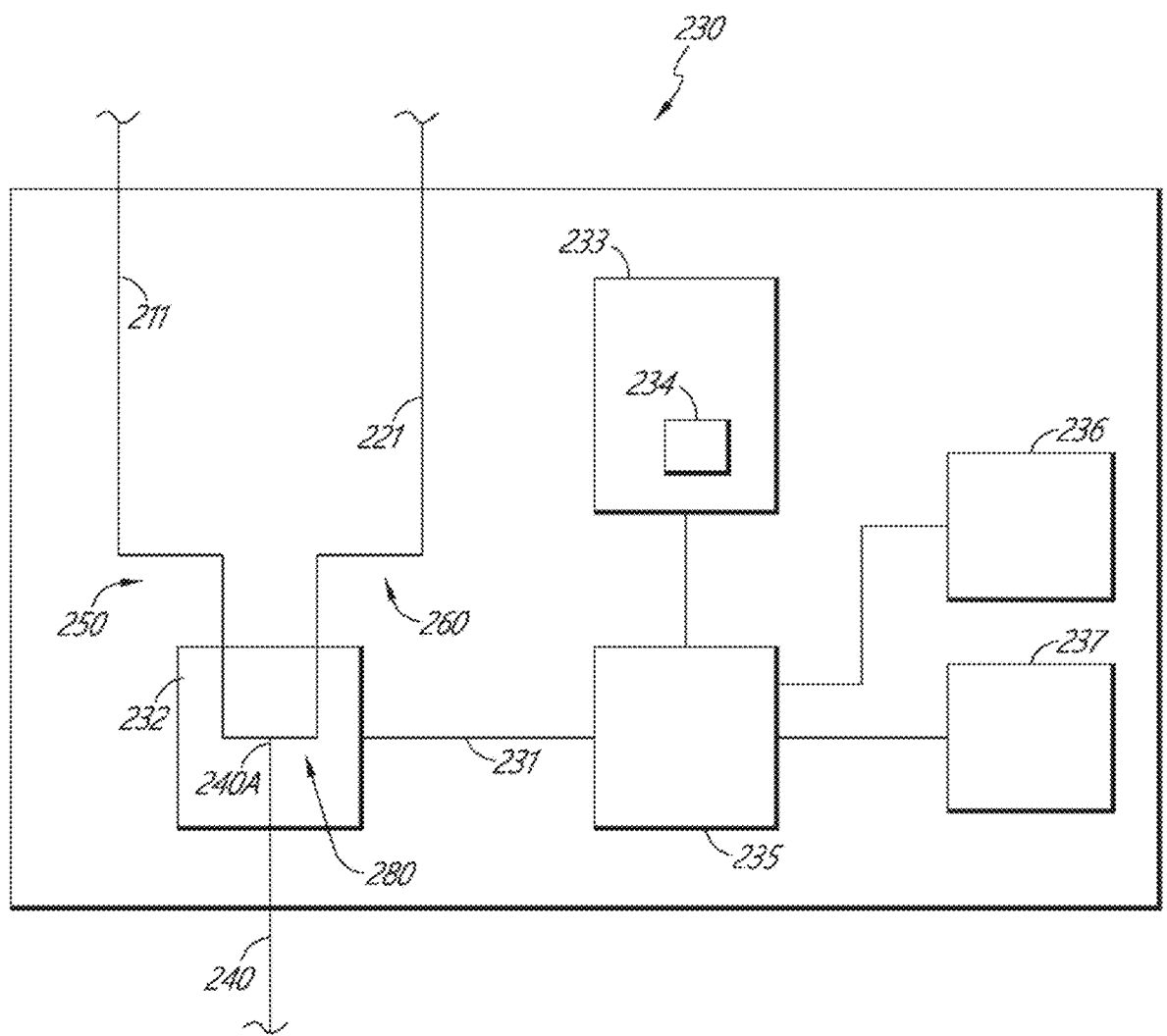
FIG. 2 is a block diagram of an infusion pump with concurrent fluid delivery and common line auto flush in accordance with the present invention.

FIG. 2 is a block diagram of an embodiment of an infusion pump with concurrent fluid delivery and common line auto flush. The infusion pump 230 is operably connected to a common line 240 in fluid communication with a junction 280 and/or mixing chamber at one end 240A and having a terminal fluid delivery end 240B (not shown), the junction 280 being in fluid communication with a first reservoir (not shown) containing a first fluid and a second reservoir (not shown) containing a second fluid. In this example, a first reservoir line 211 provides fluid communication between the first reservoir and the junction 280 and a second reservoir line 221 provides fluid communication between the second reservoir and the junction 280.

The infusion pump 230 includes a memory 233 operable to store programming code; a flow controller 235 operably connected to the memory 233; and a fluid driver 232 operably connected to receive a control signal 231 from the flow controller 235, the fluid driver 232 being operable to drive fluid through the common line 240. The flow controller 235 is operable to execute the programming code and provide the control signal 231 to the fluid driver 232 in response to the programming code. The fluid driver 232 is responsive to the control signal 231 to infuse the first fluid at a first rate along a first flow path 211 including the first reservoir, the junction 280, and the common line 240; receive a common line flush volume value associated with the common line 240; switch from infusing only the first fluid via the first flow path 250 to infusing a combination of the first fluid from the first reservoir and a second fluid from the second reservoir; drive the fluid combination at the first rate; monitor volume of the fluid combination driven at the first rate; and drive the fluid combination at a combined rate when the monitored volume is equal to or greater than the common line flush volume value. The fluid driver 232 is also responsive to the control signal 231 to infuse the fluid combination at the combined rate; switch to infusing only the first fluid via the first flow path 250; drive the first fluid at the combined rate; monitor the volume of the first fluid driven at the combined rate; and drive the first fluid at the first rate when the monitored volume is equal to or greater than the common line flush volume value. The combined rate may be retrieved from the memory 233 or determined from a first infusion rate associated with the first fluid and a second infusion rate associated with the second fluid. For example, the combined rate may be determined as the sum of the first and second infusion rates.

In an embodiment, the flow controller 235 monitors the volume based on a time elapsed and a rate of delivery. The flow controller 235 can also monitor volume based on measurements, such as number of turns of a motor or signals from a sensor.

The flow controller 235 can include a hardware processor, microprocessor, or the like responsive to the programming code to generate the control signal 231. The fluid driver 232 can include a metered pump, such as a cartridge pump, peristaltic pump, or the like, operable to drive fluid at a desired rate in response to the control signal 231. In one embodiment, the fluid driver 232 can be further responsive to the control signal 231 to increment a displayed first fluid volume by the monitored volume when the fluid combination is driven at the first rate or when the monitored volume is equal to or greater than an internal volume of the common line 240. The fluid driver 232 can be further responsive to the control signal 231 to increment displayed first and second fluid volumes as the first fluid is driven at the combination rate or when the monitored volume is equal to or greater than the internal volume of the common line 240. The first fluid displayed volume and/or the second fluid displayed volume can be displayed on a user interface 236.

The memory 233 can also be operable to store data and other information, such as a drug library 234 (or other database) including the common flush volume value, which can optionally be associated with a particular therapeutic agent, a particular clinical care area, and/or a particular consumable infusion set. Different therapeutic agents may have different fluid properties and thus it may be advantageous in some embodiments to associate particular common flush volume value with particular therapeutic agents. In one embodiment, the infusion pump 230 can receive the common line flush volume value for the common line 240 automatically from the drug library 234. In another embodiment, the infusion pump 230 can receive the common line flush volume value manually via direct entry of the value on a user interface 236. The manual entry can be accomplished using a manufacturer provided volume value based upon the length and internal diameter of the common line 240 or a list number or other identifier that is used to access an associated volume value from a lookup table in the pump memory 233, drug library, stored in a network location, at a server, or MMU. The possibility for manual typographical errors can be reduced by use of a barcode, radio frequency (RFID), optical, touch memory reader, near field communicator, or the like to input or scan a machine readable identifier on the infusion set, common line, or its package to obtain the volume value, the list number or other identifier associated with the volume value.

The infusion pump 230 can include human and/or machine interfaces as desired for a particular application. A user interface 236 operably connected to the flow controller 235 can provide input from and/or output to a caregiver or other user to the infusion pump 230. Exemplary user interfaces can include display screens, soft keys or fixed keys, touchscreen displays, and the like. An I/O interface 237 operably connected to the flow controller 235 can provide input from and/or output to hardware associated with the infusion pump 230. Exemplary I/O interfaces can include a wired and/or wireless interface to an electronic network, medication management unit (MMU), medication management system (MMS), or the like.

The common line flush volume value can be selected as desired for a particular application. The common line 240 includes the line between the junction 280 and the terminal fluid delivery end 240B, and includes any fluid path common to the first flow path 250 and the second flow path 260 and so can include any portion of the infusion pump 230 (including the associated consumable infusion set) through which the first fluid or the second fluid can alternately flow or flow in a combined manner. In one embodiment, the common line flush volume value is equal to the internal volume of the common line 240, so that the second fluid is infused at the second rate along the second flow path as soon as the first fluid has been cleared from the common line 240. In another embodiment, the common line flush volume value is equal to the internal volume of the common line 240 plus an adjustment volume (to take into account the added/subtracted volume of other connectors or components), so that the second fluid is infused at the second rate along the second flow path after the first fluid has been cleared from the common line 240 plus the adjustment volume of the second fluid has been delivered at the first rate. In another embodiment, the common line flush volume value is equal to the internal volume of the common line modified by a percentage, which could provide a desired overage or underage. The adjustment volume can be used as a safety factor to assure that the common line 240 is free of the first fluid before the second fluid is infused at the second rate.

Figure 3:
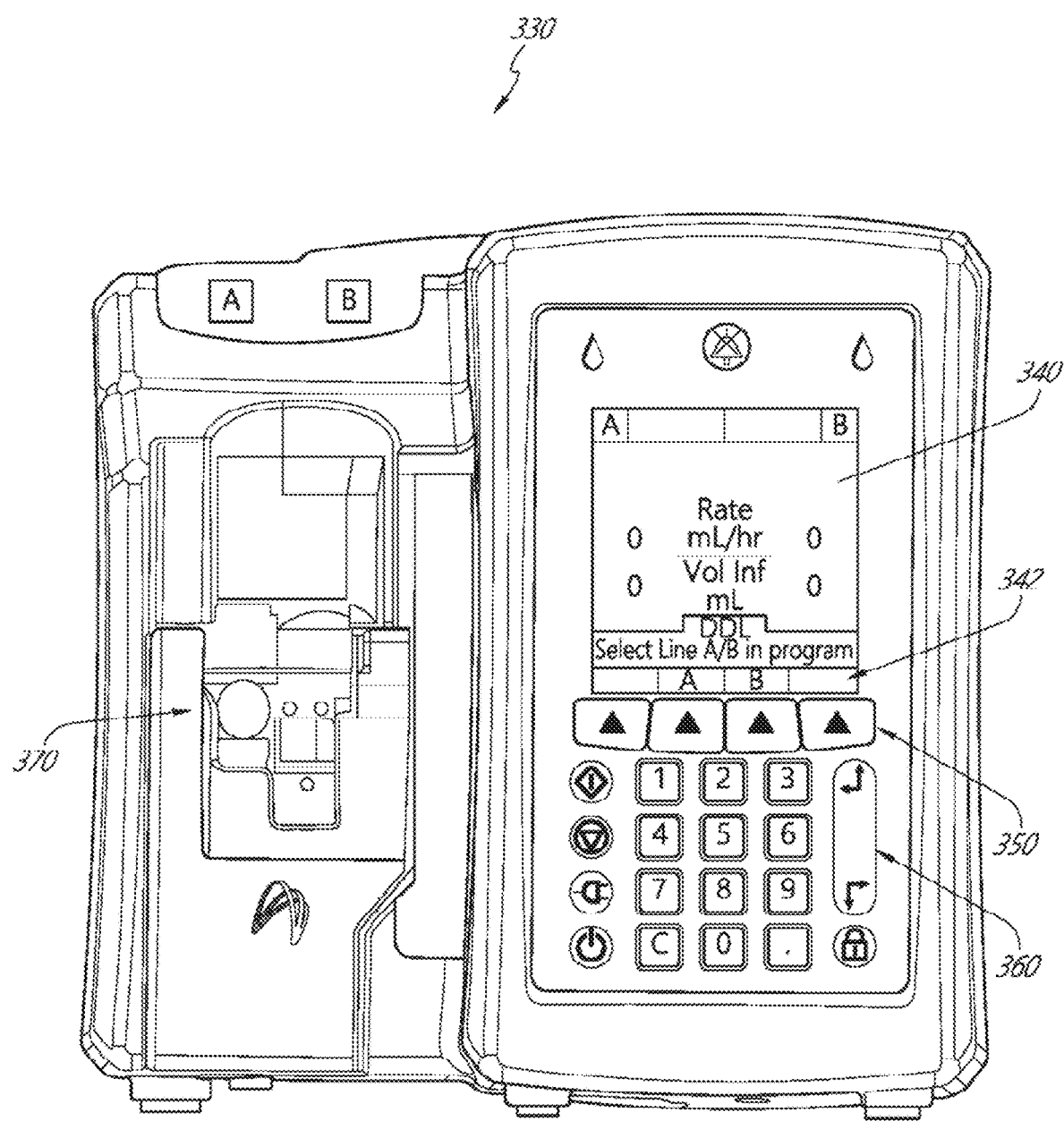
FIG. 3 is a schematic diagram of an infusion pump with concurrent fluid delivery and common line auto flush in accordance with the present invention.

FIG. 3 is a schematic diagram of an infusion pump with common line auto flush in accordance with the present invention. In this example, the infusion pump 330 includes a display 340, soft keys 350, and fixed keys 360 as a user interface. The display 340 provides operational and/or programming information to the user. The soft keys 350 perform different functions depending on the command displayed on an adjacent command portion 342 of the display 340. The fixed keys 360 are labeled with an input or function which functions the same, regardless of whatever is displayed on the display 340. In this example, the infusion pump 330 also includes a pump mechanism 370 operable to communicate with the first reservoir line and the second reservoir line and to move the first fluid or the second fluid to the terminal fluid delivery end of the common line.

Figure 4A:
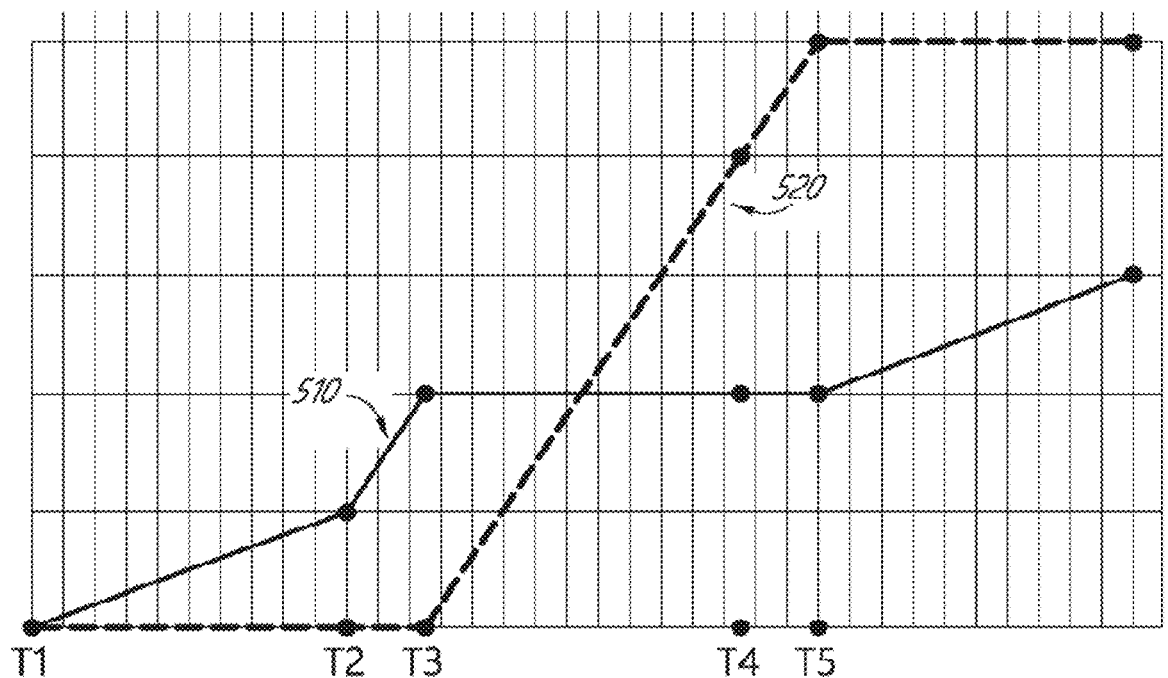
FIGS. 4A and 4B are graphs of fluid volume delivered at the terminal fluid delivery end of the common line versus time for a method of use for an infusion pump with concurrent fluid delivery and common line auto flush in accordance with the present invention.
Figure 4B:
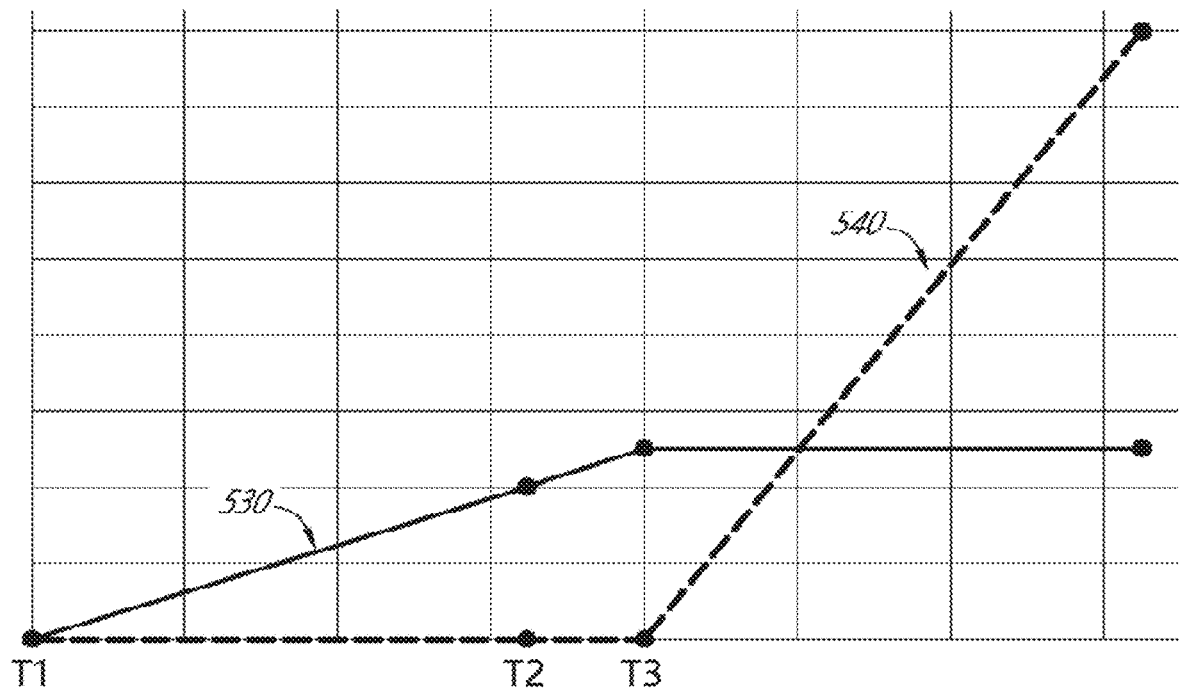

FIGS. 4A & 4B are graphs of fluid volume delivered at the terminal end of the common line or patient versus time for a method of use for an infusion pump with common line auto flush in accordance with the present invention.

Referring to FIG. 4A, graph 510 is the fluid volume delivered at the terminal fluid delivery end of the common line for a first fluid versus time and graph 520 is the fluid volume delivered at the terminal fluid delivery end of the common line for a mixture of the first fluid and a second fluid versus time. From T1 to T2, the first fluid is infused at a first rate along a first flow path including the first reservoir and the second fluid is not infused. From T2 to T3, the first fluid is infused at a flushing rate greater than the first rate as a mixture of first and second fluids are drawn from first and second reservoirs, respectively, into the junction and/or mixing chamber and driven out at the flushing rate. For example, if the first fluid is a non-medicinal fluid (e.g., a saline solution, etc.), it may be desirable to flush the first fluid from the common line at an increased rate in order to infuse the second fluid into the patient as soon as possible. The flushing rate can be equal to the combined first rate plus second rate (as shown) or it can be determined by increasing the combined rate (e.g., the first rate plus the second rate by a flushing factor (e.g., 10%, 20%, 50%, 100%, etc.). The second fluid cannot be infused (e.g., it will not enter the patient) until the internal volume of the common line is cleared of the first fluid. From T3 to T4, the internal volume of the common line has been cleared of the first fluid and beginning at T3 the mixture of the first and second fluids are infused into the patient at a combined rate. From T4 to T5, auto flush is performed: the mixture of the first fluid and the second fluid is infused into the patient at the combined rate as only the first fluid is drawn into the junction and/or mixing chamber and driven out at the combined rate until the internal volume of the common line is cleared of the first and second fluid mixture. The first fluid cannot be infused by itself (e.g., it cannot enter the patient without the second fluid) until the internal volume is cleared of the first and second fluid mixture. After T5, the first fluid is infused at the first rate along the first flow path including the first reservoir after the internal volume of the common line has been cleared of the first and second fluid mixture. In this example, no additional second fluid is infused after T5, although in other embodiments, additional concurrent infusions (of first and second fluid mixtures) and/or secondary infusions (of just the second fluid) may be programmed to occur, as well.

Those skilled in the art will appreciate that the transition between the two infusion modes can be selected as desired for a particular application. In the example of FIG. 4A, a common line auto flush is performed from T4 to T5, but not from T2 to T3. As long as the common line flush volume value is known, the common line auto flush maintaining the first rate between T2 and T3 can be performed as desired.

Referring to FIG. 4B, graph 530 is the fluid volume delivered at the terminal fluid delivery end of the common line for a first fluid versus time and graph 540 is the fluid volume delivered at the terminal fluid delivery end of the common line for a mixture of the first fluid and a second fluid versus time. From T1 to T2, the first fluid is infused at the first rate along a first flow path including the first reservoir and the second fluid is not infused. From T2 to T3, auto flush occurs and the first fluid is infused at the first rate as a mixture of first and second fluids are drawn from first and second reservoirs, respectively, into a junction and/or mixing chamber, and driven out at a combined rate (as discussed above). The first fluid is infused, driven or displaced until the internal volume of the common line has been cleared of the first fluid. After T3, the mixture of the first and second fluids is infused, driven or displaced at the combined rate (as discussed above) after the internal volume of the common line has been cleared of the first fluid. In one embodiment, the common line is cleared of the first fluid when the monitored volume of the mixture of the first and second fluids driven at the first rate between T2 and T3 is equal to or greater than the common line flush volume value. In this example, no additional second fluid is infused after T3, although in other embodiments, additional concurrent infusions (of first and second fluid mixtures) and/or secondary infusions (of just the second fluid) may be programmed to occur, as well.

Concurrent Delivery with Common Line Auto Flush

Figure 5A:
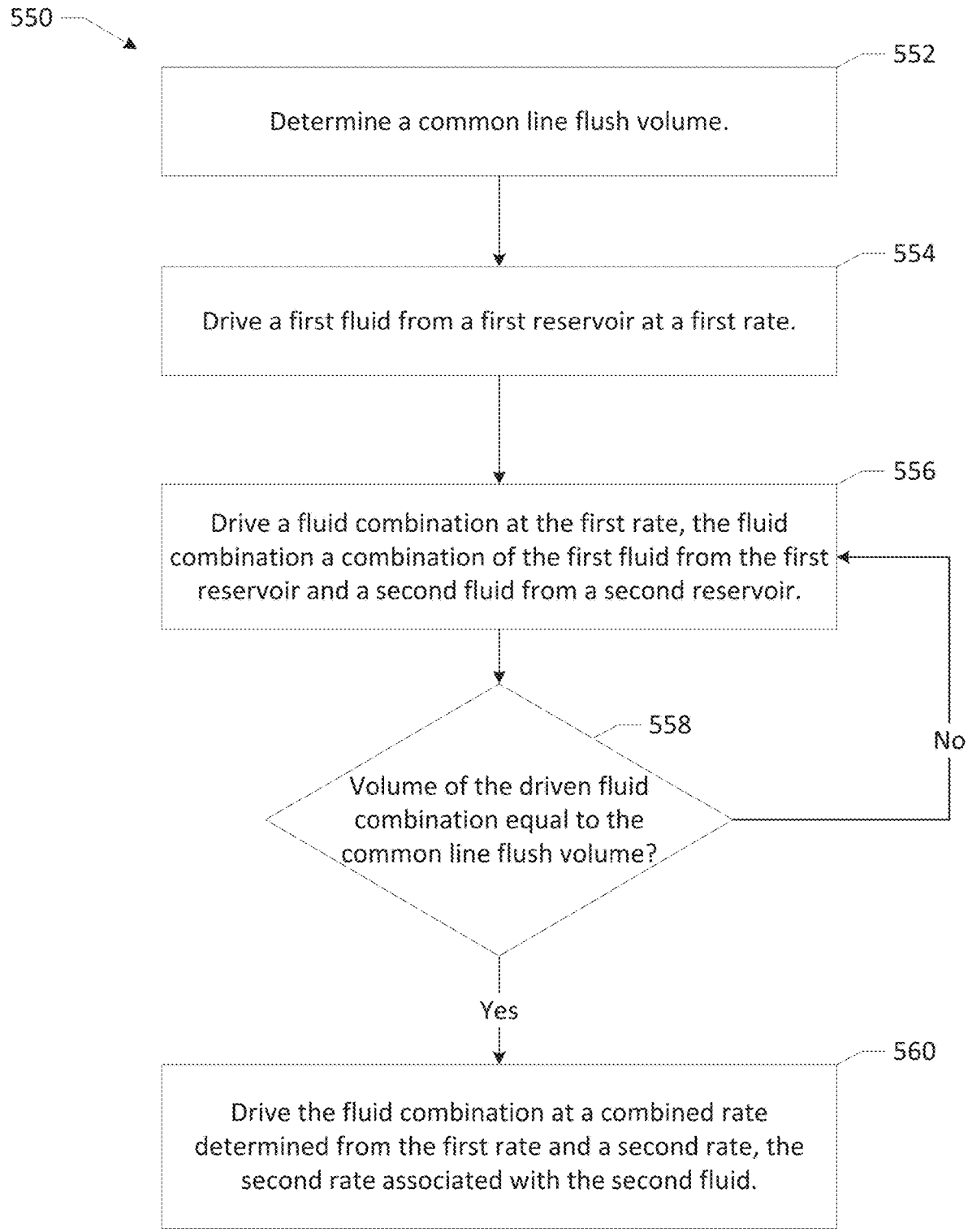
FIG. 5A is a flowchart of a method of concurrent fluid delivery and common line auto flush in accordance with the present invention that may be performed by the infusion pumps of FIGS. 1-3.

FIG. 5A is a flowchart of an embodiment of a method for concurrent infusion with common line auto flush. The method 550 can be performed with any infusion pump system described herein. In one embodiment, the infusion pump system includes a first reservoir containing a first fluid, a second reservoir containing a second fluid, a junction in fluid communication with the first reservoir and the second reservoir, an optional mixing chamber at or in fluid communication with the junction, and a common line in fluid communication with the junction and/or mixing chamber at one end and having a terminal fluid delivery end, and an infusion pump operable to drive fluid through the common line. The method 550 can be performed by any of the systems discussed herein. In an embodiment, some or all aspects of the method 550 are stored as programmed instructions to be executed by an infusion pump flow controller (e.g., flow controller 235). The method 550 can be used with an infusion pump system and infusion pump as described in FIGS. 1A, 1B, & 2 above. A drug library may include an indication (e.g., flag, value, etc.) to enable or disable concurrent infusion with auto flush, as described with respect to FIG. 5A. In this example, the infusion pump infuses a first fluid on a first flow path at a first rate and switches to a concurrent infusion mode during which it infuses a mixture of the first fluid and a second fluid, maintaining the first rate long enough to clear the remaining first fluid from the common line before changing to a combined rate for infusing the mixture of the first and second fluids.

Referring to FIG. 5A, at block 552, the flow controller 235 determines a common line flush volume value. As discussed above, the common line flush value can be received based on a user input via any of the user interfaces discussed above. In an embodiment, the flow controller 235 can automatically retrieve the common line flush volume value from the memory 233 or over a network (e.g., from a drug library or other database), or by wirelessly reading information from a tag associated with the common line and using the information to retrieve the common line flush volume from the memory or over the network. The common line flush volume may be predetermined for particular fluids. The common line flush volume may also depend on the VTBI or rate of the infusion.

At block 554, a first infusion mode to infuse the first fluid at a first infusion rate begins. The first fluid is infused or driven at a first infusion rate along a first flow path that includes the first reservoir, the junction, the optional mixing chamber, and the common line. The infusion of the first fluid can be controlled by the flow controller 235 based on a control signal to activate the pump or other mechanical system. In some embodiments, the infusion of the first fluid can also be based on a user input or user control of the pump or the mechanical system. During the first infusion mode, the infusion pump drives the first fluid from the first reservoir at the first infusion rate. At block 556, the flow controller 235 can determine to switch from the first infusion mode to a concurrent infusion mode. During an auto flush period, at block 556, the infusion pump drives a mixture or combination of the first fluid and the second fluid toward the common line at the first rate. By driving the combination of the first and second fluids at the first rate, the first fluid remaining in the common line is flushed and delivered to the patient at the same rate as therapeutically required. In some embodiments, during the auto flush period, the infusion pump drives the combination of the first fluid and the second fluid at a combined rate, instead of the first rate. For example, it may be advantageous to use a combined rate to more quickly flush the common line, particularly when the fluid being flushed from the common line is a non-medicinal fluid, such as saline, or other non-medicinal fluid. The combined rate can be determined using any of the methods described herein. For example, the combined rate may be determined as the sum as the first and second rates. The flow controller 235 can use control signals to control the driving of the mixture of the first fluid and the second fluid and to control the rate of delivery. It also may be desirable to flush the common line of a non-medicinal first fluid such as saline, at a rate even higher than the combined rate to expedite delivery of the second medication. In scenarios where drug library-defined limits are assigned for one or both of the two fluid delivery rates, the pump system may allow overrides of the upper rate limit for one or both of the fluids during the common line flush. For example, the pump system could effectively apply these delivery limits upon delivery to the patient, versus upon delivery from the pump. In another embodiment, the method 550 of FIG. 5A may be modified at block 556 such that the infusion pump drives a fluid combination at a rate that is a ratio of a first programmed first fluid rate and a programmed second fluid rate.

At block 558, the flow controller 235 can monitor volume of the mixture of first and second fluids driven at the first rate. The flow controller 235 can determine when the monitored volume is equal to the common line flush volume value. When it is determined that the monitored volume equals or exceeds the common line flush volume, the method 550 proceeds to block 560, where the flow controller 235 continues driving the mixture of the first and second fluids, but at the combined rate. In some embodiments, the flow controller 235 can measure an amount of time before changing the rate of the mixture fluid delivery to the combined rate. In one embodiment, the flow controller 235 can further include incrementing a first fluid displayed volume and a second fluid displayed volume by a proportion of the monitored volume when the monitored volume is equal to or greater than an internal volume of the common line. The proportion of monitored volume to be incremented for each of the first and second fluids can be equal to the proportion of first and second flow rates associated with the first and second fluids, respectively. For example, if the first flow rate is 10 ml/hr and the second flow rate is 5 ml/hr, the proportions of the monitored value incremented on the first and second volume displays will have a 2:1 ratio. If the monitored volume is 3 ml, then the display of the first fluid value will be increased by 2 ml and the display of the second fluid value will be increased by 1 ml. The flow controller 235 can thus accurately track the rate, time, and an amount of each fluid delivered to the patient. In some embodiments, the flow controller 235 executes only some of the steps described above with respect to FIG. 5A. Furthermore, the flow controller 235 can change the order of the steps, include additional steps, or modify some of the steps discussed above.

The common line flush volume value can be selected as desired for a particular application. In one embodiment, the common line flush volume value is an internal volume of the common line. In another embodiment, the common line flush volume value is an internal volume of the common line plus or minus an adjustment volume. The adjustment volume can be any volume desired as a safety factor to assure that the common line is free of the first fluid before the second fluid is infused at the second rate.

In one embodiment, the method 550 further includes incrementing a first fluid displayed volume by the monitored volume when driving a mixture of the first and second fluids at the first rate. The first fluid displayed volume is incremented by the monitored volume when the monitored volume is equal to or greater than an internal volume of the common line.

In some embodiments, the method 550 ends after the concurrent infusion at the combined rate ends. However, in other embodiments, the method 550 continues concurrent delivery of the first and second fluids until one of the fluids is depleted or until the desired volume of one of the fluids has been delivered. In such case, for example, when the second fluid reservoir is depleted, the infusion continues according to the method 580 discussed below with respect to FIG. 5B. If instead, the concurrent infusion continues until the desired volume of one of the fluids has been delivered, then the infusion may continue according to a slightly modified method 580, as discussed below with respect to FIG. 5B.

Concurrent Delivery to Infusion Completion with Common Line Auto Flush

Figure 5B:
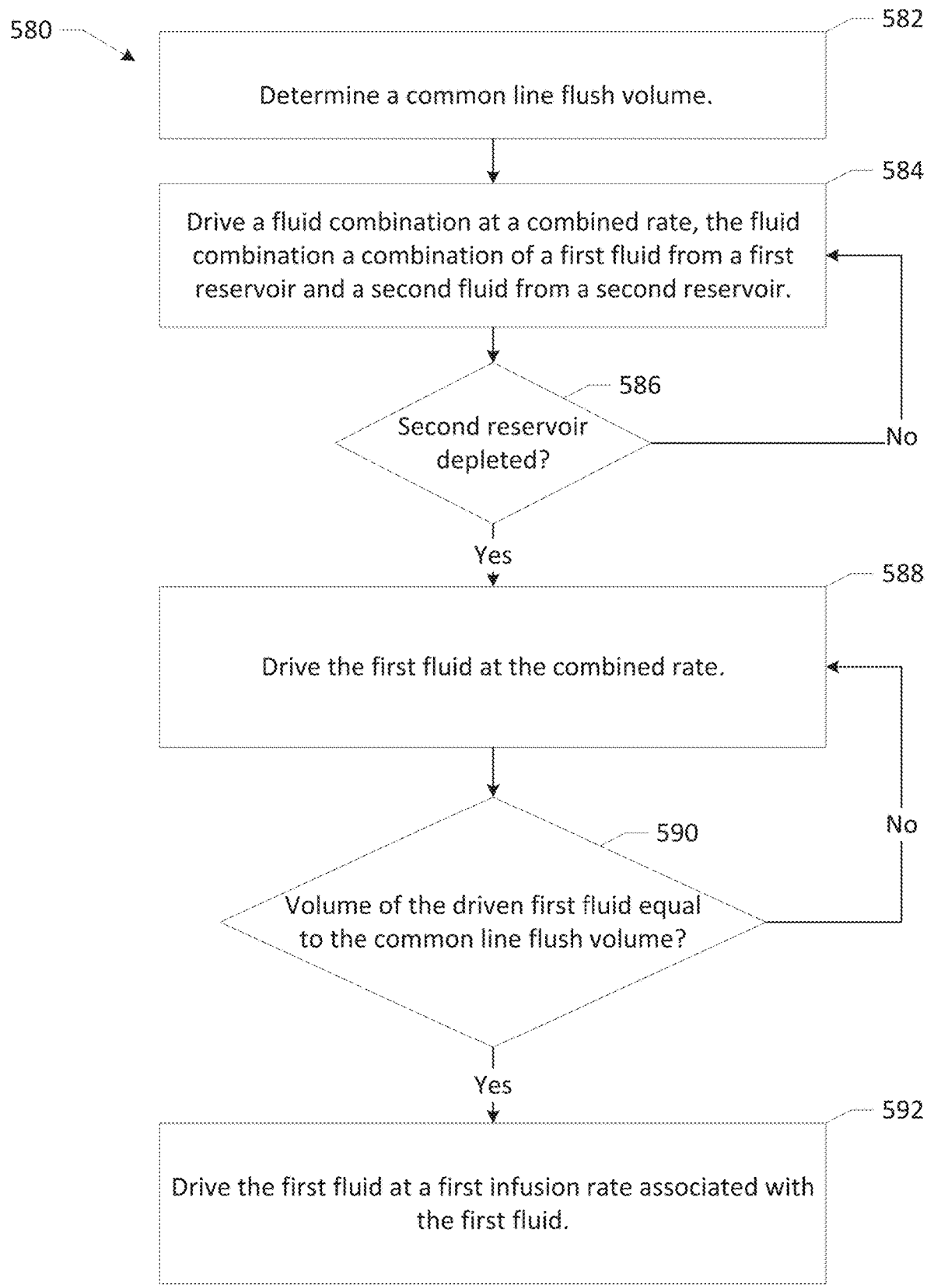
FIG. 5B is a flowchart of a method of providing a secondary infusion until the secondary reservoir is depleted in accordance with the present invention that may be performed by the infusion pumps of FIGS. 1-3.

FIG. 5B illustrates a method 580 of safely performing a concurrent infusion of first and second fluids until the volume of the second fluid reservoir is depleted (e.g., totally depleted or emptied of the second fluid), such that no second fluid or substantially no second fluid remains in the second reservoir. The method 580 can be performed by a flow controller (e.g., flow controller 235) alone and/or in conjunction with the method 550 of FIG. 5A. For example, method 580 may be performed beginning at block 586 and following block 560 of method 550 of FIG. 5A. A drug library may include an indication (e.g., flag, value, etc.) to enable or disable infusion until depletion functionality, as described with respect to FIG. 5B.

At block 582, the method 580 determines a common line flush volume of a common line. Any of the methods described herein may be used to determine the common line flush volume. At block 584, a concurrent infusion occurs, where a fluid combination is driven by an infusion pump at a combined rate. The fluid combination includes a mixture of a first fluid drawn into a junction and/or mixing chamber from a first reservoir and a second fluid drawn into the junction and/or mixing chamber from a second reservoir. As discussed herein, a first infusion rate may be associated with the infusion of the first fluid and a second infusion rate may be associated with the infusion of the second fluid. The ratio of the volumes of first and second fluids drawn into the mixing chamber is equal to the ratio of the ratio of first and second infusion rates. The fluid combination is driven from the junction and/or mixing chamber to the common line at a combined rate, which may be determined according to any of the methods described herein. For example, the combined rate may be determined as the sum of the first and second infusion rates.

At block 586, the method 580 determines whether the second reservoir has been depleted. For example, a sensor can detect whether there is air or air bubbles in the line between the junction and the second reservoir. If the method 580 does not determine that the second reservoir is depleted, the method 580 returns to block 584. If the method 580 determines that the second reservoir has been depleted, the method 580 proceeds to block 588. The method 580 may also optionally cause the infusion pump to at least partially back-prime the line between the junction and the second reservoir. For example, the infusion pump may pump some fluid from the first reservoir to force fluid into the line between the junction and the second reservoir in order to remove air from the line (or at least the portion of the line near the junction).

In a modified version of method 580, at block 586 the method 580 instead determines whether a desired or programmed volume of the second fluid has been delivered. For example, if the infusion pump was programmed to delivery only 100 ml of the second fluid during concurrent delivery mode, the method 580 would determine whether 100 ml of the second fluid had been delivered. In another embodiment, the method 580, determines whether a desired volume of second fluid has been delivered by receiving a command to stop an infusion of the second fluid. When a user provides an input to stop the infusion, the method 580 determines that the desired volume of second fluid has been delivered. If so, the method 580 continues to block 588. If not, the method 580 returns to block 584.

At block 588, the method 580 stops drawing fluid from the second reservoir, and instead only draws fluid from the first reservoir. The method 580 drives the first fluid to the common line at the combined rate in order to auto flush or clear the volume of the common line of the fluid combination remaining in the common line. In the case when there is a drug-library defined limit on the first fluid, the pump system may need to allow an override of this limit in order to support pumping of the first fluid at the combined rate. In other words, drug library-defined delivery limits for the first fluid would apply at the patient, versus at the pump.

At block 590, the method 580 monitors the volume of first fluid driven at the combined rate and determine when the monitored volume equals or exceeds the common line flush volume. If the monitored volume is not equal to the common line flush volume, the method 580 returns to block 588. If the monitored volume is equal to or exceeds the common line flush volume, the method 580 proceeds to block 592.

Figure 5C:
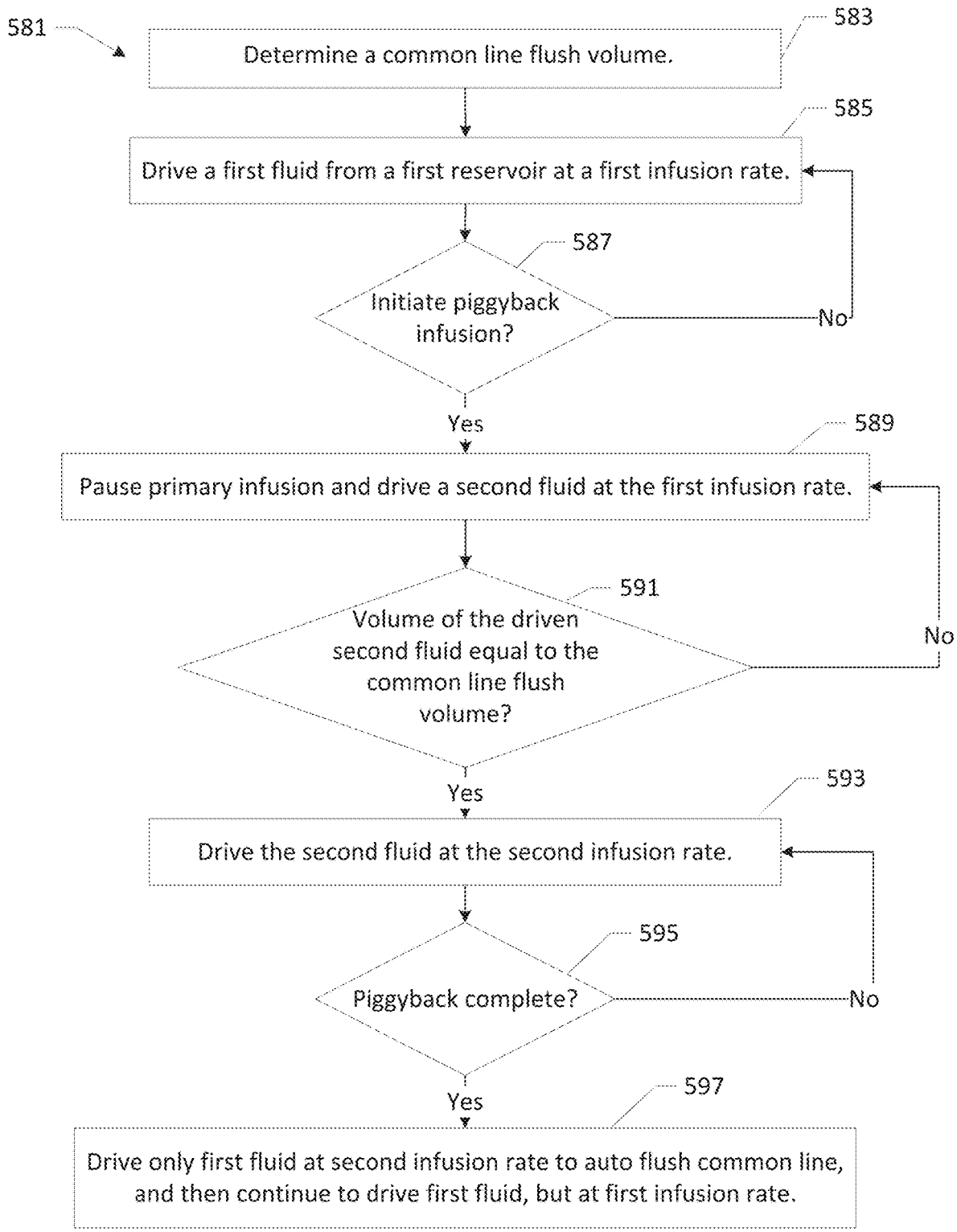
FIG. 5C is a flowchart of a method of providing sequential infusions, where a primary infusion is provided until the primary reservoir is depleted in accordance with the present invention that may be performed by the infusion pumps of FIGS. 1-3.

At block 592, the method 580 continues to draw the first fluid from the first reservoir, but at the first rate. In some embodiments, the method 580 can measure an amount of time before changing the rate of the first fluid delivery to the first rate. In one embodiment, the method 580 can further include incrementing a first fluid displayed volume and a second fluid displayed volume by a proportion of the monitored volume when the monitored volume is equal to or greater than an internal volume of the common line. The proportion of monitored volume to be incremented for each of the first and second fluids can be equal to the proportion of first and second flow rates associated with the first and second fluids, respectively. For example, if the first flow rate is 10 ml/hr and the second flow rate is 5 ml/hr, the proportions of the monitored value incremented on the first and second volume displays will have a 2:1 ratio. If the monitored volume is 3 ml, then the display of the first fluid value will be increased by 2 ml and the display of the second fluid value will be increased by 1 ml. The method 580 can thus accurately track the rate, time, and an amount of each fluid delivered to the patient. In some embodiments, the method 580 executes only some of the steps described above with respect to FIG. 5B. Furthermore, the method 580 can change the order of the steps, include additional steps, or modify some of the steps discussed above Sequential Delivery to Reservoir Depletion with Common Line Auto Flush FIG. 5C illustrates a method 581 of safely performing a sequential infusion (sometimes referred to as a piggyback infusion) of a first fluid at a first infusion rate until the infusion of the first fluid at the first rate is stopped and the infusion switches to an infusion of a second fluid at a second infusion rate. The method 581 can be performed by a flow controller (e.g., flow controller 235) alone and/or in conjunction with the method 550 of FIG. 5A or the method 580 of FIG. 5B. A drug library may include an indication (e.g., flag, value, etc.) to enable or disable infusion until reservoir depletion functionality, as described with respect to FIG. 5B.

At block 583, the method 581 determines a common line flush volume of a common line. Any of the methods described herein may be used to determine the common line flush volume. At block 585, a primary infusion occurs, where a first fluid is driven by an infusion pump at a first infusion rate. The first fluid is drawn into a junction and/or mixing chamber from a first reservoir. The first infusion rate may be associated with the infusion of the first fluid and a second infusion rate may be associated with an infusion of the second fluid. The first fluid is driven from the junction and/or mixing chamber to the common line at the first infusion rate.

At block 587, the method 581 determines whether to pause the first infusion and initiate a "piggyback" infusion, or infusion of a second fluid at a second rate. If the method 581 determines that the second fluid program should be initiated, the method 581 proceeds to block 589. If not, the method 581 returns to block 585.

At block 589, the method 581 stops drawing fluid from the first reservoir (pauses the primary infusion), and instead only draws fluid from the second reservoir. The method 581 drives the second fluid to the common line at the first infusion rate in order to auto flush or clear the volume of the common line of the first fluid remaining in the common line. If the drug library includes limits on the delivery of fluid 2, these limits may need to be allowed to be overridden during the common line flush period defined by block 589. For example, if fluid 1 was programmed at a rate below the lower limit allowed for fluid 2, or if fluid 1 was programmed at a rate above the upper limit allowed for fluid 2, an override of such a limit would be allowed during the common line flush.

At block 591, the method 581 monitors the volume of second fluid driven at the first infusion rate and determines when the monitored volume equals or exceeds the common line flush volume. If the monitored volume is not equal to the common line flush volume, the method 581 returns to block 589. If the monitored volume is equal to or exceeds the common line flush volume, the method 581 proceeds to block 593.

At block 593, the method 581 continues to draw the second fluid from the second reservoir, but at the second infusion rate. In some embodiments, the method 581 can measure an amount of time before changing the rate of the first fluid delivery to the second infusion rate. In one embodiment, the method 581 can further include incrementing a first fluid displayed volume by the monitored volume when the monitored volume is equal to or greater than an internal volume of the common line. The method 581 can thus accurately track the rate, time, and an amount of each fluid delivered to the patient. In some embodiments, the method 581 executes only some of the steps described above with respect to FIG. 5B. Furthermore, the method 581 can change the order of the steps, include additional steps, or modify some of the steps discussed above. In some embodiments, it may be preferable to infuse the second fluid at a rate that exceeds the first infusion rate until the common line (filled with non-medicinal fluid) is cleared, in order to more quickly introduce the second (medicinal) fluid to the patient. If a drug library defined limit for fluid 2 is present, the pump system may permit an override of this limit to allow pumping of fluid 2 at this increased rate. Similarly, there may be limits on fluid 1 delivery rates that should be considered by the pump system, imposing a limit on fluid 2 pumping rates intended to displace common line volume. At block 595, the method 581 determines whether the piggyback infusion is complete. For example, the method 581 may determine that the second reservoir is depleted of fluid, that a desired volume of fluid has been infused, that a desired infusion duration period has been reached, etc. In one embodiment, a sensor determines that air is detected within the fluid line. If the piggyback infusion is not complete, the method 581 returns to block 593. If the piggyback infusion is complete, the method 581 proceeds to block 597. At block 591, the primary infusion, e.g., the infusion of the first fluid, is resumed, though at the second infusion rate until the driven first fluid volume is equal to or greater than the common line volume. In the case where the first fluid has a drug library defined limit(s), the pump system may need to support an override of such a lower or upper limit to support pumping at the rate programmed for the second fluid. Method 581 then continues to drive the first fluid, but now at the first infusion rate.

The method 581 may also optionally cause the infusion pump to at least partially back-prime the line between the junction and the second reservoir after air is recognized at the depletion of the second fluid reservoir. For example, the infusion pump may pump some fluid from the first reservoir to force fluid into the line between the junction and the second reservoir in order to remove air from the line (or at least the portion of the line near the junction).

Intermittent Concurrent Delivery

Figure 6:
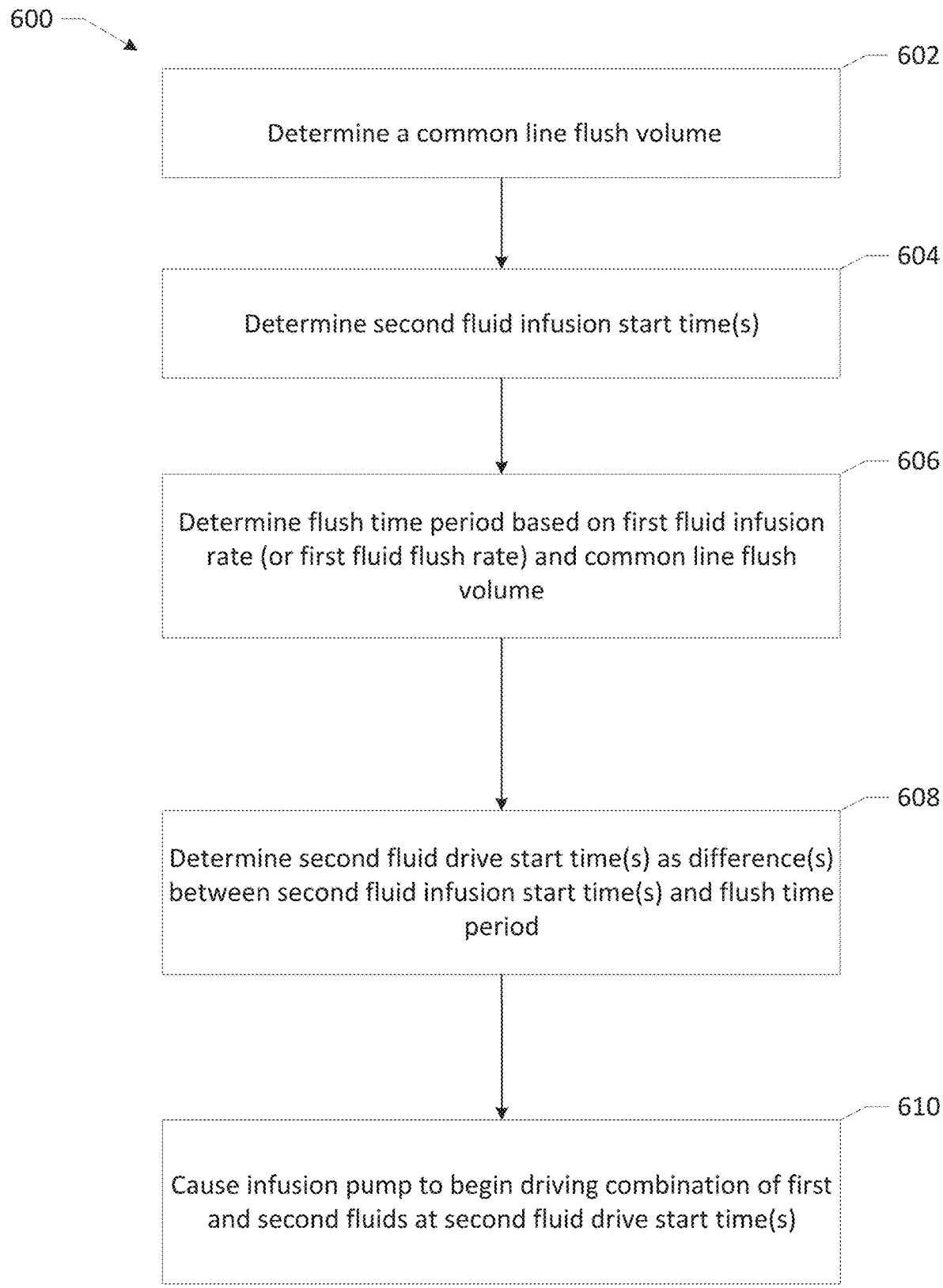
FIG. 6 is a flowchart of a method of determining fluid drive start times to cause infusions to reach a patient at desired infusion start times in accordance with the present invention that may be performed by the infusion pumps of FIGS. 1-3.

FIG. 6 illustrates a method 600 of scheduling intermittent concurrent deliveries. Method 600 can be performed by an infusion pump, a flow controller (e.g., flow controller 235), and/or alone or in conjunction with the method 550 of FIG. 5A and/or method 580 of FIG. 5B. Method 600 may be performed when it is desired to deliver a secondary infusion (e.g., deliver a second fluid via a concurrent infusion with a first fluid) multiple times per day at specific start times. Method 600 enables an infusion pump to determine a time to start an auto flush procedure to assure that the second fluid is infused into the patient (e.g., enters the patient) at the desired, specific start times.

For example, if a common line volume will take 10 minutes to flush at the primary (first) infusion rate, then the concurrent infusion will initiate an auto flush process (infusing a mixture of first and second fluids at the first infusion rate to flush the first fluid out of the common line tubing) 10 minutes before the desired secondary infusion start time (e.g., 10 minutes before the second fluid is to enter the patient).

At block 602, the method 600 determines a common line flush volume. However, the method may skip block 602 if the common line flush volume has already been determined. At block 604, the method 600 determines one or more second fluid infusion start times. For example, the method 600 may receive or download schedule information corresponding to desired start times to infuse a second fluid into a patient. The schedule information may define specific times during the day (e.g., 8 am, noon, 4 pm, 8 pm, etc.), it may define a number of infusions per day (e.g., 2, 3, 4, 6 infusions per day, etc.), or it may define an interval between second fluid infusions (e.g., one bag of second fluid every 4 hours, etc.). The schedule information may be used to determine one or more second fluid infusion start times.

At block 606, the method 600 determines a flush time period based on the first fluid infusion rate (or first fluid flush rate if a faster flush rate is desired for the particular, e.g., non-medicinal, first fluid) and the common line flush volume. For example, the flush time period may be determined by dividing the common line flush volume by the first fluid infusion rate (or first fluid flush rate). The flush time period represents the amount of time it will take to flush remaining fluid from the common line between the junction (or mixing chamber) and the common line distal end when fluid is driven at the first (or first fluid flush) rate.

At block 608, the method 600 determines second fluid drive start times, which correspond to the actual times that the infusion pump will begin to draw first fluid from a first reservoir and second fluid from a second reservoir, and drive the mixture of first and second fluids to the common line at the first (or first fluid flush) rate. In one embodiment, the method 600 may determine the second fluid drive start times by subtracting the flush time period from each of the second fluid infusion start times. For example, if the flush time period is determined to be 20 minutes and the second fluid infusion start times are 8:00 am, 2:00 pm, and 8:00 pm, then the second fluid drive start times may be determined as 7:40 am, 1:40 pm, and 7:40 pm. By initiating an auto flush concurrent infusion at the second fluid drive start times, a mixture of the second fluid and the first fluid will reach the patient and will be infused into the patient (e.g., enter the patient's body) at the second fluid infusion start times. At block 610, the method causes the infusion pump to initiate such auto flush concurrent infusions at the second fluid drive start times.

FIGS. 7A-7E are schematic diagrams of use for an infusion pump system with concurrent infusion and common line auto flush in accordance with the present invention. FIGS. 7A-7E illustrate switching from infusing a first fluid to infusing a mixture or combination of first and second fluids, then switching back to infusing the first fluid, while accounting for the previously infused fluid in the common line. In this example, the infusion pump is infusing a first fluid on a first flow path at a first rate and switches to infusing a mixture or combination of first and second fluids on a second flow path, maintaining the first rate long enough to clear the remaining first fluid from the common line before changing to a combined rate for infusing the mixture or combination of first and second fluids. The infusion pump then switches to infusing a first fluid on the first flow path, maintaining the combined rate long enough to clear the remaining mixture or combination of first and second fluids from the common line before changing to a first rate for infusing the first fluid.

Figure 7C:
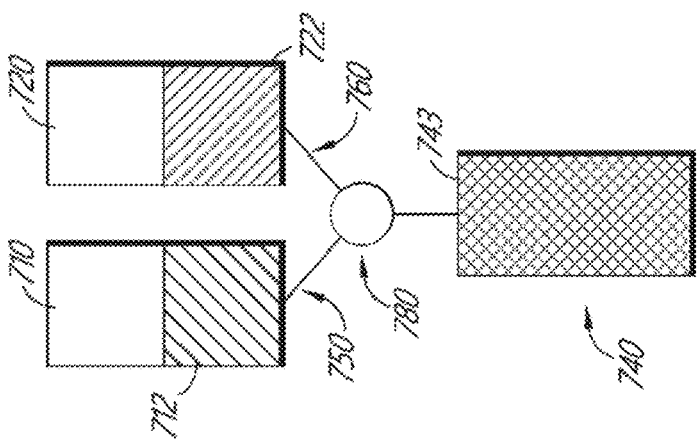
FIGS. 7A-7E are schematic diagrams of use for an infusion pump system with concurrent fluid delivery and common line auto flush in accordance with the present invention.
Figure 7B:
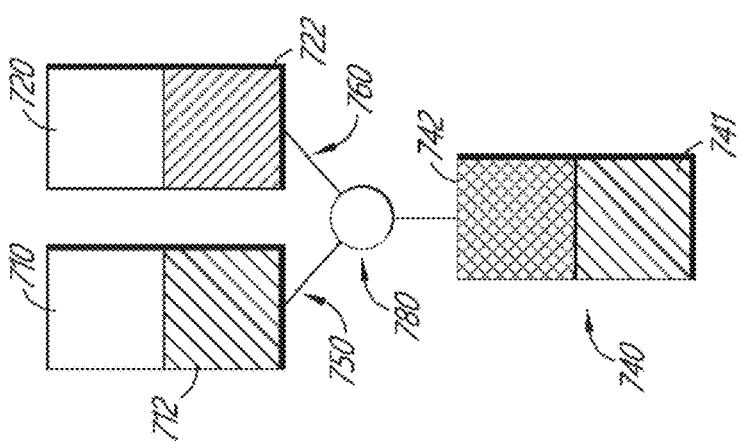
Figure 7A:
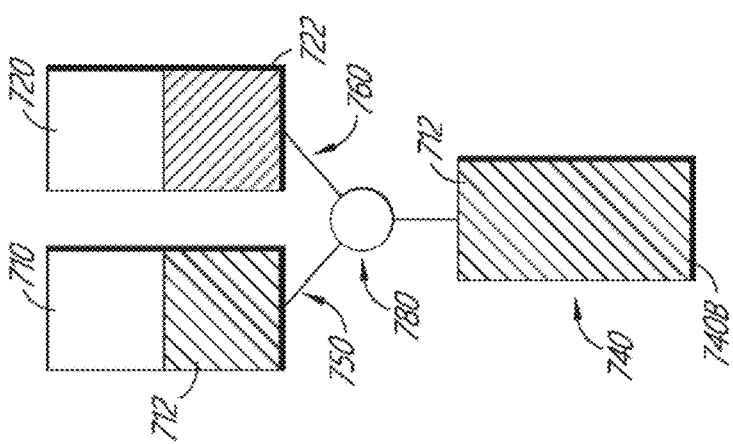

Referring to FIG. 7A, the first fluid 712 is delivered to the terminal end 740B of a common line 740 at a first rate along a first flow path 750 including the first reservoir 710, the junction 780, an optional mixing chamber (not shown), and the common line 740. The first fluid 712 is indicated by upward from left to right diagonal lines. Referring to FIG. 7B, the infusion has changed to a concurrent mode. During the concurrent mode, first fluid 712 is drawn from the first reservoir 710 and second fluid 722 is drawn from the second reservoir 720 along a second flow path 760. The second fluid 722 is indicated by downward from left to right diagonal lines. The mixture of first and second fluids 712, 722 is driven by the infusion pump into the common line 740. During this auto flush mode of concurrent delivery, the common line 740 contains first common line fluid 741 remaining from the initial infusion of the first fluid 712 and indicated by the upward diagonal lines, and second common line fluid 742 (the mixture of the first and second fluids 712, 722) indicated by the hashed lines. The flow rate remains at the first rate because the remaining first common line fluid 741 is being delivered to the terminal fluid delivery end 740B or to the patient when connected. Referring to FIG. 7C, none of the first fluid remains in the common line 740, so the second common line fluid 743 (the mixture of the first and second fluids 712, 722) is driven at the combined rate.

Figure 7D:
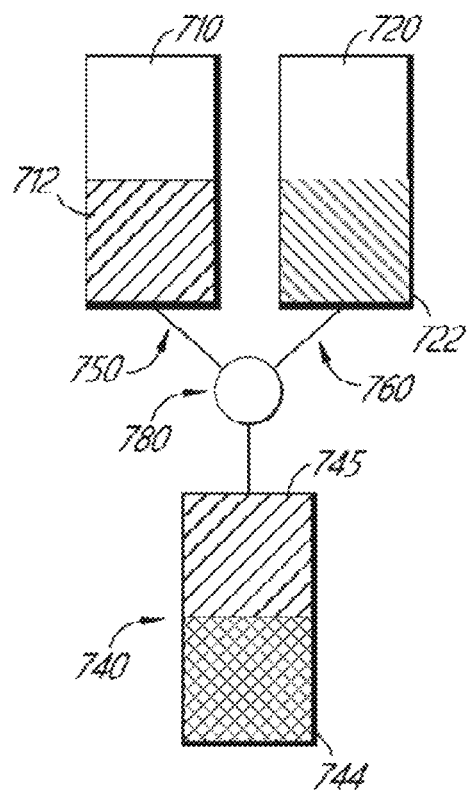
Figure 7E:
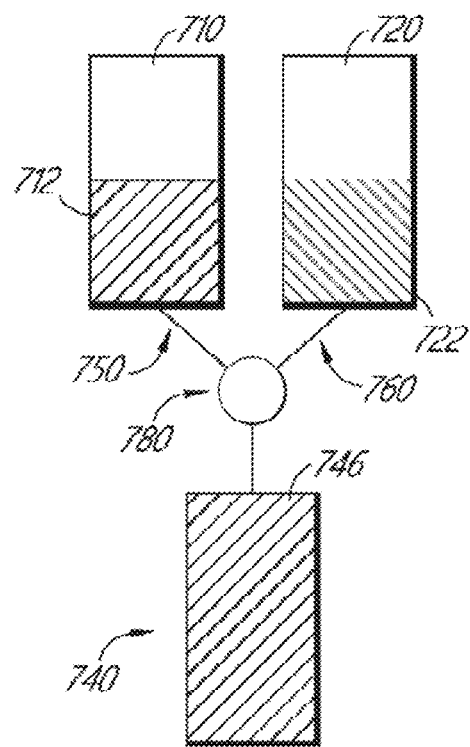

The infusion pump system can subsequently switch back to infusing only the first fluid (for example, after a predetermined time period, after a predetermined volume of combined first and second fluids are infused, after a predetermined volume of the second fluid is infused, or after the infusion pump determines that the second reservoir has been depleted of the second fluid, etc.). Referring to FIG. 7D, the infusion mode has changed from concurrent delivery to primary delivery (infusing only first fluid 712 from the first reservoir 710). Initially, the common line 740 still contains a mixture of the first and second fluids 712, 722 (represented by the hashed lines) as second common line fluid 744 remaining from the previous infusion, and first common line fluid 745 (the first fluid 712 alone) indicated by the upward diagonal lines. The flow rate remains at the combined rate because the remaining second common line fluid 744 is being delivered. Referring to FIG. 7E, none of the mixture of first and second fluids remains in the common line 740, so the first common line fluid 746 is driven at the first rate along the first flow path 750.

While the embodiments of the invention disclosed herein are presently considered to be preferred, various changes, rearrangement of steps, and modifications can be made without departing from the scope of the invention. The scope of the invention is indicated in the appended claims, and all changes that come within the meaning and range of equivalents are intended to be embraced therein.

What is claimed is:

1. A method for controlling operation of an infusion pump of an infusion pump system, the infusion pump system comprising a first reservoir configured to hold a first fluid, a second reservoir configured to hold a second fluid, a junction in fluid communication with the first reservoir and the second reservoir, a common line in fluid communication with the junction and having a terminal fluid delivery end, and the infusion pump, wherein the infusion pump is operable to drive fluid through the common line toward the terminal fluid delivery end, the method comprising:
    receiving instructions to deliver the first fluid at a first rate, subsequently concurrently deliver a mixture of the first fluid and the second fluid, and concurrently deliver the first fluid at the first rate and the second fluid at a second rate;
    infusing the first fluid at the first rate along a first flow path, the first flow path including the common line;
    determining a common line volume corresponding to a volume of the common line;
    drawing the first fluid from the first reservoir and the second fluid from the second reservoir to deliver the mixture of the first fluid and the second fluid into a first end of the common line;
    infusing the mixture of the first fluid and the second fluid at a flushing rate into the first end of the common line, wherein infusing the mixture of the first fluid and the second fluid at the flushing rate into the first end of the common line causes displacement of a volume of the first fluid remaining in the common line and infusion of the first fluid out of a terminal end of the common line at the flushing rate;
    determining that an infused volume of the mixture of the first fluid and the second fluid equals or exceeds the common line volume; and
    changing infusion of the mixture of the first fluid and the second fluid from the flushing rate to a combined rate in response to determining that the infused volume of the mixture of the first fluid and the second fluid equal or exceeds the common line volume, wherein the combined rate is a sum of the first rate and the second rate, and continue to infuse the mixture of the first fluid and the second fluid at the combined rate.

2. The method of claim 1, wherein the infusion pump system further comprises a mixing chamber in fluid communication with the first reservoir, the second reservoir, and the common line.

3. The method of claim 1, further comprising determining the flushing rate based upon whether the first fluid is a medicinal fluid.

4. The method of claim 3, further comprising determining the flushing rate as the first rate when the first fluid is a medicinal fluid.

5. The method of claim 3, further comprising determining the flushing rate as the first rate increased by a flushing rate factor when the first fluid is not a medicinal fluid.

6. The method of claim 1, further comprising receiving the common line volume from a user input.

7. The method of claim 1, further comprising retrieving the common line volume from a memory.

8. The method of claim 1, further comprising retrieving the common line volume over a network.

9. The method of claim 1, wherein the common line volume is predetermined.

10. The method of claim 1, further comprising determining the common line volume based on the first fluid.

11. The method of claim 1, wherein the first rate is different than the second rate.

12. The method of claim 1, wherein receiving the instructions further comprises receiving the instructions from an input via a user interface.

13. The method of claim 1, wherein infusing the mixture of the first fluid and the second fluid at the flushing rate comprises one or more of delivering the first fluid at a flush rate outside of drug library defined rate limits associated with the first fluid or delivering the second fluid at a second fluid flush rate outside of drug library defined rate limits associated with the second fluid.

14. The method of claim 1, further comprising:
determining that an infusion of the second fluid has completed;
drawing the first fluid from the first reservoir without drawing the second fluid from the second reservoir;
infusing the first fluid at the combined rate;
determining that a volume of the first fluid infused at the combined rate equals or exceeds the common line volume; and
changing infusion of the first fluid from the combined rate to the first rate.

15. The method of claim 14, further comprising determining that an infusion of the second fluid has completed by comparing a volume of fluid infused to a programmed volume to infuse.

16. The method of claim 14, further comprising determining that an infusion of the second fluid has completed by receiving an instruction to stop infusing the second fluid.

17. The method of claim 14, further comprising determining that an infusion of the second fluid has completed by determining that the second reservoir has been depleted of second fluid.

18. The method of claim 14, wherein infusing the first fluid at the combined rate comprises infusing the first fluid at a rate that exceeds a drug library rate limit associated with the first fluid.

19. The method of claim 1, further comprising:
determining that an infusion of the first fluid has completed;
drawing the second fluid from the second reservoir without drawing the first fluid from the first reservoir;
infusing the second fluid at the combined rate;
determining that a volume of the second fluid infused at the combined rate equals or exceeds the common line volume; and
changing infusion of the second fluid from the combined rate to the second rate.

20. The method of claim 19, further comprising determining that an infusion of the first fluid has completed by comparing a volume of fluid infused to a programmed volume to infuse.

21. The method of claim 19, further comprising determining that an infusion of the first fluid has completed by receiving an instruction to stop infusing the first fluid.

22. The method of claim 19, further comprising determining that an infusion of the first fluid has completed by determining that the first reservoir has been depleted of first fluid.

23. The method of claim 19, wherein infusing the second fluid at the combined rate comprises infusing the second fluid at a rate that exceeds a drug library rate limit associated with the second fluid.

* * * * *